US00RE48557E

(19) United States
(12) Reissued Patent
Theodorescu et al.

(10) Patent Number: US RE48,557 E
(45) Date of Reissued Patent: May 18, 2021

(54) ANTI-CANCER COMPOUNDS TARGETING RAL GTPASES AND METHODS OF USING THE SAME

(71) Applicant: THE REGENTS OF THE UNIVERSITY OF COLORADO, a body corporate, Denver, CO (US)

(72) Inventors: Dan Theodorescu, Los Angeles, CA (US); Michael Fitzpatrick Wempe, Aurora, CO (US); David Ross, Niwot, CO (US); Chao Yan, Santa Cruz, CA (US); Phillip Reigan, Castle Rock, CO (US)

(73) Assignee: The Regents of the University of Colorado, a body corporate, Denver, CO (US)

(21) Appl. No.: 16/553,092

(22) Filed: Aug. 27, 2019

Related U.S. Patent Documents

Reissue of:
(64) Patent No.: 10,202,397
Issued: Feb. 12, 2019
Appl. No.: 15/324,629
Filed: Jul. 10, 2015

U.S. Applications:
(60) Provisional application No. 62/022,946, filed on Jul. 10, 2014.

(51) Int. Cl.
*C07D 491/052* (2006.01)
*A61P 35/04* (2006.01)
*A61K 31/4162* (2006.01)
*A61K 45/06* (2006.01)

(52) U.S. Cl.
CPC ..... *C07D 491/052* (2013.01); *A61K 31/4162* (2013.01); *A61K 45/06* (2013.01); *A61P 35/04* (2018.01)

(58) Field of Classification Search
CPC ..... C07D 491/052; A61P 35/04; A61P 35/00; A61K 45/06; A61K 31/4162; A61K 2300/00
See application file for complete search history.

(56) References Cited

U.S. PATENT DOCUMENTS

| | | | |
|---|---|---|---|
| 4,555,396 | A | 11/1985 | Frank et al. |
| 5,750,550 | A | 5/1998 | Eissenstat et al. |
| 6,143,471 | A | 11/2000 | Takata et al. |
| 8,642,660 | B2 | 2/2014 | Goldfarb |
| 9,353,121 | B2 | 5/2016 | Theodorescu et al. |
| 2007/0105105 | A1 | 5/2007 | Clelland et al. |
| 2007/0155766 | A1 | 7/2007 | Zheng et al. |
| 2009/0221559 | A1 | 9/2009 | Bonfanti et al. |
| 2009/0221568 | A1 | 9/2009 | Shaw et al. |
| 2011/0003298 | A1 | 1/2011 | Liew |
| 2011/0257184 | A1 | 10/2011 | Qu et al. |
| 2012/0214824 | A1 | 8/2012 | Tait et al. |
| 2012/0252792 | A1 | 10/2012 | Neubig et al. |
| 2016/0280715 | A1 | 9/2016 | Theodorescu et al. |

FOREIGN PATENT DOCUMENTS

| | | | |
|---|---|---|---|
| CN | 103910737 | 7/2014 | |
| JP | H10-279480 | 10/1998 | |
| WO | WO 2008/143894 | 11/2008 | |
| WO | WO 2011/010715 | 1/2011 | |
| WO | WO 2013/096820 | 6/2013 | |
| WO | WO 2013/096852 | 6/2013 | |
| WO | WO-2013096820 A1 * | 6/2013 | ..... A61K 31/437 |
| WO | WO 2013/152313 | 10/2013 | |
| WO | WO 2013/182472 | 12/2013 | |

OTHER PUBLICATIONS

"Accession No. RN 53316-58-8," Database Registry, Chemical Abstracts Service, Columbus, Ohio, Nov. 16, 1984, 3 pages.
"Accession No. RN 168429-49-0," Database Registry, Chemical Abstracts Service, Columbus, Ohio, Oct. 5, 1995, 2 pages.
Abdelrazek et al. "Synthesis and Molluscicidal Activity of Some 1,3,4-Triaryl-5-chloropyrazole, Pyrazolylphthalazine and Pyrano[2,3-d]thiazole Derivatives," Arch Pharm Chemistry in Life Sciences, Jun. 2006, vol. 339, No. 6, pp. 305-312.
Al-Matar et al., "Green One Pot Solvent-Free Synthesis of Pyrano[2,3-c],-Pyrazoles and Pyrazolo[1,5-a]Pyrimidines," Molecules, 2010, vol. 15, pp. 6619-6629.
Albadi et al., "CuO—CeO2 nanocomposite: A highly efficient recyclable catalyst for the multicomponent synthesis of 4H-benzo[b]pyran derivatives," Chinese Chemical Letters, 2013, vol. 24, pp. 821-824.
Al-Duaij, "An Eco-friendly Method for Novel Scaffolds: Novel N2-Substituted Fused Pyrazolo (4',3':5,6) Pyrano (2,3-d) Pyrimidine Terminated by Hydroxy Group," J. Chem. Chem. Eng., 2013, vol. 7, pp. 821-828.
Al-Mutairi et al., "Microwave versus ultrasound assisted synthesis of some new heterocycles based on pyrazolone moiety," Journal of Saudi Chemical Society, 2010, vol. 14, pp. 287-299.
Babaie et al., "Nanosized magnesium oxide as a highly effective heterogeneous base catalyst for the rapid synthesis of pyranopyrazoles via a tandem four-component reaction," Arabian Journal of Chemistry, 2011, vol. 4, pp. 159-162.
Balaskar et al., "Greener approach towards the facile synthesis of 1,4-dihydropyrano[2,3-c]pyrazol-5-yl cyanide derivatives at room temperature," Chinese Chemical Letters, 2010, vol. 21, pp. 1175-1179.
Bhosale et al., "One-pot three-component condensation for the synthesis of 1,4-dihydropyrano[2,3-c]pyrazoles using cesium fluoride as an efficient catalyst," J. Chem. Pharm. Res., 2014, vol. 6(4), pp. 733-737.
Chobe et al. "Green approach towards synthesis of substituted pyrazole-1, 4-dihydro,9-oxa, 1,2,6,8-tetrazacyclopentano[b]naphthalene-5-one derivatives as antimycobacterial agents," Medicinal Chemistry Research, Feb. 2013, vol. 22, No. 11, pp. 5197-5203.

(Continued)

*Primary Examiner* — Jerry D Johnson
(74) *Attorney, Agent, or Firm* — Sheridan Ross P.C.

(57) ABSTRACT

Methods of inhibiting the growth or metastasis of a cancer in a subject by inhibiting a Ral GTPase in the subject, and small molecule inhibitors of Ral GTPases useful in the methods of the invention. Pharmaceutical compositions containing the compounds of the invention, and methods of using the same.

8 Claims, 20 Drawing Sheets

(56) References Cited

OTHER PUBLICATIONS

Dawane et al., "One-pot multicomponent sythesis and antimicrobial evaluation of some novel pyrano-[2,3-c]-pyrazoles derivatives," Der Pharma Chemica, 2011, vol. 3(3), pp. 300-305.
Dilthey et al. "Die Reaktionsfahigkeit [alfpha]-und[gamma]-stÄndiger Methylgruppen in Pyryliumsalzen. (Uber Pyryliumverbindungen, XIII.)," Berichte Der Deutschen Chemischen Gesellschaft, Jan. 1924, pp. 1653-1656.
Elinson et al., "Solvent-free and 'on-water' multicomponent assembling of aldehydes, 3-methyl-2-pyrazoline-5-one, and malononitrile: fast and efficient approach to medicinally relevant pyrano[2,3-c]pyrazole scaffold,", American Chemical Society, 2015, 35 pages.
Eskandari et al., "Novel silica sodium carbonate (SSC): Preparation, characterization and its first catalytic application to the synthesis of new dihydropyrano[2,3-C]pyrazoles," Catalysis Communications, 2014, vol. 54, pp. 124-130.
Farahi et al., "An environmentally friendly synthesis of 1,4-dihydropyrano[2,3-c]pyrazole derivatives catalyzed by tungstate sulfuric acid," Chinese Chemical Letters, 2014, vol. 25, pp. 1580-1582.
Gujar et al., "Molecular sieves: an efficient and reusable catalyst for multi-component synthesis of dihydropyrano[2,3-C]pyrazole derivatives," Tetrahedron Letters, 2014, vol. 55, pp. 6030-6033
Guo et al., "D,L-Proline-Catalyzed One-Pot Synthesis of Pyrans and Pyrano[2,3-c]pyrazole Derivatives by a Grinding Method under Solvent-Free Conditions," Synthetic Communications: An International Journal for Rapid Communication of Synthetic Organic Chemistry, 2007, vol. 37, pp. 2111-2120.
Hafiz et al., "Synthesis of New Substituted 1,3-Diphenyl-5-chloropyrazoles," J. Chem. Res. (S), 1998, pp. 690-691.
Hamad et al. "Distinct requirements for Ras oncogenesis in human versus mouse cells," Genes & Development, Aug. 2002, vol. 16, No. 16, pp. 2045-2057.
Hasaninejad et al., "Silica bonded n-propyl-4-aza-1-azoniabicyclo[2.2.2]octane chloride (SB-DABCO): A highly efficient, reusable and new heterogeneous catalyst for the synthesis of 4H-benzo[b]pyran derivatives," Applied Catalysis A: General, 402, 2011, pp. 11-22.
Ilovaisky et al., "Green Approach to the Design of Functionalized Medicinally Privileged 4-Aryl-1,4-dihydropyrano[2,3-c]-pyrazole-5-carbonitrile Scaffold," J. Heterocyclic Chem., 2014, vol. 51, pp. 523-526.
Jin et al., "A Clean and Simple Synthesis of 6-Amino-4-Aryl-5-Cyano-3-Methyl-in Water," Synthetic Communications: An International Journal for Rapid Communication of Synthetic Organic Chemistry, 2005, vol. 35, pp. 137-143.
Kangani et al., "Green synthesis of 1,4-dihydropyrano[2,3-c]pyrazole derivatives using maltose as biodegradable catalyst," Res Chem Intermed, 2015, vol. 41, pp. 2513-2519.
Karimi-Jaberi et al., "Trichloroacetic acid as a solid heterogeneous catalyst for the rapid synthesis of dihydropyrano[2,3-c]pyrazoles under solvent free conditions," Heterocycl. Commun., 2011, vol. 17(5-6), pp. 177-179.
Khoobi et al., "New tetracyclic tacrine analogs containing pyrano[2,3-c]pyrazole: Efficient Synthesis, biological assessment and docking simulation study," American Chemical Society, 2015, 15 pages.
Khurana et al., "Rapid Synthesis of Polyfunctionalized Pyrano[2,3-c]pyrazoles via Multicomponent Condensation in Room-Temperature Ionic Liquids," Synthetic Communications: An International Journal for Rapid Communication of Synthetic Organic Chemistry, 2011, vol. 41, pp. 405-410.
Kiyani et al., "One-pot, four-component synthesis of pyrano [2,3-c]pyrazoles catalyzed by sodium benzoate in aqueous medium," Current Chemistry Letters, 2013, vol. 2, pp. 197-206.
Kshirsagar et al., "Mg—Al Hydrotalcite as a First Heterogeneous Basic Catalyst for the Synthesis of 4H-Pyrano [2,3-c]pyrazoles Through a Four-Component Reaction," Synthetic Communications: An International Journal for Rapid Communication of Synthetic Organic Chemistry, 2011, vol. 41, pp. 1320-1325.
Lehmann et al., "Three-Component Combinatorial Synthesis of Novel Dihydropyrano[2,3-c]pyrazoles", J. Comb. Chem., 2008, vol. 10, pp. 364-367.
Lim et al. "Activation of RalA is critical for Ras-induced tumorigenesis of human cells," Cancer Cell, Jun. 2005, vol. 7, pp. 533-545.
Makawana et al. "Microwave assisted synthesis and antimicrobial evaluation of new fused pyran derivatives bearing 2-morpholinoquinoline nucleus," bioorganic & Medicinal Chemistry Letters, Jul. 2011, vol. 21, No. 20, pp. 6166-6169.
Mamaghani et al., An efficient and eco-friendly synthesis and evaluation of antibactrial activity of pyrano[2,3-c]pyrazole derivatives, Med Chem Res, Sep. 25, 2014, 11 pages.
Mohamed et al., "Facile synthesis of fused nitrogen containing heterocycles as anticancer agents," Der Pharma Chemica, 2010, vol. 2(1), pp. 400-417.
Muramulla et al., "A new catalytic mode of the modularly designed organocatalysts (MDOs): enantioselective synthesis of dihydropyrano[2,3-c]pyrazoles," Tetrahedron Letters, 2011, vol. 52, pp. 3905-3908.
Paul et al., "Uncapped SnO2 quantum dot catalyzed cascade assembling of four components: a rapid and green approach to the pyrano[2,3-c]pyrazole and spiro-2-oxindole derivatives," Tetrahedron, 2014, vol. 70, pp. 6088-6099.
Pavlova et al., "Synthesis and cytotoxic activity of heterocyclization products of 1,1-dicyano-2-hetaryl-2-trifluoromethylethylenes," Russian Chem. Bulletin, Int'l Edition, Jan. 2010, vol. 59(1), pp. 162-176.
Reddy et al., "Glycine-Catalyzed Efficient Synthesis of Pyranopyrazoles via One-Pot Multicomponent Reaction," Synthetic Communications: An International Journal for Rapid Communication of Synthetic Organic Chemistry, 2010, vol. 40(19), pp. 2930-2934.
Ren et al., "Solvent-Free, One-Pot Synthesis of Pyrano[2,3-c]pyrazole Derivatives in the Presence of KF•2H20 by Grinding," Synthetic Communications: An International Journal for Rapid Communication of Synthetic Organic Chemistry, 2005, vol. 35(19), pp. 2509-2513.
Saad et al. "Synthesis of New Substituted 1, 3-Diphenyl-5-chloropyrazoles," Journal of Chemical Research, Jan. 1998, pp. 2946-2957.
Sheibani et al., "Three-Component Reaction to Form 1,4-Dihydropyrano[2,3-c]pyrazol-5-yl Cyanides," Synthetic Communications: An International Journal for Rapid Communication of Synthetic Organic Chemistry, 2009, vol. 40(2), pp. 257-265.
Shi et al., "Three-Component One-Pot Synthesis of 1,4-Dihydropyrano[2,3-c]pyrazole Derivatives in Aqueous Media," Synthetic Communications: An International Journal for Rapid Communication of Synthetic Organic Chemistry, 2004, vol. 34(24), pp. 4557-4563.
Smith et al. "The Metastasis-Associated Gene CD24 Is Regulated by Ral GTPase and Is a Mediator of Cell Proliferation and Survival in Human Cancer," Cancer Research, Feb. 15, 2006, vol. 66, No. 4, pp. 1917-1922.
Sohal et al., "Glycerol mediated, one-pot, multicomponent synthesis of dihydroppyrano[2,3-c]pyrazoles," European J. Chem., 2013, vol. 4(4), pp. 450-453.
Sohal et al., "Catalyst free, one-pot, facile synthesis of novel pyrazolo-1,4-dihydropyridine derivative form pyranopyrazoles," European J. Chem., 2014, vol. 5(2), pp. 227-232.
Tamaddon et al., "A four-component synthesis of dihydropyrano[2,3-c]pyrazoles in a new water-based worm-like micellar medium," Tetrahedron Letters, 2014, vol. 55, pp. 3588-3591.
Yan et al. "Discovery and characterization of small molecules that target the GTPase Ral," Nature, Nov. 20, 2014, vol. 515, No. 7527, pp. 443-447.
Yang et al., Synthesis and bioactivity of lignin related high-added-value 2H,4H-dihydro-pyrano[2,3-c]pyrazoles and 1H,4H-dihydro-pyrano[2,3-c]pyrazoles, Industrial Crops and Products, 2014, vol. 52, pp. 413-419.
Neel et al., "The RalGEF-Ral Effector Signaling Network: The Road Less Traveled for Anti-Ras Drug Discovery," Genes & Cancer, 2011, vol. 2(3), pp. 275-287.

(56) References Cited

OTHER PUBLICATIONS

International Search Report and Written Opinion for International Patent Application No. PCT/US2012/071341, dated Mar. 14, 2013, 7 pages.
International Report on Patentability for International Patent Application No. PCT/US2012/071341, dated Jul. 3, 2014, 6 pages.
Official Action (English translation) for Chinese Patent Application No. 201280070263.9, dated Sep. 16, 2015, 8 pages.
Official Action (English translation) for Chinese Patent Application No. 201280070263.9, dated Jun. 7, 2016, 6 pages.
Extended Search Report for European Patent Application No. 12859252.4, dated Apr. 16, 2015 8 pages.
International Search Report and Written Opinion for International Patent Application No. PCT/US15/40021, dated Oct. 7, 2015, 7 pages.
Official Action for U.S. Appl. No. 14/366,035, dated Feb. 12, 2015, 27 pages.
Official Action for U.S. Appl. No. 14/366,035, dated Jul. 28, 2015, 9 pages.
Notice of Allowance for U.S. Appl. No. 14/366,035, dated Feb. 1, 2016, 7 pages.
Official Action for U.S. Appl. No. 15/142,011, dated Dec. 14, 2016, 9 pages.
"Accession No. RN 2749-59-9," Database Registry Chemical Abstracts Service, Columbus, Ohio, Entered STN: Nov. 16, 1984, 1 page.
"Accession No. RN 361185-42-4," Database Registry Chemical Abstracts Service, Columbus, Ohio, Entered STN: Oct. 9, 2001, 2 pages.
Ito et al. "A medium-term rat liver bioassay for rapid in vivo detection of carcinogenic potential of chemicals," Cancer Science, Jan. 2003, vol. 94, No. 1, pp. 3-8.
Official Action for Australia Patent Application No. 2012358317, dated Dec. 2, 2016 5 pages.
English Translation of Official Action for China Patent Application No. 201280070263.9, dated Dec. 27, 2016 6 pages.
Official Action for European Patent Application No. 12859252.4, dated Mar. 10, 2017 8 pages.
Official Action with English Translation for Japan Patent Application No. 2014-548963, dated Mar. 7, 2017 6 pages.
International Preliminary Report on Patentability for International (PCT) Patent Application No. PCT/US2015/040021, dated Jan. 19, 2017 6 pages.
Official Action for U.S. Appl. No. 15/142,011, dated Jul. 12, 2017 12 pages.
Official Action for U.S. Appl. No. 15/142,011, dated Jun. 7, 2018, 7 pages.
Otto, "Darstellung einiger 4H-Pyrano[2.3-c]pyrazolderivate," Archiv der Pharmazie, 1974, pp. 444-447.
Tacconi et al., "A New Route to 4H-Pyrano[2,3-c] Pyrazoles," Journal of Drakt. Chemie., 1980, pp. 831-834.
Notice of Allowance for Australia Patent Application No. 2012358317, dated Dec. 4, 2017 3 pages.
Notice of Allowance (with English translation) for Chinese Patent Application No. 201280070263.9, dated Sep. 22, 2017, 5 pages.
Official Action for Canadian Patent Application No. 2954560, dated Nov. 22, 2017 4 pages.
Extended Search Report for European Patent Application No. 15819681.6, dated Nov. 28, 2017 11 pages.
Official Action (with English translation) for Japanese Patent Application No. 2014-548963, dated Jul. 17, 2018, 6 pages.
"Accession No. RN 362503-73-9," Database Registry Chemical Abstracts Service, Columbus, OH, Oct. 16, 2011, 2 pages.
Dewald et al., "Pyrazolodiazepines. 3. 4-Aryl-1,6,7,8-tetrahydro-1,3-dialkylpyrazolo[3,4-e][1,4]diazepines as Antidepressant Agents," Journal of Medical Chemistry, 1981, vol. 24, pp. 982-987.
Intention to Grant for European Patent Application No. 12859252.4, dated Jan. 23, 2018 5 pages.
Official Action with English Translation for Japanese Patent Application No. 2014-548963, dated Jan. 30, 2018 3 pages.
Official Action (with English translation) for Korean Patent Application No. 10-2017-7002960 dated Mar. 28, 2018 8 pages.
Official Action for U.S. Appl. No. 15/142,011, dated Feb. 2, 2018, 8 pages.

* cited by examiner

ANTI-CANCER COMPOUNDS TARGETING RAL GTPASES AND METHODS OF USING THE SAME

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATION

This application is a *Reissue of U.S. patent application Ser. No. 15/324,629, filed Jan. 6, 2017, now U.S. Pat. No. 10,202,397, which is a* national stage application under 35 U.S.C. 371 of PCT Application No. PCT/US2015/040021 having an international filing date of Jul. 10, 2015, which designated the United States, which PCT application claimed the benefit of U.S. Application Ser. No. 62/022,946, filed Jul. 10, 2014, both of which are incorporated herein by reference in their entirety.

GOVERNMENT INTEREST

This invention was made with Government support under grant numbers CA091846, CA075115 and CA104106 awarded by the National Institutes of Health. The U.S. Government has certain rights in the invention.

TECHNICAL FIELD

The invention relates to therapeutic compounds, pharmaceutical compositions containing the same and their use in the treatment of cancer.

BACKGROUND OF INVENTION

Ras is mutated in cancer more frequently than any other oncogene. Hence, Ras has been a focus for the development of rationally designed anti-cancer drugs, yet to date none have been successfully developed. In 1989, several groups showed that posttranslational modification of Ras proteins by farnesyl lipids is essential for Ras membrane association and transformation. Farnesyltransferase (FTase) was then purified and characterized and shortly thereafter, a second prenyltransferase, geranylgeranyltransferase type I (GGTase-I), that modifies Ras with a geranylgeranyl lipid was discovered. GGTase-I inhibitors (GGTIs) were studied and at least one such inhibitor, GGTI-2417, has been shown to inhibit the in vitro growth and survival of the MiaPaCa2 pancreatic cell line. But these inhibitory effects were modest and no clinical trials with GGTIs have followed.

Ral (Ras-like) GTPases are members of the Ras superfamily of GTPases, and function as molecular switches that cycle between the active GTP-bound an inactive GDP-bound states, becoming activated upon interaction with one of a family of Ral-specific guanine nucleotide exchange factors (Ral-GEFs), which promote GDP release from Ral allowing GTP to bind in its place. Ral-GEFs, along with Raf and phosphoinositide-3-kinase (PI3-K) constitute the three known classes of proteins whose activities are regulated by binding to Ras proteins in cells. Ral-GTPases share 46%-51% identity with human Ras, are an important component of Ras signaling and Ras oncogenesis and are an important effector of mutant Ras in tumors (Genes & Cancer 2011 2(3):275-287). Ral GTPases are also highly implicated in tumor metastasis, which is the major cause of death in cancer patients. Ral proteins are therefore clinically important targets for therapeutic intervention similar to Ras. But failure to obtain clinically useful inhibitors for Ras or any other GTPases suggests this target family is a therapeutic challenge. One reason for this is the inability to directly target the active site of small G proteins for inhibition because of their high affinity for the guanine nucleotides GDP/GTP and the millimolar concentration of these nucleotides in cells. Unlike Ras and other GTPases, however, RalA or RalB mutations are rare (<1%) in human cancer or cancer cell lines making the targeting of Ral a viable approach to developing effective anti-cancer therapeutics.

Thus, Ral GTPases present a compelling therapeutic target for the prevention and treatment of solid tumors and the metastasis of these cancers, and there exists a need for effective methods of inhibiting Ral GTPases for the treatment of cancer.

SUMMARY OF INVENTION

The present invention provides small molecules that bind to and effectively inhibit Ral GTPases, and therapeutic methods of using the same. The inventors' discovery was based on computational analysis that identified a site available in the inactive, but not the active, protein conformation that is distinct from the nucleotide binding pocket. Molecular docking of small molecules to this pocket followed by experimental verification yielded at least three compounds, which inhibited in vitro Ral binding to its effector RalBP1, Ral mediated cell spreading in murine fibroblasts and anchorage-independent growth of human cancer cell lines. Delivery of two chemically related compounds have shown favorable pharmacokinetics and tumor drug uptake in vivo. Synthesis of derivatives of these compounds led to compounds of the invention whose binding to RalB was confirmed by surface plasma resonance and $^{15}$N-HSQC NMR. These compounds inhibit xenograft growth to a similar extent as siRNA Ral depletion.

The compounds of the invention inhibit the activity of both RalA and RalB equally in human tumor xenografts. Although a distinct and sometimes even antagonistic role of RalA and RalB in tumorigenesis and metastasis has been proposed, genetic mouse models have revealed substantial redundancy in both development and tumorigenesis. These studies support the importance and clinical utility of compounds that inhibit both RalA and RalB GTPases.

The compounds of the invention are selective against Ral with little off target effects, mimicking the growth inhibition effects induced by Ral siRNA and inhibiting the activity of RalA and RalB but not the closely related GTPase Ras or RhoA in xenograft tumor samples. NMR titration experiments showed that these compounds only bind to RalB-GDP but not RalB-GTP, thereby preventing activation by Ral-specific guanine nucleotide exchange factors (Ral-GEFs) and GDP release from Ral, with GTP binding in its place, and inhibiting Ral activity-dependent phenotypes.

This computation-based screening, followed by biochemical, cellular and in vivo assays identified the small molecules of the present invention that bind to and effectively inhibit the activity of Ral proteins, for clinical use in cancer therapy. Thus, the present invention provides molecules that can inhibit Ral GTPases, as well as therapeutic uses of these molecules to prevent or slow the growth and metastasis of cancer in a subject. The invention also provides pharmaceutical compositions containing these compounds and methods of using these compounds and pharmaceutical compositions to treat or prevent cancer.

One aspect of the invention is a compound of the invention having Ral GTPase inhibitory activity and having the following chemical structure:

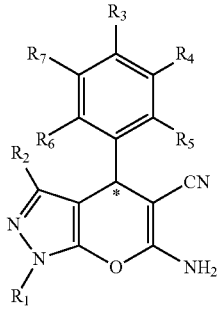

* chiral center and pharmaceutically acceptable enantiomers, diastereomers, racemates, and salts thereof, wherein:

and pharmaceutically acceptable enantiomers, diastereomers, racemates, and salts thereof, wherein:

$R_1$ is selected from hydrogen, halogen, —OH, —O—$R_8$, $C_1$-$C_{12}$ alkyl, $C_3$-$C_{12}$ alkenyl, $C_4$-$C_{12}$ dienyl, $C_6$-$C_{12}$ trienyl, $C_8$-$C_{12}$ tetraenyl, $C_6$-$C_{12}$ aryl, substituted $C_6$-$C_{12}$ aryl, $C_1$-$C_{12}$-alkoxy, carboxy, cyano, $C_1$-$C_{12}$ alkanoyloxy, $C_1$-$C_{12}$ alkylthio, $C_1$-$C_{12}$ alkylsulfonyl, $C_2$-$C_{12}$ alkoxycarbonyl, $C_2$-$C_{12}$ alkanoylamino, S—$R_8$, —$SO_2$—$R_8$, —$NHSO_2R_8$ and —$NHCO_2R_8$;

$R_2$ is selected from hydrogen, halogen, —OH, —O—$R_8$, $C_1$-$C_{12}$ alkyl, $C_3$-$C_{12}$ alkenyl, $C_4$-$C_{12}$ dienyl, $C_6$-$C_{12}$ trienyl, $C_8$-$C_{12}$ tetraenyl, $C_6$-$C_{12}$ aryl, substituted $C_6$-$C_{12}$ aryl, $C_1$-$C_{12}$-alkoxy, carboxy, cyano, $C_1$-$C_{12}$ alkanoyloxy, $C_1$-$C_{12}$ alkylthio, $C_1$-$C_{12}$ alkylsulfonyl, $C_2$-$C_{12}$ alkoxycarbonyl, $C_2$-$C_{12}$ alkanoylamino, S—$R_8$, —$SO_2$—$R_8$, —$NHSO_2R_8$ and —$NHCO_2R_8$;

$R_3$, $R_4$, $R_5$, $R_6$, and $R_7$ are independently selected from hydrogen, halogen, —OH, —O—$R_8$, $C_1$-$C_{12}$ alkyl, $C_3$-$C_{12}$ alkenyl, $C_4$-$C_{12}$ dienyl, $C_6$-$C_{12}$ trienyl, $C_8$-$C_{12}$ tetraenyl, imidazole, $C_6$-$C_{12}$ aryl, $C_1$-$C_{12}$-alkoxy, carboxy, cyano, $C_1$-$C_{12}$ alkanoyloxy, $C_1$-$C_{12}$ alkylthio, $C_1$-$C_{12}$ alkylsulfonyl, $C_2$-$C_{12}$ alkoxycarbonyl, $C_2$-$C_{12}$ alkanoylamino, S—$R_8$, —$SO_2$—$R_8$, —$NHSO_2$—$R_8$, —$NHCO_2$—$R_8$, $C_1$-$C_{12}$ alkyl optionally substituted with one to three groups selected from halogen, oxygen $C_1$-$C_6$ alkyl, $C_6$-$C_{10}$ aryl, and $C_1$-$C_6$ alkoxy, and $C_6$-$C_{12}$ aryl optionally substituted with one to three groups selected from halogen, $C_1$-$C_6$ alkyl, $C_6$-$C_{10}$ aryl, and $C_1$-$C_6$ alkoxy; or, $R_3$ and $R_4$ together form cyclohexane, 1,4-dioxane, or phenyl; and, $R_8$ is $C_1$-$C_{12}$ alkyl optionally substituted with one to three groups selected from halogen, oxygen, $C_1$-$C_6$ alkyl, $C_6$-$C_{10}$ aryl, and $C_1$-$C_6$ alkoxy, or $C_6$-$C_{12}$ aryl optionally substituted with one to three groups selected from halogen, $C_1$-$C_6$ alkyl, $C_6$-$C_{10}$ aryl, and $C_1$-$C_6$ alkoxy.

In certain embodiments, the $R_1$ substituent of the compound is selected from hydrogen, methyl, phenyl, methylphenyl, methoxy, $C_6$-$C_{12}$ aryl substituted with one to three groups selected from halogen, $C_1$-$C_6$ alkyl, and $C_1$-$C_6$ alkoxy.

In certain embodiments, the $R_2$ substituent of the compound is selected from hydrogen, methyl, phenyl, methylphenyl, methoxy, $C_6$-$C_{12}$ aryl substituted with one to three groups selected from halogen, $C_1$-$C_6$ alkyl, and $C_1$-$C_6$ alkoxy.

In certain embodiments, the $R_3$ substituent of the compound is selected from hydrogen, halogen, methoxy, $C_1$-$C_6$ alkyl optionally substituted with halogen, cyano, imidazole, and $C_6$-$C_{12}$ aryl substituted with one to three groups selected from halogen, and $C_1$-$C_6$ alkoxy.

In specific embodiments, the compound has a chemical structure selected from:

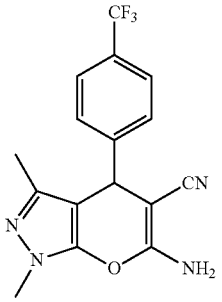

6-amino-1,3-dimethyl-4-(4-(trifluoromethyl)phenyl)-1,4-dihydropyrano[2,3-c]pyrazole-5-carbonitrile,

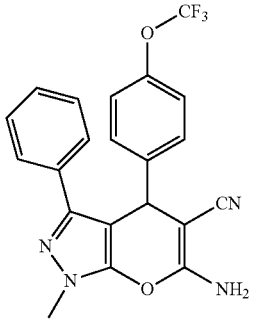

6-amino-1-methyl-3-phenyl-4-(4-(trifluoromethoxy)phenyl)-1,4-dihydropyrano[2,3-c]pyrazole-5-carbonitrile,

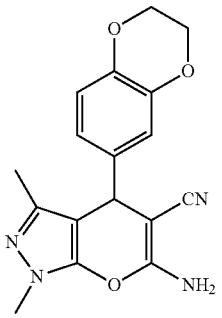

6-amino-4-(2,3-dihydrobenzo[b][1,4]dioxin-6-yl)-1,3-dimethyl-1,4-dihydropyrano[2,3-c]pyrazole-5-carbonitrile, and,

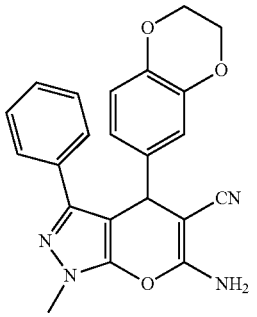

6-amino-4-(2,3-dihydrobenzo[b][1,4]dioxin-6-yl)-1-methyl-3-phenyl-1,4-dihydropyrano[2,3-c]pyrazole-5-carbonitrile.

Another aspect of the invention is a method of treating a cancer by administering to a subject in need of such treatment, a therapeutically-effective amount of a compound that inhibits Ral GTPase enzymatic activity. In one aspect of this embodiment, the compound inhibits at least one paralog of Ral GTPAse (either RalA or RalB), thereby inhibiting the growth or metastasis of a cancer. In a preferred aspect of this embodiment, the compound inhibits both RalA and RalB paralogs.

In a specific embodiment of these methods of treating or preventing a cancer in a subject, the compound is administered to the subject within a pharmaceutical composition of the invention.

Thus, another aspect of the invention is a pharmaceutical composition containing one or more of the compounds of the invention with at least one pharmaceutically-acceptable carrier.

Another embodiment of the invention is a method of preventing or treating metastatic cancers, particularly metastatic pancreas, prostate, lung, bladder, skin and/or colon cancers, by administering a therapeutically effective amount of at least one compound of the invention to a subject in need of such treatment or suspected of having a cancer or a metastasis of a cancer.

Another embodiment of the invention is a method of treating cancer by administering a therapeutically effective combination of at least one of the compounds of the invention and one or more other known anti-cancer or anti-inflammatory treatments. For example, other anti-cancer treatments may include prenyltransferase inhibitors, including geranylgeranyltransferase type I (GGTase-I) inhibitors, surgery, chemotherapy, radiation, immunotherapy, or combinations thereof.

Also provided herein are methods for the prevention, treatment or prophylaxis of cancer in a subject comprising administering to a subject in need thereof, therapeutically-effective amounts of any of the pharmaceutical compositions of the invention.

Also provided herein are methods for preventing the metastasis of a cancer in a subject comprising administering to the subject, therapeutically-effective amounts of at least one compound of the invention, including, for example, pharmaceutical compositions containing at least one compound of the invention.

Also provided herein are pharmaceutical packages comprising therapeutically-effective amounts of at least one compound of the invention within a pharmaceutical composition. The pharmaceutical compositions may be administered separately, simultaneously or sequentially with other compounds or therapies used in the prevention, treatment or amelioration of cancer in a subject. These packages may also include prescribing information and/or a container. If present, the prescribing information may describe the administration, and/or use of these pharmaceutical compositions alone or in combination with other therapies used in the prevention, treatment or amelioration of cancer in a subject.

Another embodiment of this invention is a method of testing the susceptibility of a subject having lung cancer to treatment with a putative inhibitor of Ral GTPase activity by testing the subject for a response to administration of the putative inhibitor indicative of growth inhibition or reduction in cancer cell number or tumor volume in the subject.

Other aspects of the invention will be set forth in the accompanying description of embodiments, which follows and will be apparent from the description or may be learned by the practice of the invention. However, it should be understood that the following description of embodiments is given by way of illustration only since various changes and modifications within the spirit and scope of the invention will become apparent to those skilled in the art and are encompassed within the scope of this invention.

BRIEF DESCRIPTION OF DRAWINGS

In FIGS. 1B and 1C, the sphere/surfaces indicate the water-accessible area in the binding cavity. All models were generated in Accelrys Discovery Studio software using published structures.

FIG. 3A shows the structure of BQU57, a derivative of RBC8. FIG. 3B is an overlay of the $^{15}$N-HSQC spectrum of 100 μM Ral-GDP and in the presence of 100 μM BQU57. FIG. 3C shows selected residues of RalB-GDP in the absence and presence of increasing concentrations of BQU57 at 40 μM and 100 μM. FIG. 3D shows a plot of chemical shift changes as a function of residue number comparing RalB-GDP alone (100 μM) and in the presence of 100 μM BQU57. FIG. 3E shows the binding of BQU57 to RalB-GDP determined using Isothermal Titration calorimetry (ITC).

Figure 4A:
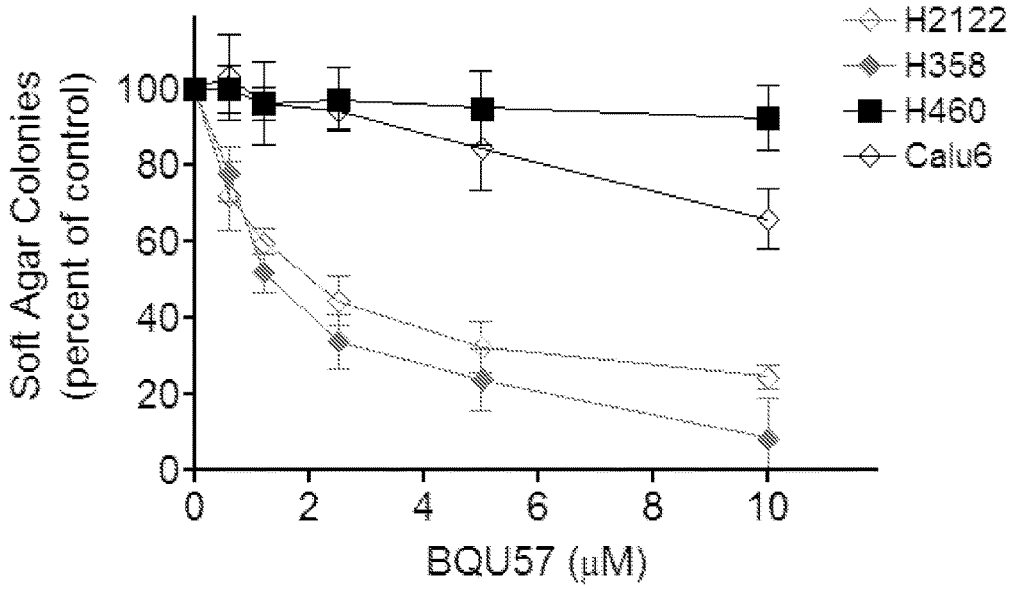
FIGS. 4A-4J shows the growth inhibitory activity of Ral inhibitors in human cancer cell lines. Effect of BUQ57 (FIG. 4A) and BQU85 (FIG. 4B) treatment on the anchorage-independent growth of four human lung cancer cell lines. Cells were seeded in soft agar containing various concentrations of drug; colonies formed in soft agar were counted after 2-4 weeks. Cell lines that are sensitive to Ral siRNA knockdown (H2122 and H358) are colored gray and cell lines resistant to Ral siRNA knockdown (H460 and Calu6)
Figure 4B:
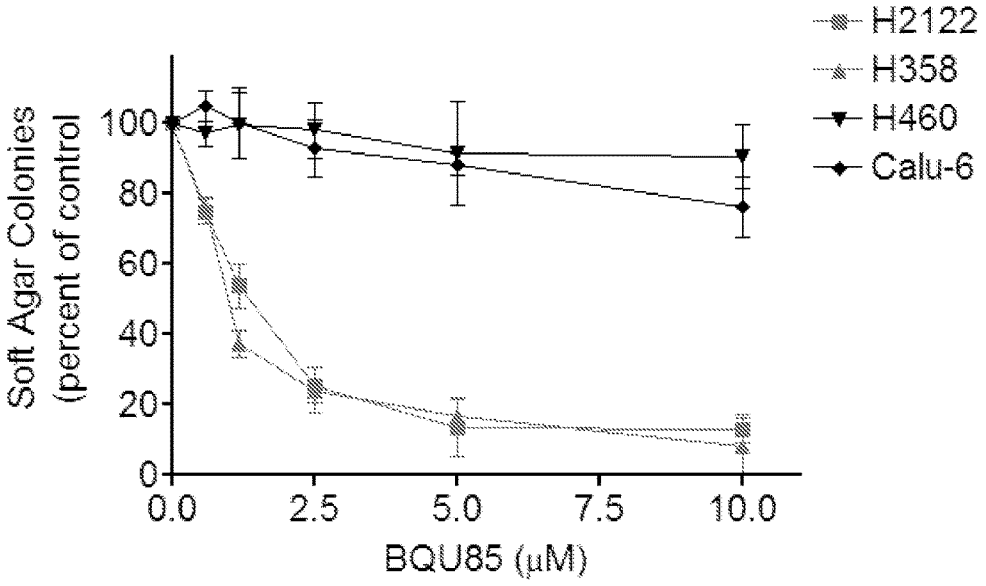
Figure 4C:
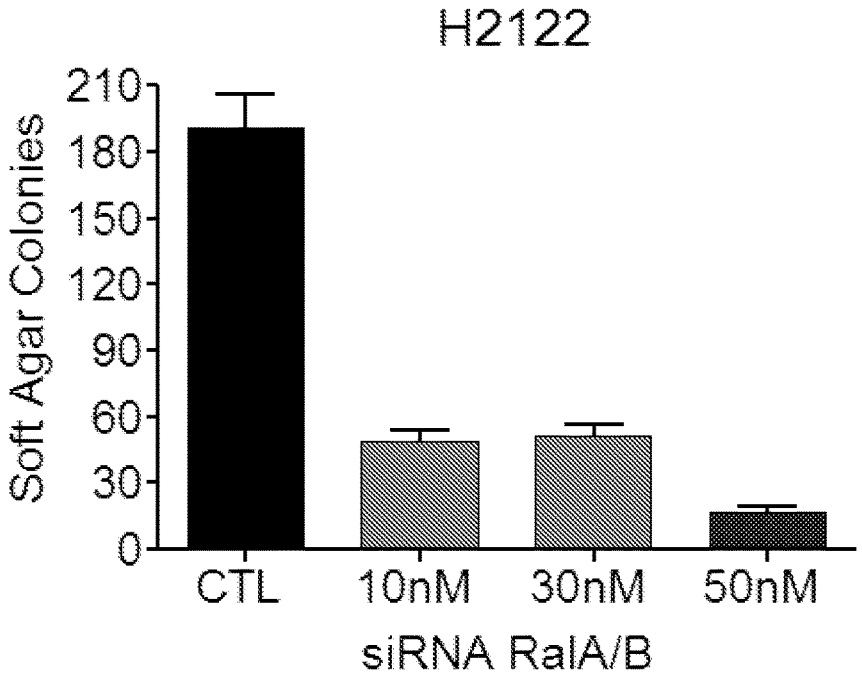
Figure 4D:
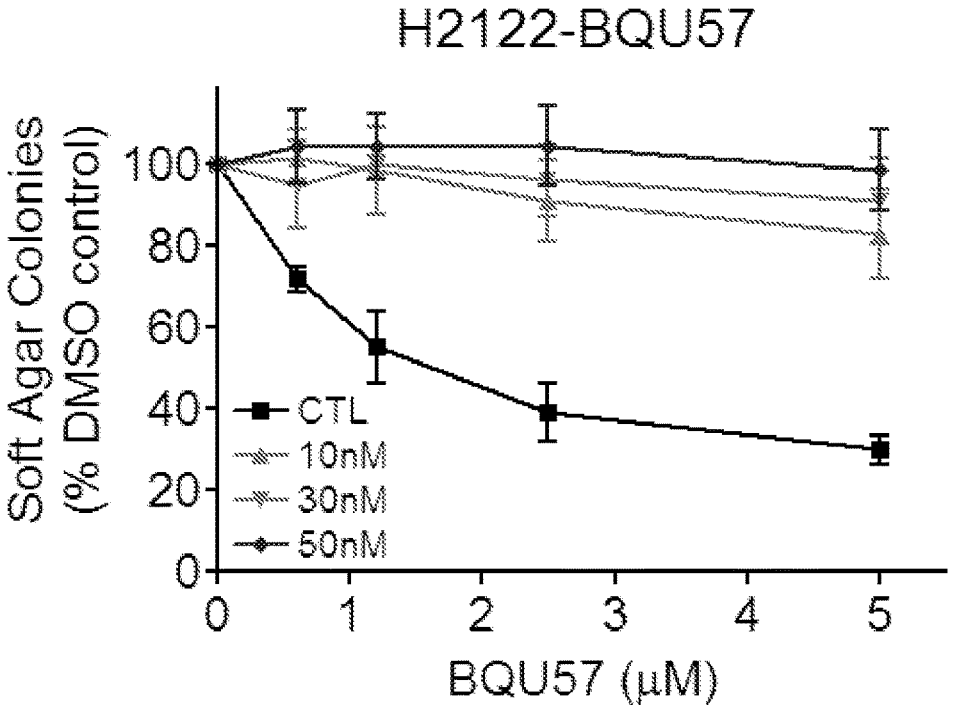
Figure 4E:
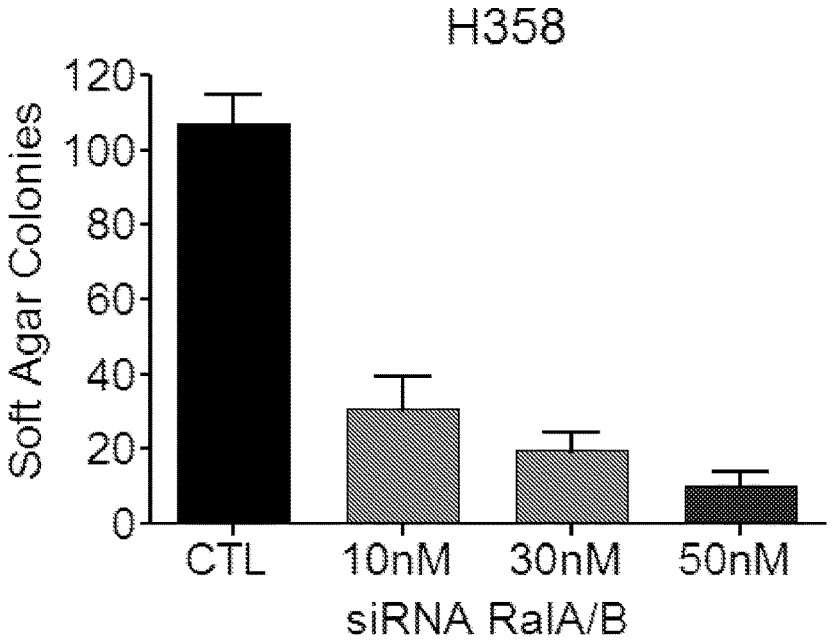
Figure 4F:
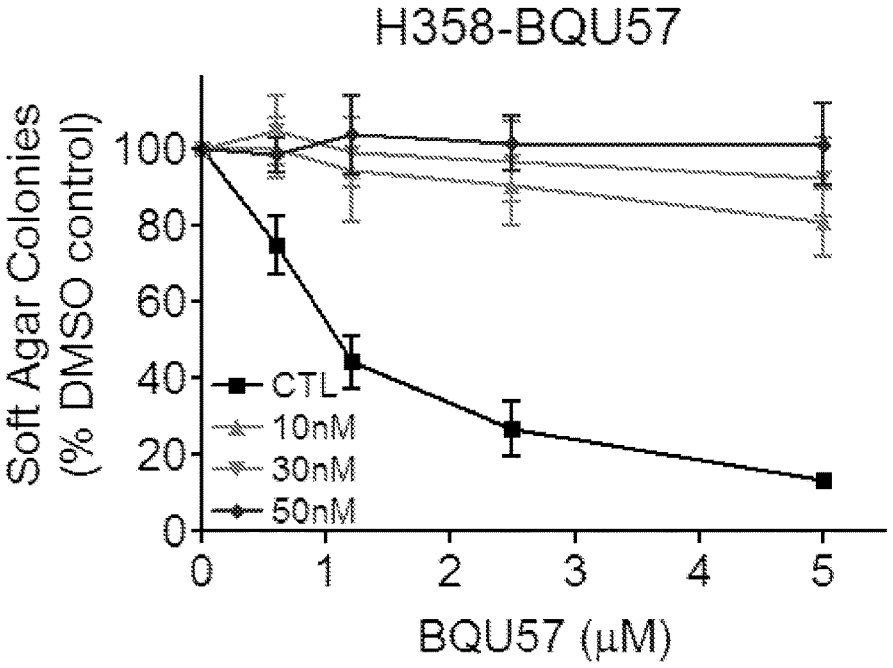
Figure 4G:
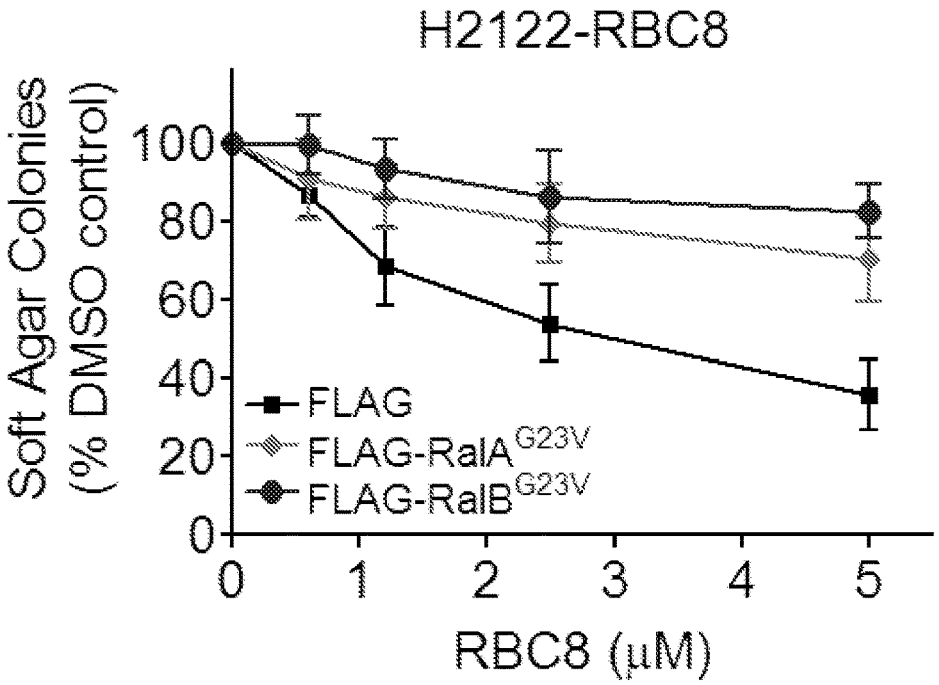
Figure 4H:
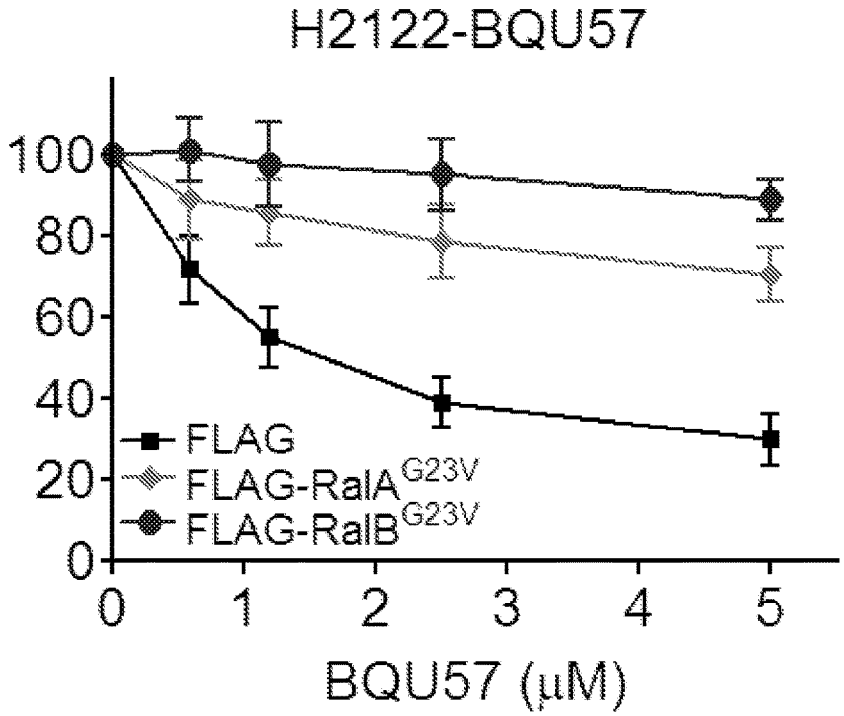
Figure 4I:
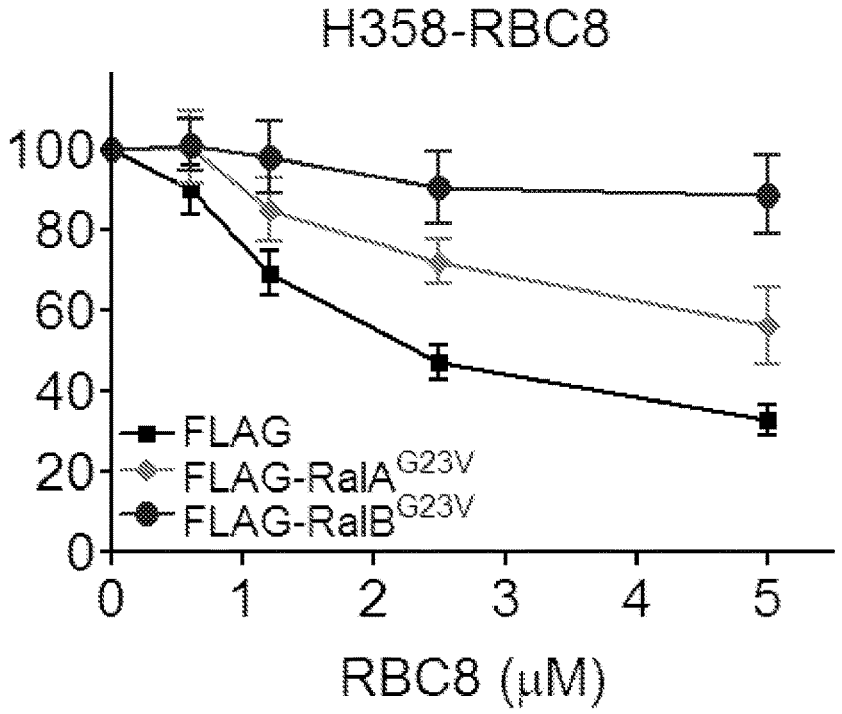
Figure 4J:
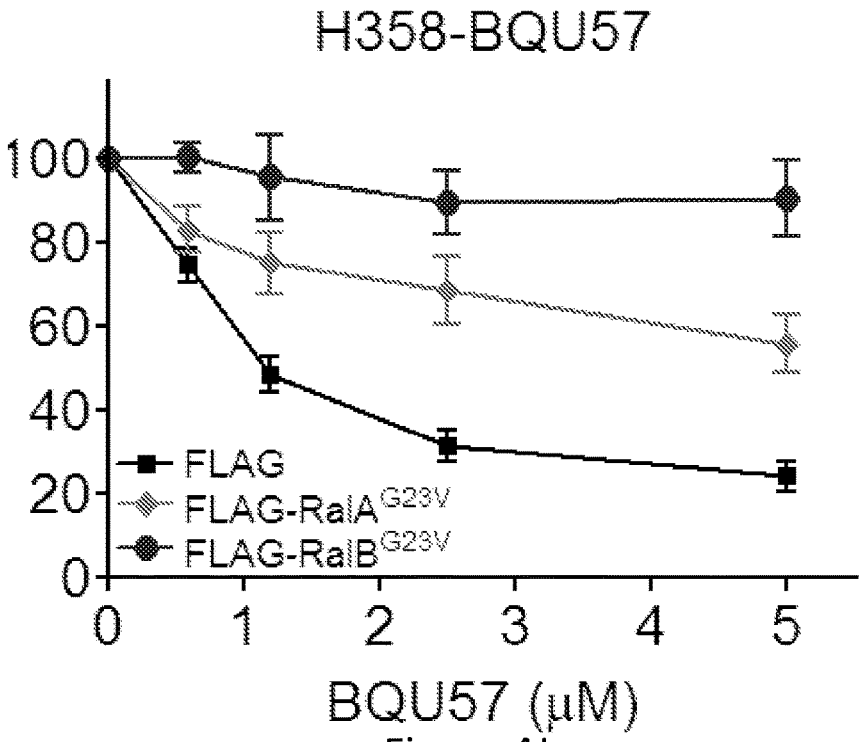

are colored black. Data represents the mean of three independent experiments. Effect of siRNA knockdown of both RalA and RalB in H2122 (FIGS. 4C, 4D) and H358 (FIGS. 4E, 4F) cells on drug-induced growth inhibition in soft agar. Cells were transfected with 10/30/50 nM of siRNA for 48 h, collected, and subjected to the soft-agar colony formation assay. Effect of siRNA alone on soft agar colony number is shown in FIG. 4C (H2122) and FIG. 4E (H358); effect of siRNA plus drug treatment on colony formation is shown as percent of DMSO treated control in FIG. 4D (H2122) and FIG. 4F (H358). Effect of the overexpression of constitutively active $RalA^{G23V}$ and $RalB^{G23V}$ in H2122 (FIGS. 4G, 4H) and H358 (FIGS. 41, 4J) cells on drug-induced growth inhibition in soft agar. H2122 cells were transiently transfected with FLAG-$RalA^{G23V}$ or FLAG-$RalB^{G23V}$ for 48 h before the soft agar colony formation assay. H358 cells were stably transfected with FLAG-$RalA^{G23V}$ or FLAG-$RalB^{G23V}$. Overexpression was confirmed by immunoblotting and shown in FIG. 7F. All results shown represent the mean±SD of three independent experiments. * denotes statistical significant difference between indicated groups.

Figure 5A:
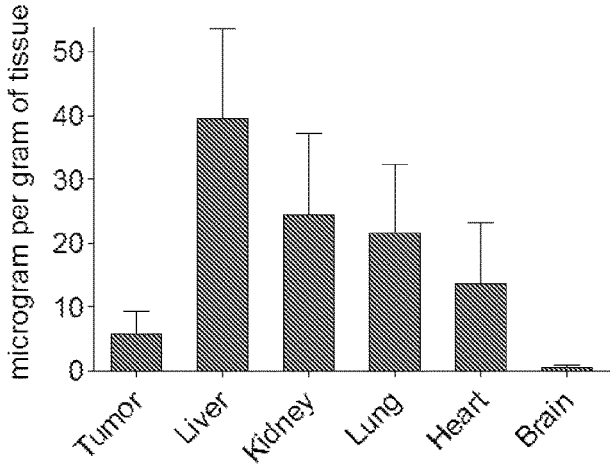
Figure 5B:
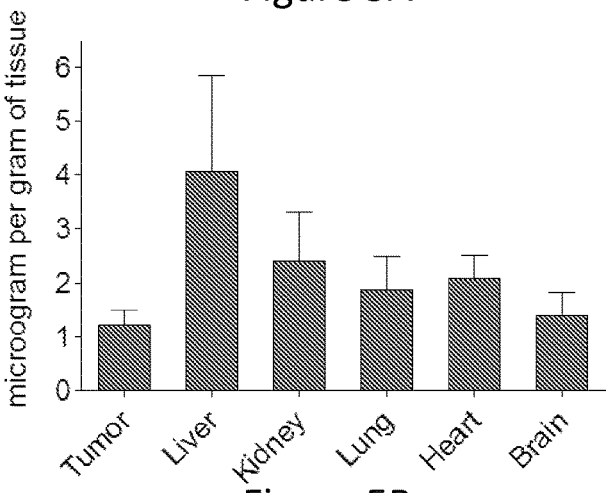
Figure 5C:
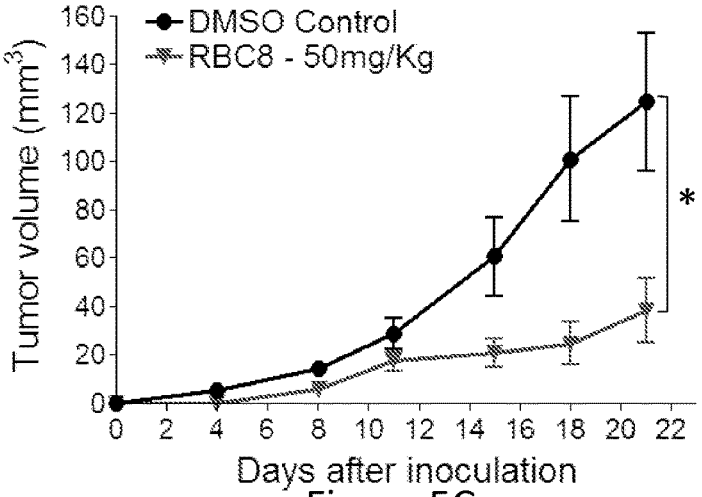
Figure 5D:
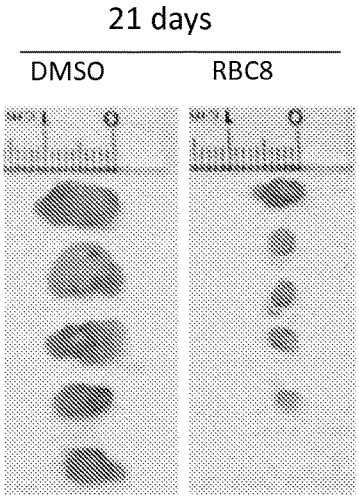
Figure 5E:
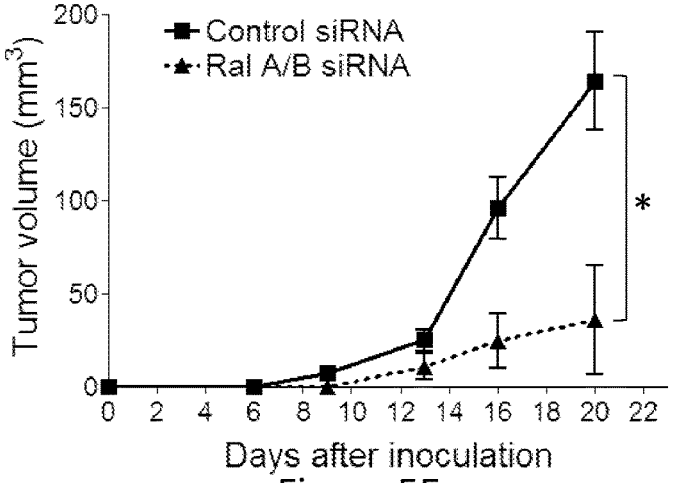
Figure 5F:
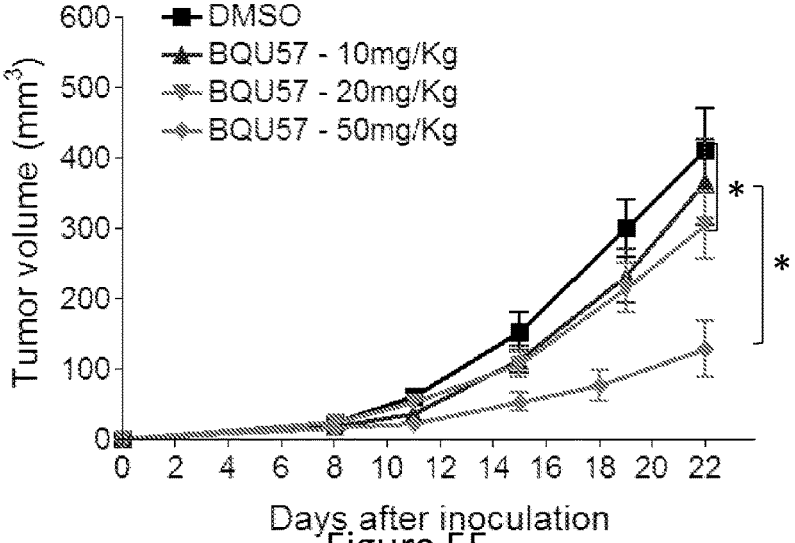
Figure 5G:
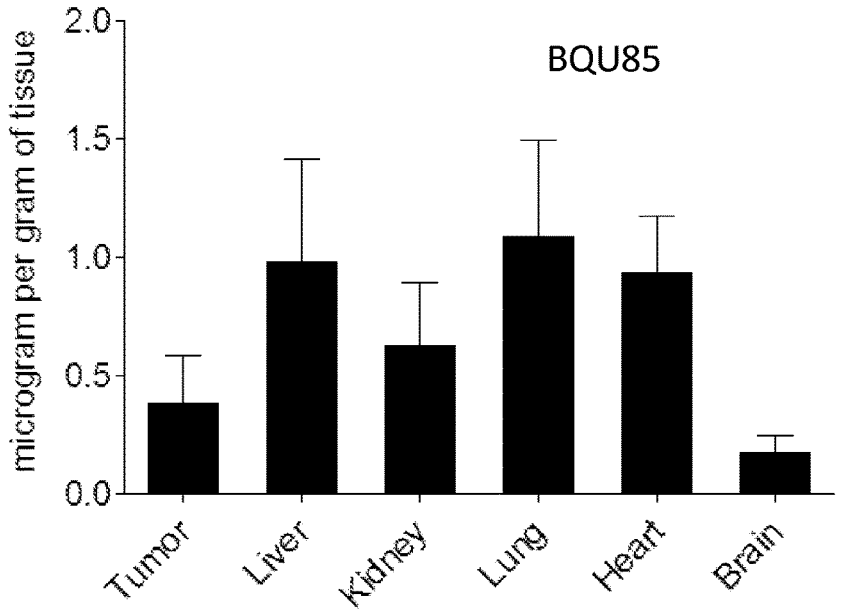
Figure 5H:
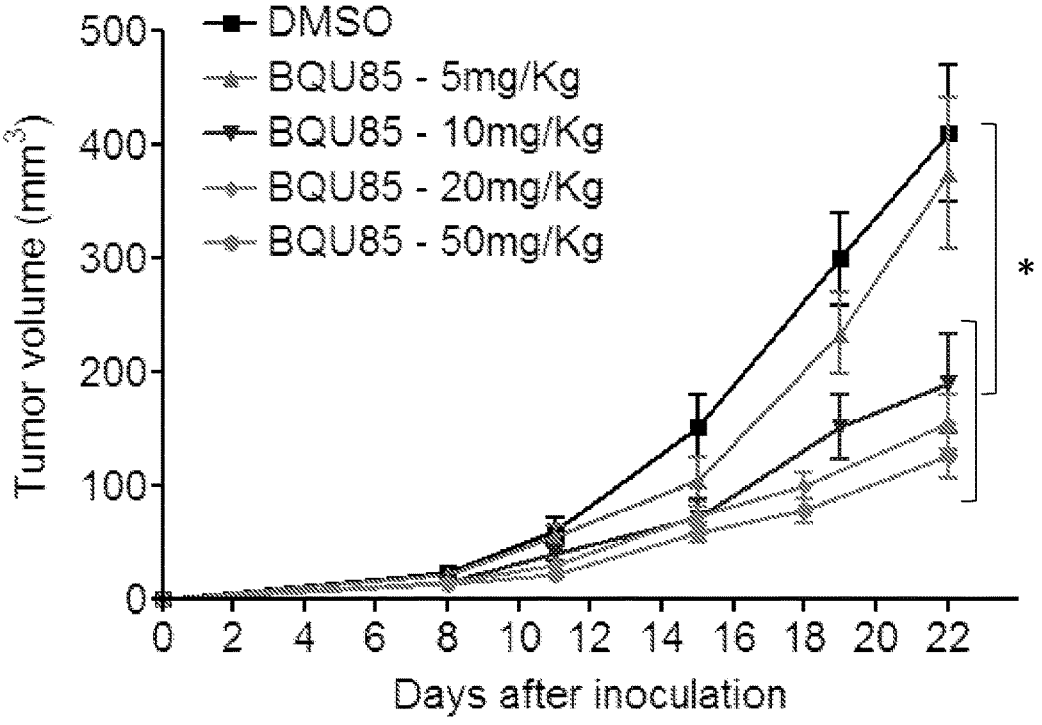

FIGS. 5A-5H show the effect of Ral inhibitors on human xenograft models of lung cancer. Tissue distribution of RBC8 (FIG. 5A) and BQU57 (FIG. 5B) in nude mice 3 h after a single i.p. dose of 50 mg/Kg; data represent the mean±SD of 3 mice. (FIG. 5C and FIG. 5D) 50 mg/kg/day RBC8 initiated 24 h after inoculation inhibited xenograft tumor growth of the human lung cancer cell line H2122. Data represents the mean±SEM of 6 mice. Tumor volume in the treatment group was statistically different from controls, as determined by the Dunnett's test (*$p<0.05$). Typical tumor appearance shown in FIG. 5D. FIG. 5E shows siRNA depletion of both RalA and RalB inhibited the xenograft tumor growth of H2122 cells. Cells were transiently transfected with siRNAs against both RalA and RalB for 24 h; cells were then inoculated into nude mice; tumors were monitored and measured as described above. Data represents the mean±SEM of 6 mice. Tumor volume in the treatment group was statistically different from controls as determined by the Dunnett's test (*$p<0.05$). FIG. 5F shows BQU57 treatment (10/20/50 mg/kg/day) initiated 24 h after inoculation inhibited xenograft tumor growth of H2122 cells. Data represents the mean±SEM of 6 mice. Tumor volume in the treatment group was statistically different from controls as determined by the Dunnett's test (*$p<0.05$). FIG. 5G shows the tissue distribution of BQU85 in nude mice 3 h after a single i.p. dose of 50 mg/Kg. Data represent the mean±SD of 3 mice. FIG. 5H shows the effect of BQU85 treatment on human xenograft models of lung cancer. BQU85 treatment (5/10/20/50 mg/kg/day) initiated 24 h after inoculation inhibited xenograft tumor growth of H2122 cells. Data represents the mean±SEM of 6 mice.

Figure 6D:
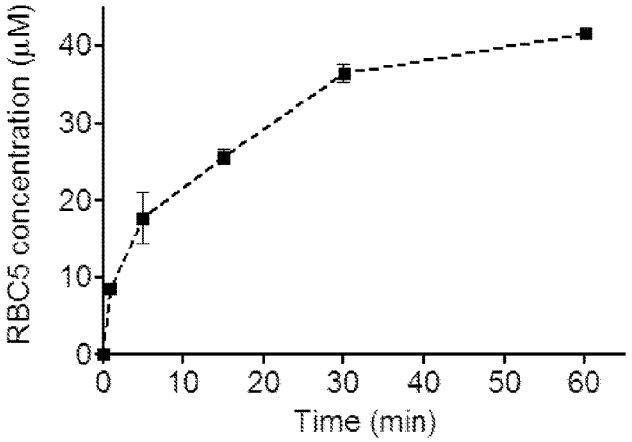
Figure 6A:
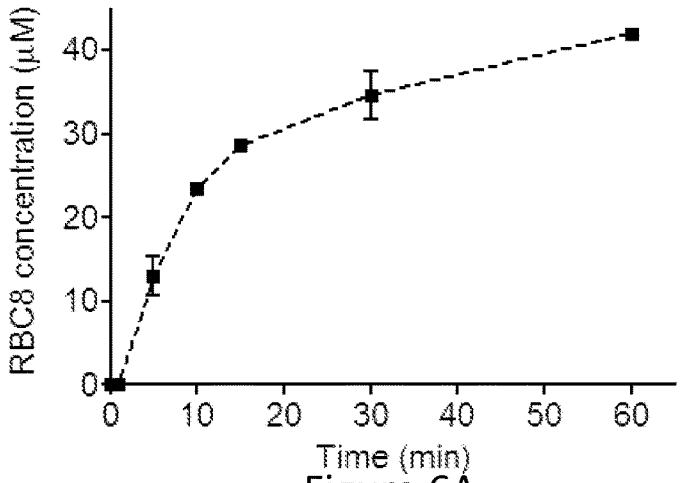
Figure 6B:
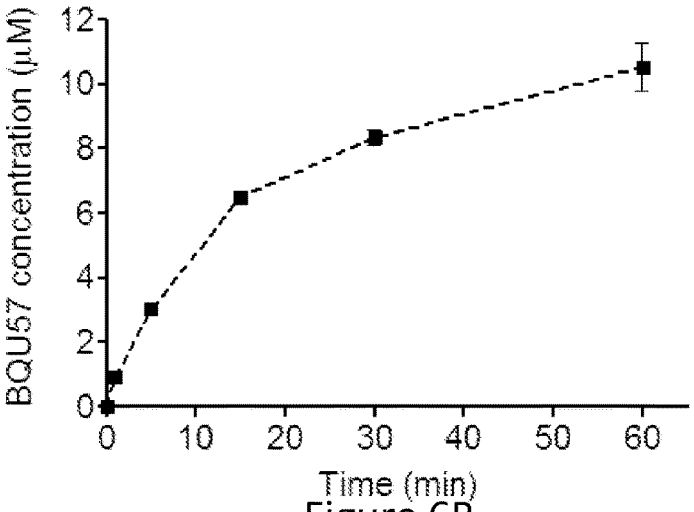
Figure 6C:
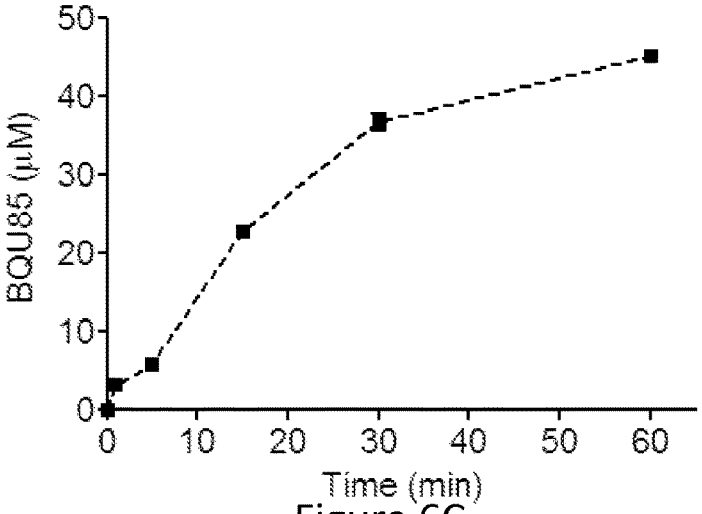
Figure 6E:
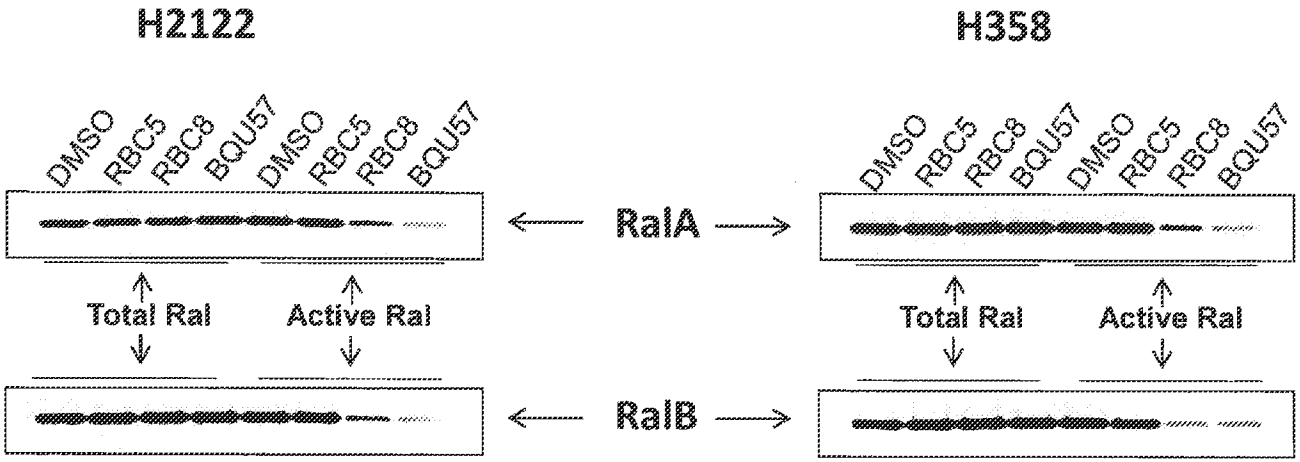

FIGS. 6A-6E show the cellular uptake of Ral inhibitors in vitro. H2122 human lung cancer cells were treated with 10 μM of RBC8 (FIG. 6A), BQU57 (FIG. 6B), BQU85 (FIG. 6C), and RBC5 (FIG. 6D). Cells were collected at different time points (1, 5, 15, 30 and 60 min), and drug concentrations in cells determined using LC/MS-MS methods (n=3 for each time point). FIG. 6E shows the inhibition of Ral activity in H2122 and H358 cells by RBC5, RBC8 and BQU57. Cells were grown under anchorage-independent conditions and treated with 10 μM compounds for 3 hours. Ral activity in cell lysates were then determined using the pull down assay with RalBP1 agarose beads. Data represent three independent experiments.

Figure 7A:
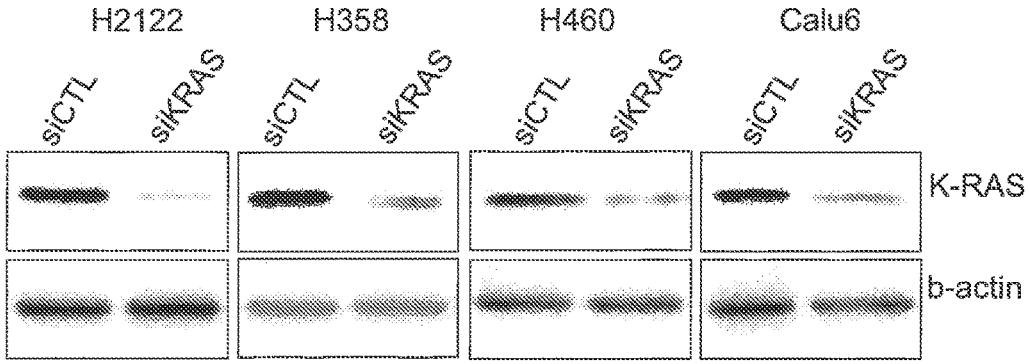
Figure 7B:
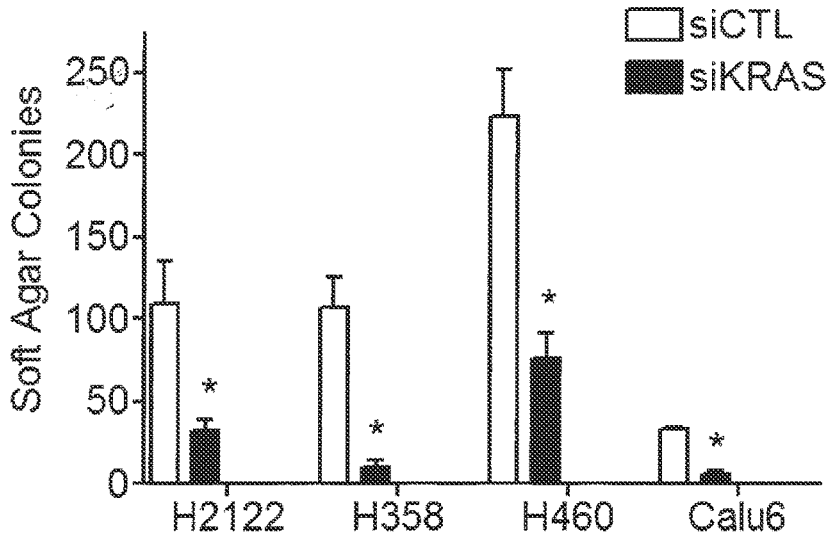
Figure 7C:
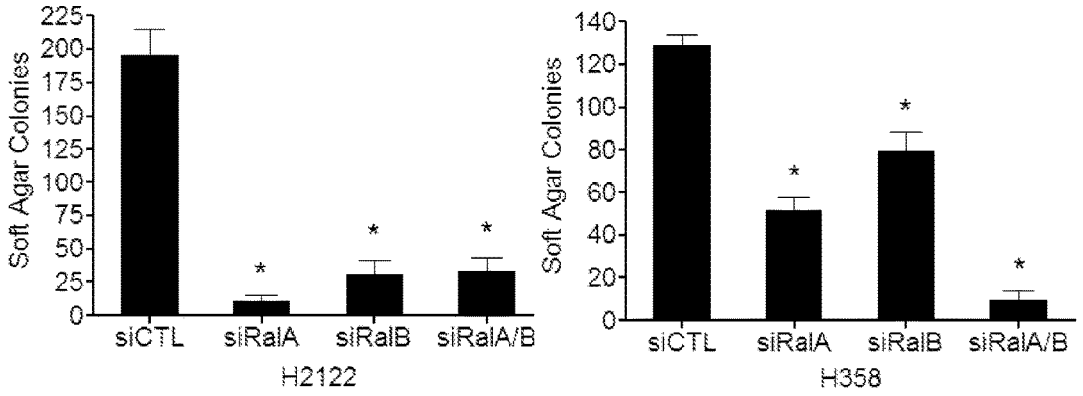
Figure 7D:
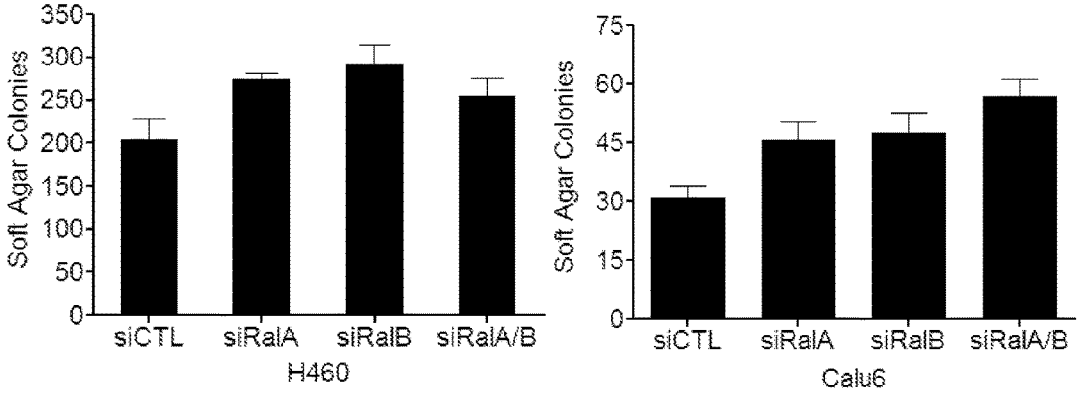
Figure 7E:
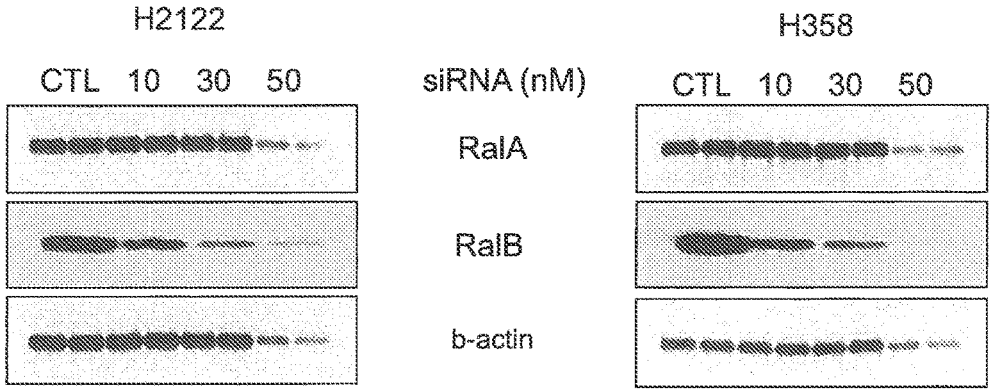
Figure 7F:
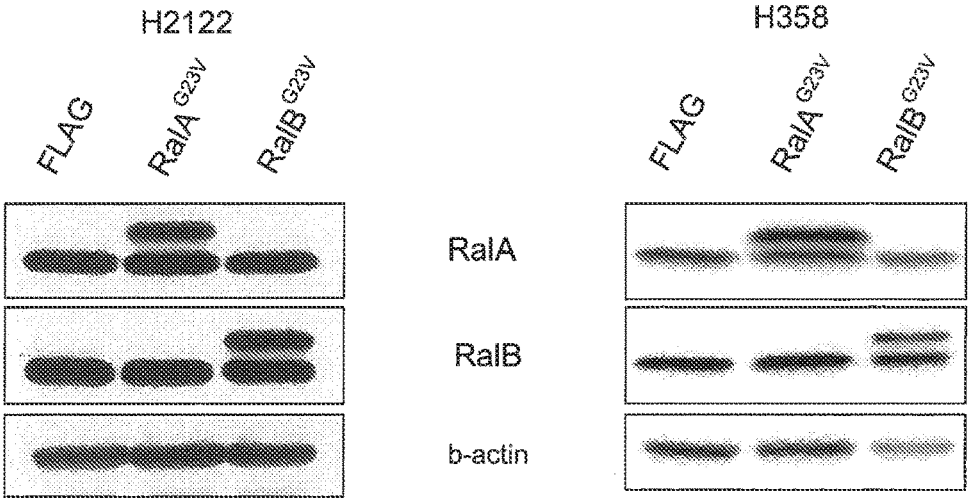

FIGS. 7A-7F show the effect of K-Ras or Ral knockdown or overexpression on anchorage-independent growth of four human lung cancer cell lines. FIG. 7A shows an immunoblot of siRNA knockdown of K-Ras in H2122, H358, H460, and Calu6 cell lines 48 h after siRNA transfection. FIG. 7B shows that all four lines were sensitive to K-Ras knockdown using the soft agar colony formation assay. The effect of Ral knockdown on anchorage-independent growth of four human lung cancer cell lines was investigated by transfecting the cells with siRNA against RalA, RalB or RalA/B for 48 h and then subjecting the cells to soft agar colony formation assays. FIG. 7C shows that cell lines H2122/H358 were sensitive to Ral knockdown. FIG. 7D shows that cell lines H460/Calu6 were not sensitive to Ral knockdown. FIG. 7E shows immunoblots of knockdown of both RalA and RalB in H2122 and H358 cell lines 48 h after treatment with various concentrations of siRNA. FIG. 7F shows immunoblots of successful overexpression of constitutively active $RalA^{G23V}$ and $RalB^{G23V}$ in H2122 and H358 cells. H2122 cells were transiently transfected with FLAG, FLAG-$RalA^{G23V}$ and FLAG-$RalB^{G23V}$ for 48 h. H358 cells stably overexpressing FLAG, FLAG-$RalA^{G23V}$ and FLAG-$RalB^{G23V}$ were generated by G418 selection.

DESCRIPTION OF EMBODIMENTS

Based on compelling clinical significance in tumor establishment and metastasis, the present inventors have identified and used Ral GTPases as molecular targets. As with all GTPases, activity of Ral is dependent upon cycling between an inactive (GDP-bound) and an active (GTP-bound) conformation. Active Ral proteins mediate downstream processes through their own set of effectors, including Ral Binding Protein 1 (RalBP1, RLIP76 or RIP1(37)), Sec5/Exo85, filamin, and phospholipase Dl. Thus, compounds that bind Ral-GDP and not Ral-GTP may be used to sterically inhibit effector binding and/or block conformational changes associated with the GTP bound state, leading to blockade of signal transmission with consequent decreased growth and apoptosis of Ral-dependent cancer cells. These compounds were identified using both virtual and physical screening of Ral GTPase inhibitors.

Figure 1A:
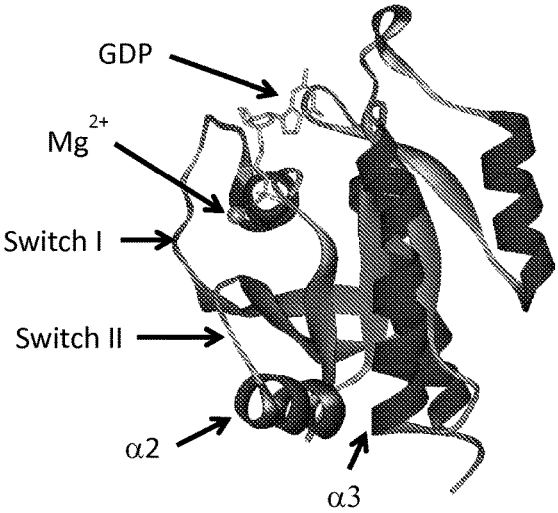
FIGS. 1A-1D show the molecular modeling of the target site on Ral protein. Structural model of RalA-GDP in ribbon (FIG. 1A) or surface (FIG. 1B) representations. The allosteric binding site is formed by switch II, helix α2 and helix α3. (C-D) Surface representations of RalA-GNP in complex with exo84 (FIG. 1C, exo84 not shown), and RalA-GNP in complex with sec5 (FIG. 1D, sec5 not shown).
Figure 1B:
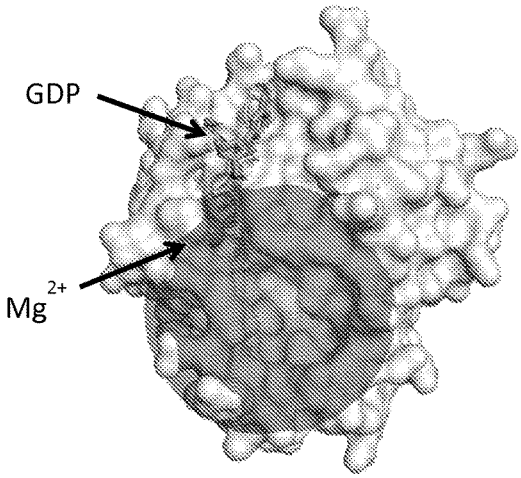
Figure 1C:
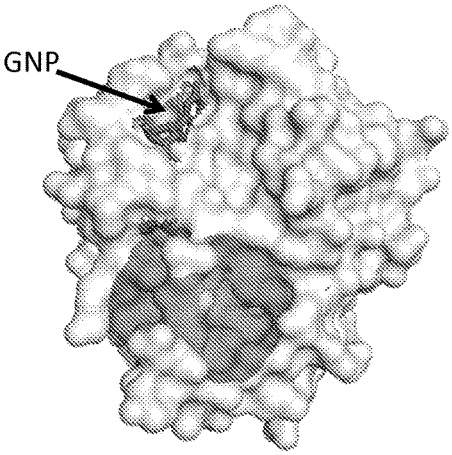
Figure 1D:
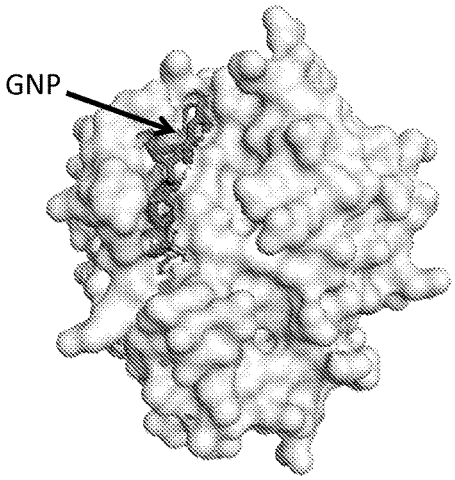

As noted above, Ral cycles between inactive (GDP-bound) and active (GTP-bound) forms. With the goal of finding compounds that preferentially bind to Ral-GDP (inactive) over Ral-GTP (active) and thereby stabilize Ral in the inactive state, the inventors inspected the three-dimensional structures of RalA in its active and inactive forms. This analysis revealed differences in the shape of a pocket near, but distinct from the nucleotide binding site (FIG. 1). This pocket (allosteric site) is similar to the previously described C3bot binding site and is made up by the switch-II region (Ral70-Ral77), helix α2 (Ral78-Ral85) and one face of helix α3 (FIG. 1A). The crystal structures used in the comparison included RalA-GDP (PDB code 2BOV (FIG. 1B) and RalA-GNP (non-hydrolysable form of GTP) in complex with exo84 (PDB code 1ZC4, FIG. 1C) or sec5 (PDB code 1UAD, FIG. 1D). Volumes calculated for each binding site were 175 $Å^3$ for RalA-GDP (FIG. 1B), 155 $Å^3$ for RalA-GNP-exo84 (FIG. 1C), and 116 $Å^3$ for RalA-GNP-sec5 (FIG. 1D). The RalB-GDP crystal structure is not published, but in the RalB-GNP structure (PDB code 2KE5, FIG. 1) this binding pocket is almost absent. Using a structure-based virtual screening approach to identify small molecules that bind to the allosteric site of RalA-GDP, 500,000 compounds were docked to the RalA-GDP pocket. The protein-ligand complexes were scored and sorted based on the calculated interaction energies followed by visual inspection of top candidates which led to the selection of 88 compounds. The 88 selected compounds were evaluated for their ability to inhibit RalA activation in living cells in culture using an ELISA for Ral activity based on selective binding of active RalA-GTP to its effector protein RalBP1.

RalA activity was also assayed independently by measuring lipid raft exocytosis during spreading of murine embryonic fibroblasts (MEFs) on fibronectin-coated coverslips. In these cells, siRNA depletion of RalA inhibits spreading, whereas caveolin (Cav1)–/– MEFs are resistant to RalA depletion.

TROSY $^{15}$N-HSQC (Transverse Relaxation-Optimized Heteronuclear Single Quantum Coherence) NMR was used to confirm the direct binding of the compounds to the Ral target site. The inventors focused on NMR structure of RalB in complex with GNP (the only structure that has been solved at this time). The $^{15}$N-HSQC NMR spectrum of RalB-GDP and RalB-GNP were first determined and the chemical shift difference was analyzed. NMR spectra were then recorded in the presence of RBC8 or DMSO control. Binding of small molecules to the protein was monitored by the perturbation of $^{15}$N-HSQC protein amide peaks. The 15N-HSQC spectrum of RalB-GDP (100 μM) in the absence and presence of 100 μM RBC8, showed changes in peak position of representative residues located in the allosteric site. RBC8 did not bind to RalB-GNP under the same conditions as indicated by minimal chemical shift changes on the NMR spectrum. Moreover, RBC5, which did not affect the level of active Ral in the cell-based ELISA assay, also did not induce chemical shift changes in RalB-GDP, therefore serving as additional negative control.

Based on all data including structural features, a series of RBC8 derivatives was synthesized and tested for binding in vitro. BQU57 was chosen for further evaluation because of its superior performance compared to RBC8 and its drug-like properties. A detailed NMR analysis of the binding between BQU57 and RalB-GDP was carried out. A plot of the chemical shift changes with BQU57 as a function of sequence showed that residues that exhibit significant changes are located in the switch-II (amino acid residues 70-77) and helix α2 (amino acid residues 78-85) region. Because no RalB-GDP crystal structure is available, a homology model was generated based on the similarity to RalA-GDP, and the residues that displayed chemical shift changes in response to the compounds were mapped onto this model. The majority of the chemical shift changes localized to the allosteric site, consistent with assignment of BQU57 binding to this site based on modeling. Similar to results with RBC8, BQU57 did not bind to RalB-GNP (100 μM) as indicated by minimal chemical shift changes on NMR spectrum. Analysis of the NMR chemical shift titrations revealed that binding of BQU57 was stoichiometric up to the apparent limiting solubility of the drug. The binding of BQU57 to RalB-GDP was also determined using Isothermal Titration calorimetry (ITC) and the results were similar to results from Surface Plasma Resonance (SPR).

The effects of RBC8 and BQU57 on human lung cancer cell growth were evaluated. Because Ral is well-known for its role in anchorage independence the inventors carried out growth inhibition assays in soft agar. Human lung cancer cells were used in a series of experiments to determine drug uptake, biologic specificity, and effect.

The cellular uptake of RBC8, BQU57, BQU85, and RBC5 was examined and all compounds were found to readily get into cells. All cell lines were found to be sensitive to K-Ras siRNA depletion but only H2122 and H358 were sensitive to Ral knockdown. Using this characteristic to determine the specificity of the compounds to Ral compared to Ras, a closely related GTPase, the inventors evaluated inhibition of colony formation in soft agar and found the Ral-dependent lines H2122 and H358 were sensitive. Additionally, a Ral pull-down assay using RalBP1 agarose beads showed that RBC8 and BQU57, but not RBC5, inhibited both RalA and RalB activation in both the H2122 and H358 cell lines. A chemo-genomic experiment was performed to further determine drug specificity to Ral. Treatment of H2122 and H358 cells that had siRNA knockdown of RalA and RalB with RBC8 or BQU57 did not result in significant further inhibition. Together, these data demonstrated RBC8 and BQU57 reduce anchorage independent growth via Ral inhibition.

The specificity of the compounds for the GDP form, compared to the GTP form of Ral, was evaluated by constitutively overexpressing the active form of RalAG23V or RalBG23V in H2122 and H358 cells. (The G23V mutation prevents RalGAP mediated activation of GTP hydrolysis and hence locks Ral in its active state.) Both RalAG23V and RalBG23V could rescue the growth inhibition effect of RBC8 and BQU57 compounds.

Inhibition of Ral activity and tumor growth were evaluated in human lung cancer mouse models. Pharmacokinetics of RBC8 and BQU57 were first analyzed in mice to test bioavailability, with RBC8 and BQU57 showing favorable properties that define good drug candidates, as shown in Table 1.

TABLE 1

Pharmacokinetic characteristics of selected compounds.

| | RBC8 | BQU57 |
|---|---|---|
| Dose (mg/kg) i.p. n = 3 | 50.0 | 50.0 |
| Co (μM) | 41.2 ± 4.2 | 41.6 ± 5.1 |
| $T_{1/2}$ (hr) | 0.58 ± 0.26 | 1.50 ± 0.11 |
| $AUC_{0\text{-}5\ hr}$ (mg · h/mL) | 139.6 ± 18.8 | 28.6 ± 2.1 |

Compound entry into tumor tissue was determined and substantial amounts of compound were detected in tumor tissue 3 hours post-dose.

The effect of the Ral inhibitors on xenograft tumor growth was then tested in nude mice. RBC8 inhibited tumor growth by the same order of magnitude as dual knockdown of RalA and RalB, and a second lung cancer line, H358 yielded similar results. BQU57 and BQU85 were also tested in vivo and dose-dependent growth inhibition effects were observed.

Ral GTPase activity was evaluated in vivo in the H2122 xenografts. RalBP1 pull-down measurements of Ral activity showed significant inhibition of both RalA and RalB by RBC8 and BQU57. Importantly, BQU57-induced dose-dependent inhibition of Ral activity correlated with inhibition of tumor growth. Additionally, Ras and RhoA activity was measured in BQU57 treated tumors and no significant inhibition was observed, further demonstrating the selectivity of the Ral inhibitors of the invention.

Hence, the present invention provides Ral GTPase inhibiting compounds. These compounds can bind to the inactive form of Ral protein and prevent GEF-induced activation or GTP exchange and are selective against Ral with little off target effects. Thus, the Ral GTPase inhibitors of this disclosure can be used to block the associated conformational change of Ral proteins upon GTP binding, thus preventing effector engagement and downstream signaling.

Thus, the present invention also provides methods of inhibiting the growth and/or metastasis of cancer in a subject by inhibiting a Ral GTPase in the subject. In a preferred embodiment, the Ral GTPase is at least one of the RalA and the RalB paralogs. The term "paralog" is used in this disclosure to denote genes in an organism that have been duplicated to occupy different positions in the same genome.

In another aspect, the invention provides a method of inhibiting the growth and/or metastasis of cancer in a subject by administering at least one compound of the invention, or pharmaceutically-acceptable salts thereof to the subject.

As used herein, the term "compound" means a chemical or biological molecule such as a simple or complex organic molecule, a peptide, a protein or an oligonucleotide.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Pharmaceutically-acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without excessive toxicity, irritation, allergic response, or other problems or complications, commensurate with a reasonable benefit/risk ratio.

Pharmaceutically-acceptable salt forms of compounds provided herein are synthesized from the compounds of the invention which contain a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in at page 1418 of Remington's Pharmaceutical Sciences, 17th ed., Mack Publishing Company, Easton, Pa., 1985.

The term "subject" refers to mammals such as humans or primates, such as apes, monkeys, orangutans, baboons, gibbons, and chimpanzees. The term "subject" can also refer to companion animals, e.g., dogs and cats; zoo animals; equids, e.g., horses; food animals, e.g., cows, pigs, and sheep; and disease model animals, e.g., rabbits, mice, and rats. The subject can be a human or non-human. The subject can be of any age. For example, in some embodiments, the subject is a human infant, i.e., post natal to about 1 year old; a human child, i.e., a human between about 1 year old and 12 years old; a pubertal human, i.e., a human between about 12 years old and 18 years old; or an adult human, i.e., a human older than about 18 years old. In some embodiments, the subject is an adult, either male or female.

The term "therapeutically-effective amount" or "therapeutic amount" of a compound of this invention means an amount effective to inhibit the formation or progression of cancer following administration to a subject having a cancer.

The term "solvate" refers to the compound formed by the interaction of a solvent and a compound. Suitable solvates are pharmaceutically acceptable solvates, such as hydrates, including monohydrates and hemi-hydrates.

It will be appreciated by those skilled in the art that compounds of the invention having a chiral center may exist in, and may be isolated in, optically active and racemic forms. It is to be understood that the compounds of the present invention encompass any racemic, optically-active, regioisomeric or stereoisomeric form, or mixtures thereof, which possess the therapeutically useful properties described herein. Where the compounds of the invention have at least one chiral center, they may exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diasteromers by standard techniques, such as the formation of stereoisomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers and enantiomers thereof are encompassed within the scope of the present invention.

It is well known in the art how to prepare optically active forms (for example, by resolution of the racemic form by recrystallization techniques, by synthesis from optically-active starting materials, by chiral synthesis, or by chromatographic separation using a chiral stationary phase). It is also to be understood that the scope of this invention encompasses not only the various isomers, which may exist but also the various mixtures of isomers, which may be formed. The resolution of the compounds of the present invention, their starting materials and/or the intermediates may be carried out by known procedures, e.g., as described in the four volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981, which is incorporated in its entirety by this reference. Basically, the resolution of the compounds is based on the differences in the physical properties of diastereomers by attachment, either chemically or enzymatically, of an enantiomerically pure moiety resulting in forms that are separable by fractional crystallization, distillation or chromatography.

The chemicals used in combination with the compounds of the present invention to make the pharmaceutical compositions of the present invention may be purchased commercially. The compounds of the present invention, including the salts of these compounds, may be prepared in ways well known to those skilled in the art of organic synthesis. The compounds of the invention may be prepared using the reactions performed in solvents appropriate to the reagents and materials employed and suitable for the transformation being effected. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

The pharmaceutical compositions of the invention contain one or more compounds of the invention and a pharmaceutically-acceptable carrier, which are media generally accepted in the art for the delivery of biologically active agents to animals, in particular, subjects. Pharmaceutically-acceptable carriers are formulated according to a number of factors well within the purview of those of ordinary skill in the art to determine and accommodate. These include, without limitation: the type and nature of the active agent being formulated; the subject to which the agent-containing composition is to be administered; the intended route of administration of the composition; and, the therapeutic indication being targeted. Pharmaceutically-acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically-acceptable carriers, and factors involved in their selection, are found in a variety of readily available sources, such as Remington's Pharmaceutical Sciences, 17th ed., Mack Publishing Company, Easton, Pa., 1985.

This invention further provides methods of treating a subject afflicted with a cancer or preventing the metastasis of such cancer in a subject, which includes administering to the subject a pharmaceutical composition provided herein. Such compositions generally comprise a therapeutically effective amount of a compound of the invention in an amount effective to prevent, ameliorate, lessen or inhibit the cancer. Such amounts typically comprise from about 0.1 to about 100 mg of the compound per kilogram of body weight of the subject to which the composition is administered. Therapeutically effective amounts can be administered according to any dosing regimen satisfactory to those of ordinary skill in the art.

Administration may be, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffering agents. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as, but not limited to, lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

A preferred formulation of the invention is a mono-phasic pharmaceutical composition suitable for parenteral or oral administration for the prevention, treatment or prophylaxis of a cancer, consisting essentially of a therapeutically-effective amount of a compound of the invention, and a pharmaceutically acceptable carrier.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn may depend upon crystal size and crystalline form. Alternatively, delayed absorption of a parenterally-administered drug is accomplished by dissolving or suspending the drug in an oil vehicle.

Injectable depot forms are made by forming microencapsulated matrices of the drug in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the therapeutic compounds of the present invention.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of compounds of this invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required.

The ointments, pastes, creams and gels may contain, in addition to an active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical formulations include those suitable for administration by inhalation or insufflation or for nasal or intraocular administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more of the anti-cancer compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Typical atomizers are the Mistometer (Wintrop) and Medihaler (Riker).

Drops, such as eye drops or nose drops, may be formulated with an aqueous or nonaqueous base also comprising one or more dispersing agents, solubilizing agents or suspending agents. Liquid sprays are conveniently delivered from pressurized packs. Drops can be delivered by means of a simple eye dropper-capped bottle or by means of a plastic bottle adapted to deliver liquid contents drop-wise by means of a specially shaped closure.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The dosage formulations provided by this invention may contain the therapeutic compounds of the invention, either alone or in combination with other therapeutically active ingredients, and pharmaceutically acceptable inert excipients. The term 'pharmaceutically acceptable inert excipients' includes at least one of diluents, binders, lubricants/glidants, coloring agents and release modifying polymers.

Suitable antioxidants may be selected from amongst one or more pharmaceutically acceptable antioxidants known in the art. Examples of pharmaceutically acceptable antioxidants include butylated hydroxyanisole (BHA), sodium ascorbate, butylated hydroxytoluene (BHT), sodium sulfite, citric acid, malic acid and ascorbic acid. The antioxidants may be present in the dosage formulations of the present invention at a concentration between about 0.001% to about 5%, by weight, of the dosage formulation.

Suitable chelating agents may be selected from amongst one or more chelating agents known in the art. Examples of suitable chelating agents include disodium edetate (EDTA), edetic acid, citric acid and combinations thereof. The chelating agents may be present in a concentration between about 0.001% and about 5%, by weight, of the dosage formulation.

The dosage form may include one or more diluents such as lactose, sugar, cornstarch, modified cornstarch, mannitol, sorbitol, and/or cellulose derivatives such as wood cellulose and microcrystalline cellulose, typically in an amount within the range of from about 20% to about 80%, by weight.

The dosage form may include one or more binders in an amount of up to about 60% w/w. Examples of suitable binders include methyl cellulose, hydroxypropyl cellulose, hydroxypropylmethyl cellulose, polyvinyl pyrrolidone, eudragits, ethyl cellulose, gelatin, gum arabic, polyvinyl alcohol, pullulan, carbomer, pregelatinized starch, agar, tragacanth, sodium alginate, microcrystalline cellulose and the like.

Examples of suitable disintegrants include sodium starch glycolate, croscarmellose sodium, crospovidone, low substituted hydroxypropyl cellulose, and the like. The concentration may vary from 0.1% to 15%, by weight, of the dosage form.

Examples of lubricants/glidants include colloidal silicon dioxide, stearic acid, magnesium stearate, calcium stearate, talc, hydrogenated castor oil, sucrose esters of fatty acid, microcrystalline wax, yellow beeswax, white beeswax, and the like. The concentration may vary from 0.1% to 15%, by weight, of the dosage form.

Release modifying polymers may be used to form extended release formulations containing the therapeutic compounds of the invention. The release modifying polymers may be either water-soluble polymers, or water insoluble polymers. Examples of water-soluble polymers include polyvinylpyrrolidone, hydroxy propylcellulose, hydroxypropyl methylcellulose, vinyl acetate copolymers, polyethylene oxide, polysaccharides (such as alginate, xanthan gum, etc.), methylcellulose and mixtures thereof. Examples of water-insoluble polymers include acrylates such as methacrylates, acrylic acid copolymers; cellulose derivatives such as ethylcellulose or cellulose acetate; polyethylene, and high molecular weight polyvinyl alcohols.

Also encompassed by the present invention are methods for screening potential therapeutic agents that may prevent, treat or inhibit the metastasis of lung cancer, by inhibiting a Ral GTPase comprising: (a) combining a Ral GTPase and a potential therapeutic compound under conditions in which they interact, and; (b) monitoring the enzymatic activity of the Ral GTPase; wherein a potential therapeutic compound is selected for further study when it inhibits the enzymatic activity compared to a control sample to which no potential therapeutic compound has been added. In one embodiment, the potential therapeutic compound is selected from the group consisting of a pharmaceutical agent, a cytokine, a small molecule drug, a cell-permeable small molecule drug, a hormone, a combination of interleukins, a lectin, a bispecific antibody, and a peptide mimetic.

One embodiment of the invention relates to a compound of the invention for use in the treatment or prevention of cancer, or a metastasis of a cancer, in a subject. A related embodiment of the invention relates to a composition of the invention for use in the treatment or prevention of cancer, or a metastasis of a cancer, in a subject.

Another embodiment of the invention relates to the use of any of the compounds or compositions of the invention in the preparation of a medicament for the inhibition of the growth or metastasis of a cancer in a subject.

Each publication or patent cited herein is incorporated herein by reference in its entirety.

EXAMPLES

The following examples are provided to illustrate certain aspects, embodiments, and configurations of the disclosure and are not to be construed as limitations on the disclosure, as set forth in the appended claims.

Example 1—Molecular Modeling of Ral Inhibitors

Molecular modeling was used to find compounds that preferentially bind to Ral-GDP (inactive) over Ral-GTP (active) with the expectation that such molecules will stabilize the inactive state. Inspection of three-dimensional structures of RalA in its active and inactive forms revealed differences in the shape of a pocket near but distinct of the nucleotide binding site (FIG. 1). This pocket (allosteric site) is similar to the previously described C3bot binding site and is made up by the switch-II region (Ral70-Ral77), helix α2 (Ral78-Ral85) and one face of helix α3 (FIG. 1A). The crystal structures used in the comparison included RalA-GDP (PDB code 2BOV, FIG. 1B) and RalA-GNP (non-hydrolysable form of GTP) in complex with exo84 (PDB code 1ZC4, FIG. 1C) or sec5 (PDB code 1UAD, FIG. 1D). Volumes calculated for each binding site were 175 Å3 for RalA-GDP (FIG. 1B), 155 Å3 for RalA-GNP-exo84 (FIG. 1C), and 116 Å3 for RalA-GNP-sec5 (FIG. 1D). The RalB-GDP crystal structure is not published, but in the RalB-GNP structure (PDB code 2KE5, FIG. 1) this binding pocket is almost absent.

We followed a structure-based virtual screening approach to identify small molecules that bind to the allosteric site of RalA-GDP. The crystallographic coordinates of the 2.66 Å human RalA-GDP (PDB: 2BOV), RalA-GNP in complex with exo84 (PDB: 1ZC4), RalA-GNP in complex with sec5 (PDB: 1UAD) crystal structures were obtained from the RCSB Protein Data Bank (rcsb.org). AutoDock4 was used for the initial library screening. The ChemDiv library [v2006.5, 500,000 compounds excluding those possessing reactive groups, known ADME/toxicity, physicochemical properties lie outside 'drug-likeness' parameters (Lipinski's rule of 5 and Veber's Rule of 2) at pH 7] was downloaded from ZINC database and docked into the identified site on RalA-GDP using rigid docking protocols. Ligand molecules were assigned Gasteiger charges and polar hydrogen atoms by the ligand preparation module provided in the AutoDockTools. The Lamarckian genetic algorithm in AutoDock4 was used to evaluate ligand binding energies over the conformational search space. Protein-ligand complexes were scored and sorted based on the calculated interaction energies followed by visual inspection of top candidates which led to selection of 88 compounds.

Example 2—Cell-Based Functional Assays

The 88 selected compounds were evaluated for their ability to inhibit RalA activation in living cells in culture.

Human bladder cancer cell line J82 and lung cancer cell lines H2122, H358, H460, and Calu6 were obtained from ATCC. Antibodies used are against human RalA (BD Biosciences, #610222), RalB (Millipore #04-037), and FLAG tag (Novagen #71097). Activity assay kits for Ras (#BK008) and RhoA (#BK036) were obtained from Cytoskeleton (Denver, Colo.). We used an ELISA for Ral activity based on selective binding of active RalA-GTP to its effector protein RalBP1.

J82 cells stably overexpressing FLAG-RalA were plated 800,000 cells per well in 6-well plates and allowed to incubate for 16 h. Cells were treated with 500 μl of fresh medium containing test compounds (50 μM) or DMSO control (1 h; 37° C.). Cells were then washed with ice-cold PBS and collected into ice-cold lysis buffer (750 μl containing 50 mM Tris, pH 7.5, 200 mM NaCl, 1% Igepal ca-630, 10 mM MgCl2, and protease inhibitors). The lysate was cleared by centrifugation and the supernatants were then flash-frozen and stored at −80° C. until testing. For the ELISA assay, HisGrab nickel coated 96-well plate strips (Pierce, #15142) were washed three times with ELISA buffer (200 μl consisting of 50 mM Tris, pH 8.0, 150 mM NaCl, 0.5% Tween 20, and 10 mM MgCl2). RalBP1 (0.5 μg/100 μl) was then added to the wells and incubated with rocking (2 h RT). The plates were then washed three times with 200 μl ELISA buffer. The plates were placed on ice and lysates, or lysis buffer control (100 μl), were added to the wells in quadruplicate. The plates were then incubated overnight with rocking at 4° C. followed by two washes with ice-cold ELISA buffer. Mouse anti-FLAG (Sigma, F1804) antibody (1:20,000 in ELISA buffer) was then added at 100 μl per well and incubated (1 h, 4° C.). After three washes, goat anti-mouse antibody conjugated to HRP (Pierce, #31430) (1:2,500) was added at 100 μl per well and incubated (1 h, 4° C.). HRP substrate (Vector Laboratories, #SK-4400) was added to each well at 100 μl after three washes and incubated for 1 h at RT. The reactions were stopped by adding sulfuric acid (100 μl, 2N). Absorbance was read at OD450 on a Biotek Synergy H1 plate reader (BioTek Instruments, Inc., Winooski, Vt.); Absorbance was corrected for background absorbance by subtracting the reading for the same well at OD540.

The J82 human bladder cancer cells stably expressing FLAG-tagged RalA improved protein detection over that provided by anti-Ral antibodies. This afforded an enhanced dynamic range to the assay. The amount of bound RalA was proportional to the relative activation state.

An independent approach was used to assess RalA activity, which is required for lipid raft exocytosis during spreading of murine embryonic fibroblasts (MEFs) on fibronectin-coated coverslips. Briefly, wild type or caevolin−/− mouse embryonic fibroblasts were starved for 24 h, detached from culture plates with Accutase (Innovative Cell Technologies Inc., San Diego, Calif.), resuspended in DMEM with 0.2% serum and 0.5% methyl cellulose, and held in suspension (90 min, 37° C.). While in suspension, cells were treated with inhibitor (50 μM or DMSO control, 1 h). After treatment, cells were rinsed once with DMEM containing 0.2% serum and equal numbers of cells from all treatments were added to 24-well plates that had been coated overnight (4° C., 2 μg/mL human fibronectin). Cells were allowed to spread for 30 min and then fixed with formaldehyde using standard protocols. To enable visualization, cells were labeled with Lava Cell (Active Motif) and visualized on a Nikon TE300 fluorescence microscope. Three distinct regions of each well were imaged and cell spread area was quantitated using ImageJ (NIH).

In these cells, siRNA depletion of RalA inhibits spreading, whereas caveolin (Cav1)−/− MEFs are resistant to RalA depletion. siRNA against human RalA and RalB or both were obtained from Dharmacon (Boulder, Colo.) using published sequences.

Example 3—In Vitro Binding Assays

To confirm the direct binding of the compounds to the target, we used TROSY 15N-HSQC (Transverse Relaxation-Optimized Heteronuclear Single Quantum Coherence) NMR. RalB (Q72L mutant) in a pET16b (Novagen) plasmid was a kind gift from Dr. Darerca Owen (Cambridge University). RalB was purified with additional steps for loading with GDP or the non-hydrolyzable form of GTP, GMPNPP (GNP, Sigma-Aldrich). Uniform $^{13}C^{15}N$-double labeled protein was produced in M9 media supplemented with 15N—NH4Cl and 13C-glucose. Samples were prepared for NMR in 50 mM sodium phosphate, pH 7.6, 100 mM NaCl and 1 mM MgCl2. All NMR experiments were recorded on an Agilent 900 MHz system at 25° C. Resonance assignments for the RalB-GNP complex were obtained from previously published studies deposited in Biological Magnetic Resonance Bank (BMRB, code: 15230). Chemical shift assignments of the RalB-GDP complex were obtained independently using HNCACB, CBCA(CO)NH and COCNH-TOCSY experiments. All NMR data was processed using NMRPipe and analyzed using CCPNMR analysis program. Assignment were obtained by automated assignment using PINE followed by manual verification. $^{15}N$-HSQC experiments were used to monitor amide shifts from the RalB protein (100 μM) following the addition of compound reconstituted in deuterated DMSO. DMSO concentrations in the final sample were 0.5% or 1%; control samples were made with 0.5% or 1% deuterated DMSO and all samples containing compounds were compared to their corresponding DMSO control.

Because only the NMR structure of RalB in complex with GNP has been solved (PDB code 2KE5, BMRB entry 15230), we focused on this isoform. The $^{15}N$-HSQC NMR spectrum of RalB-GDP and RalB-GNP were first determined and the chemical shift differences were analyzed. NMR spectra were then recorded in the presence of RBC8 or DMSO control. Binding of small molecules to the protein was monitored by the perturbation of $^{15}N$-HSQC protein amide peaks. The $^{15}N$-HSQC spectrum of RalB-GDP (100 μM) in the absence and presence of 100 μM RBC8 showed changes in peak position of representative residues located in the allosteric site. On the other hand, RBC8 did not bind to RalB-GNP under the same conditions as indicated by minimal chemical shift changes on the NMR spectrum.

Based on all data including structural features, a series of RBC8 derivatives was synthesized and tested for binding in vitro. We chose BQU57 and BQU85 for further evaluation because of superior performance compared to RBC8 and drug-like properties (FIG. 3A, FIG. 2).

Figure 2A:
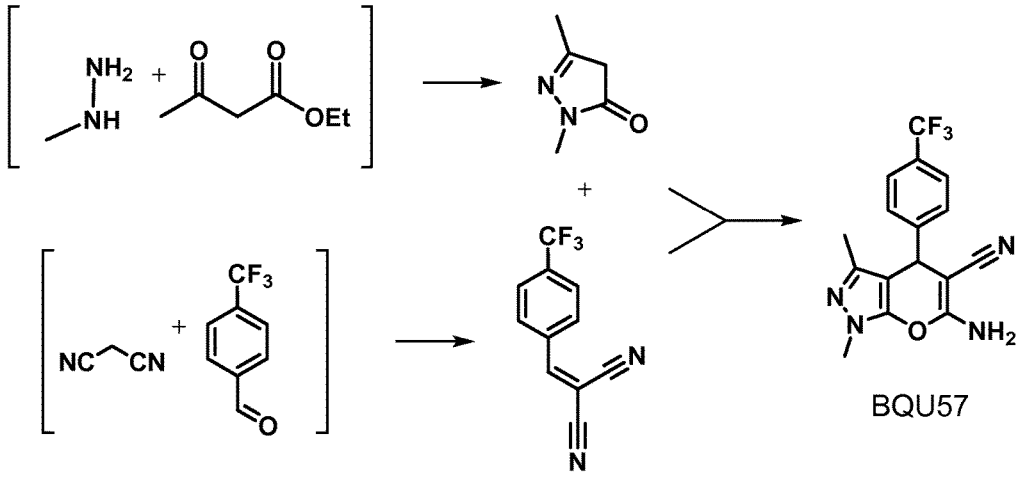
FIG. 2A shows the chemical synthesis schemes for compounds BQU57 and BQU85. Figure S3B-D shows the characterization of BQU57 binding to Ral.
Figure 2A:
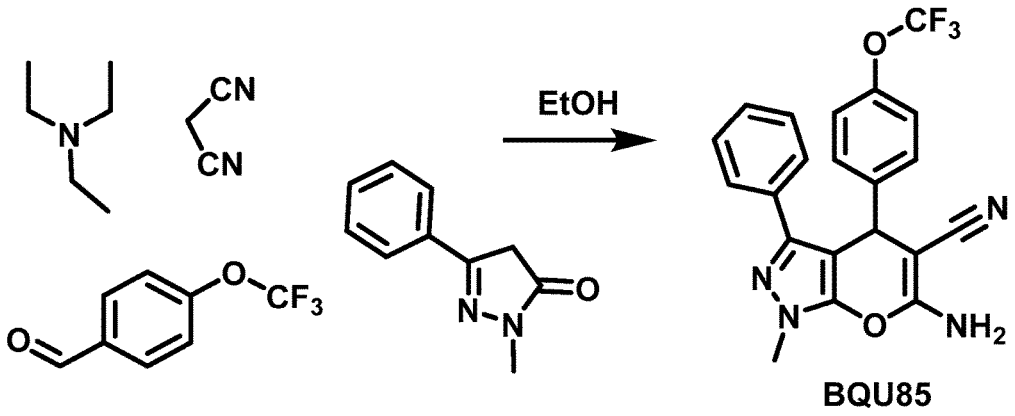
Figure 3A:
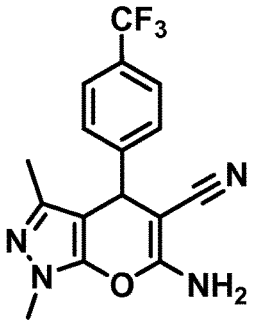
FIGS. 3A-3E show the characterization of compounds binding to Ral.

The synthesis schemes for compounds BQU57 and BQU85 are shown in FIG. 2A.

A. 6-amino-1,3-dimethyl-4-(4-(trifluoromethyl)phenyl)-1,4-dihydropyrano[2,3-c]pyrazole-5-carbonitrile (BQU57)

4-(Trifluoromethyl)benzaldehyde (500 mg, 2.87 mmol), malononitrile (190 mg, 2.87 mmol) and triethylamine (400 μL mL, 2.87 mmol) in ethanol (10 mL) was stirred for 1.0 min and then 1H-Pyrazol-5(4H)-one (321 mg, 2.87 mmol) and added, capped and stirred at room temperature (22 hr) and then concentrated and purified by chromatography ($SiO_2$; 2% MeOH in methylene chloride) to afford BQU57 (445 mg, 1.33 mmol, 46% yield) as a yellow solid. $^1H$-NMR (400 MHz) DMSO-$D_6$: 7.28 (s, 4H), 7.10 (brs, 2H), 4.64 (s, 1H), 3.57 (s, 3H), 1.64 (s, 3H); $^{13}C$-NMR (100 MHz) DMSO-$D_6$: 160.1, 147.6, 144.7, 143.9, 142.9, 129.9, 122.3, 121.4, 120.6, 96.2, 58.2, 36.8, 33.9, 12.8.

B. 6-amino-1-methyl-3-phenyl-4-(4-(trifluoromethoxy)phenyl)-1,4-dihydropyrano[2,3-c]pyrazole-5-carbonitrile (BQU085)

A mixture of the 4-(trifluoromethoxy)benzaldehyde (0.327 g, 1.72 mmol, 1.0 equ.), malononitrile (0.114 g, 1.72 mmol, 1.0 equ.) and triethylamine (0.240 mL, 1.72 mmol, 1.0 equ.) in ethanol (6.0 mL) was stirred for 10 min, followed by the addition of 1H-Pyrazol-5(4H)-one (0.300 g, 1.72 mmol). The reaction mixture was concentrated after 22 h and purified by column chromatography on $SiO_2$ (2% methanol in dichloromethane) to give BQU_03_85 (174 mg, 0.421 mmol, 25%) as yellow solid. $^1H$-NMR (400 MHz) DMSO: 7.47-7.45 (d, 2H), 7.26-7.24 (d, 2H), 7.20-7.14 (m, 7H), 5.08 (s, 1H), 3.76 (s, 3H); $^{13}C$-NMR (100 MHz) DMSO: 159.3, 147.4, 146.0, 144.7, 144.1, 133.1, 129.8, 128.6, 128.0, 126.5, 121.7, 121.2, 120.4, 95.3, 59.3, 37.4, 34.5.

Figure 2B:
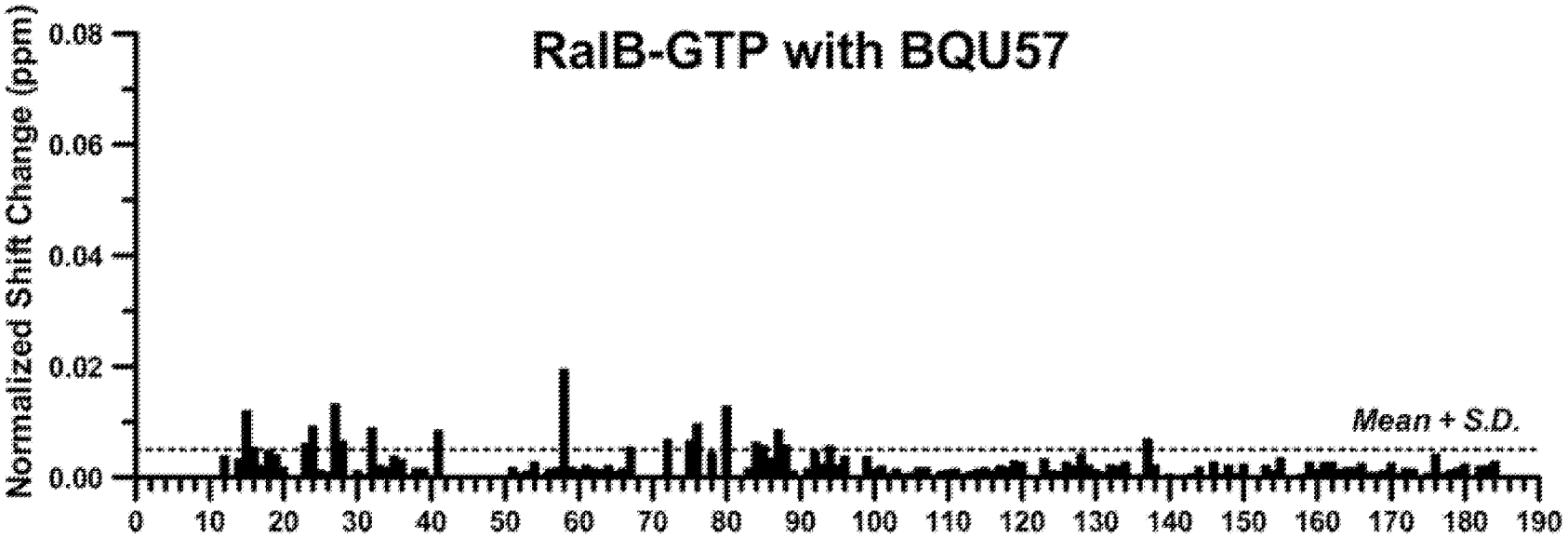
FIG. 2B shows the chemical shift changes in RalB-GNP (100 μM) in the presence of 100 μM BQU57.
Figure 3B:
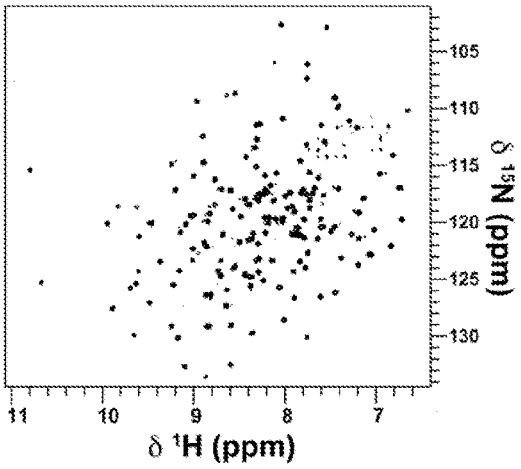
Figure 3C:
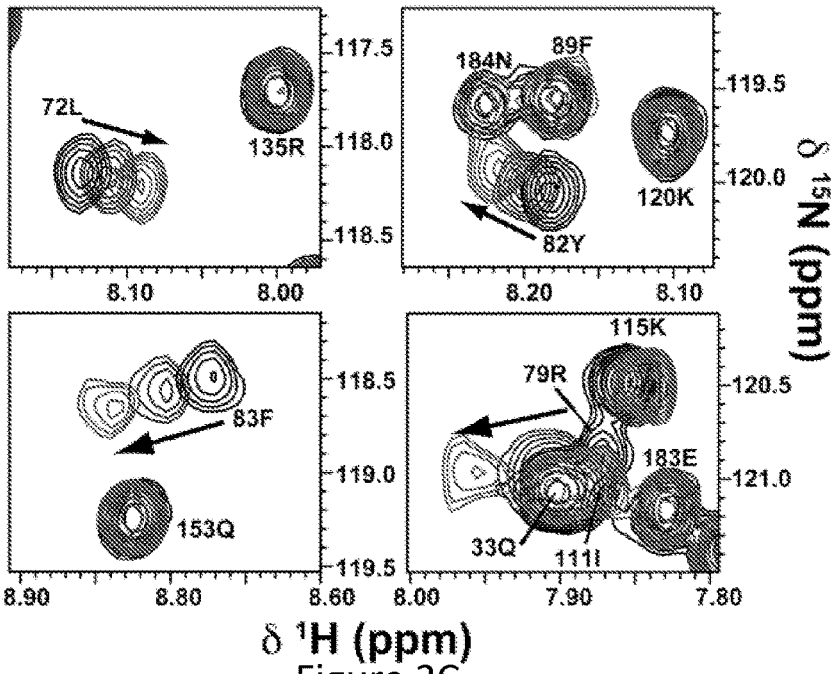
Figure 3D:
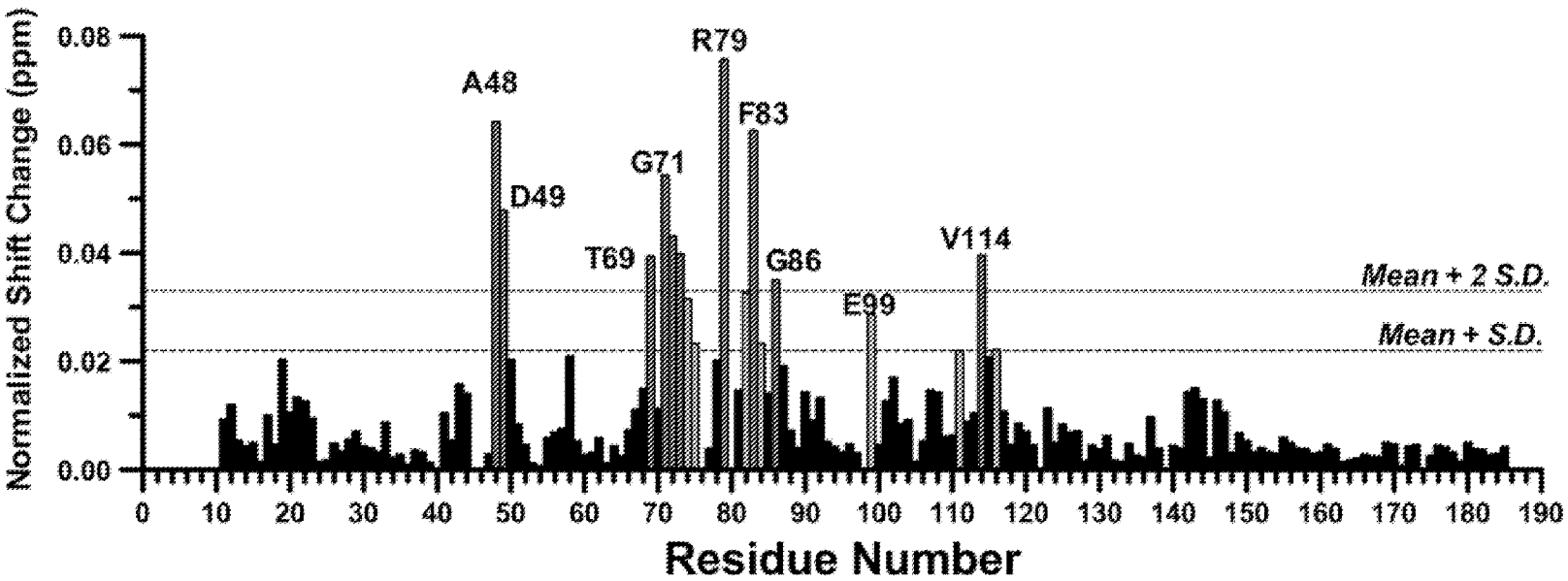
Figure 3E:
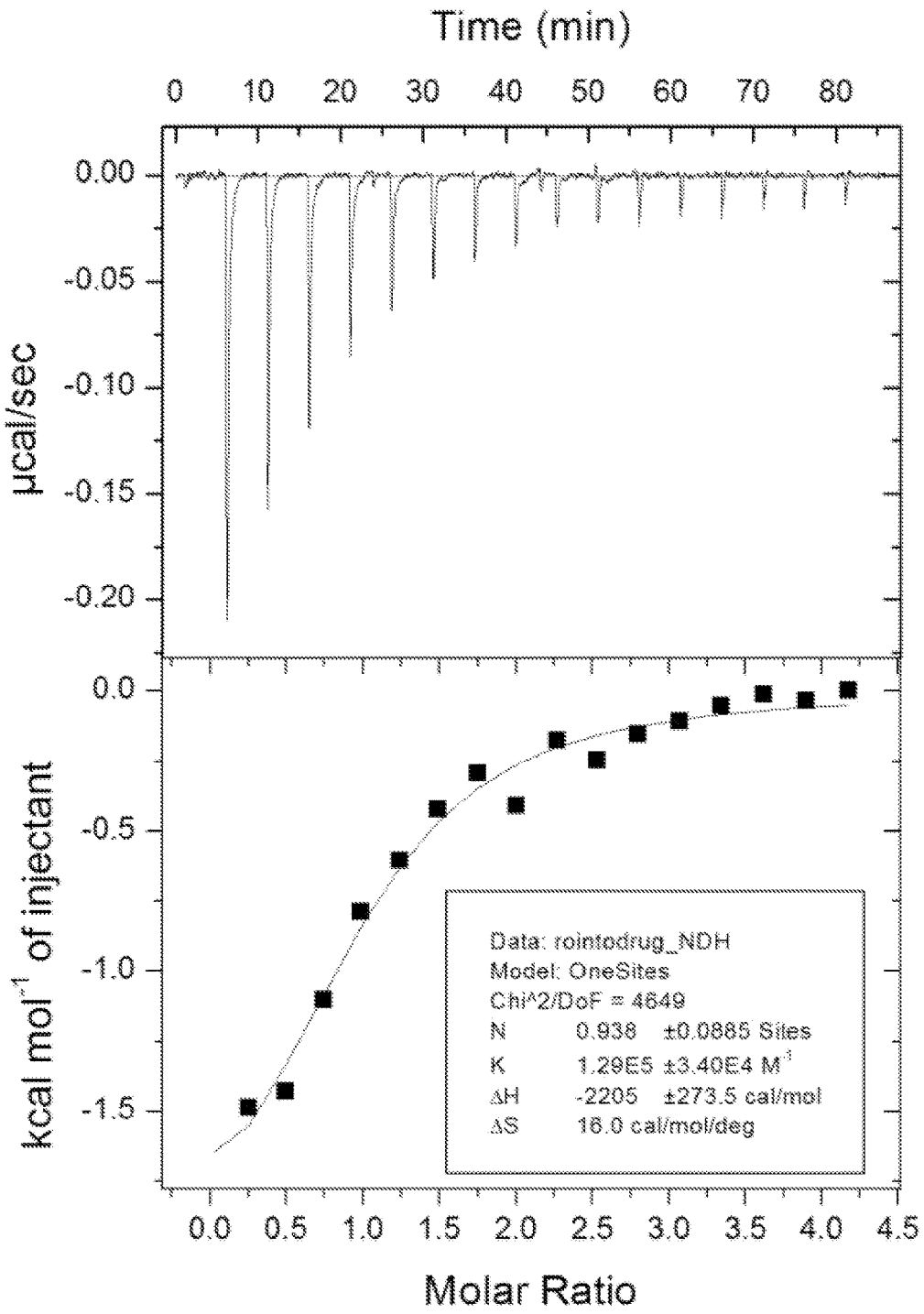

A detailed NMR titration of the binding between BQU57 and RalB-GDP was carried out. The NMR spectrum of RalB-GDP (100 μM) in the absence (black) and presence (magenta) of 100 μM BQU57 is shown in FIG. 3B. Representative residues that experience dose-dependent chemical shift changes are shown in FIG. 3C. A chemical shift change map with 100 μM of BQU57 was generated (FIG. 3D) and most of the residues that exhibited significant chemical shift changes (highlighted bars) were located to the switch-II (aa 70-77) and helix α2 (aa 78-85) region. In the absence of a crystal structure of RalB-GDP, a homology model was generated based on the sequence similarity to RalA-GDP and the residues that experienced chemical shift changes in the presence of drug was mapped onto this model (FIG. 3E). This shows that the majority of the chemical shift changes localize to the allosteric site, and confirm that BQU57 is binding to the predicted site. Similar to RBC8, BQU57 (100 μM) did not bind to RalB-GNP (100 μM) as indicated by minimal chemical shift changes on the NMR spectrum (FIG. 2B).

Figure 2C:
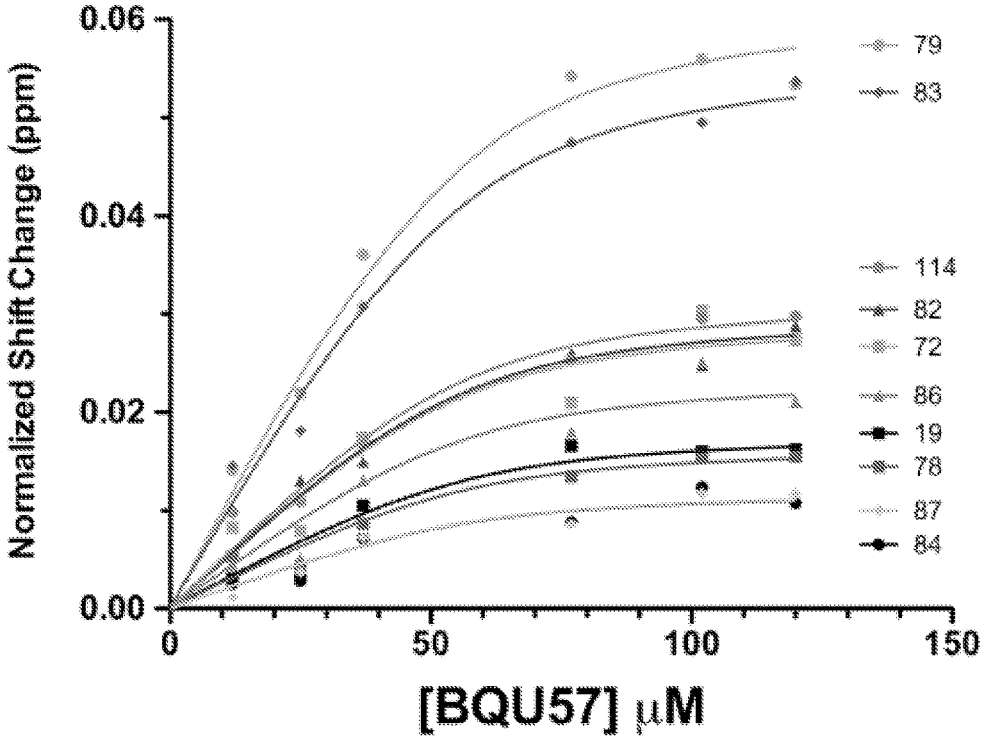
FIG. 2C shows the plot of 1H-15N-HSQC NMR chemical shift changes of selected residues in RalB-GDP with increasing concentrations of BQU57. Surface plasmon resonance determination of KD for binding between BQU57 and RalB-GDP showed a fitted binding curve giving a KD value of 4.7 μM.

Analysis of the NMR chemical shift titrations revealed that binding of BQU57 was stoichiometric up to the apparent limiting solubility of the drug (estimated as approx. 75 μM in control experiments without protein) (FIG. 2C). Consequently the binding of BQU57 to RalB-GDP was then determined using Isothermal Titration calorimetry (ITC). ITC experiments were carried out using the MicroCal iTC200 system. Both protein and drug were prepared in 50 mM sodium phosphate, pH 7.6, 100 mM NaCl, and 1 mM $MgCl_2$. Final DMSO concentration was adjusted to 1%. RalB-GDP protein (500 μM) were loaded into the syringe and titrated into drug (25 μM) or buffer alone as control. All experiments were carried out at 25° C. ITC yielded a $K_D$=7.7±0.6 μM (FIG. 3F). This result was confirmed by Surface Plasma Resonance (SPR). SPR experiments were carried out using the Biacore 3000 system. Running buffer: PBS, pH 7.4, 1 μM GDP, 2 mM $MgCl_2$, 3% DMSO. Regeneration buffer: PBS, pH 7.4, 1 μM GDP, 2 mM $MgCl_2$. RalB protein was immobilized on CM5 chip; samples of compound BQU57 in running buffer were injected at 30

μL/min for 60 s contact time followed by 5 minute regeneration. SPR gave a $K_D$ of 4.7±1.5 μM despite low sensitivity of the assay.

Differential scanning fluorometry (DSF) was used to evaluate binding between compounds and RalB-GDP. The melting temperature was measured by monitoring the increase of SYPRO orange that binds to hydrophobic regions of the protein. DSF was performed by preparing a plate containing 10 μM RalB-GDP and 10 μM RalB-GPNPP, 4×SYPRO orange in 20 mM Tris PH 8.0, 200 mM NaCl, 2.5 mM $MgCl_2$ and 1 mM DTT buffer. Test compound was added to each well ensuring that the final concentration of DMSO was 1% across all samples. The thermal melting curves were obtained on a Light cycler 480 (Roche). The melting temperature was obtained by normalizing the curves and obtaining the temperature at the midpoint of the transition curve. DSF confirmed dose-dependent binding between BQU57 and RalB-GDP, and also demonstrated nucleotide-dependence.

Example 4—Effects on In Vitro Human Cancer Cell Growth

The effects of RBC8 and BQU57 on human lung cancer cell growth were evaluated. Because Ral is well-known for its role in anchorage independence, we carried out growth inhibition assays in soft agar. Four human lung cancer cells H2122, H358, H460 and Calu6 were used in a series of experiments to determine drug uptake, biologic specificity and effect. To measure growth inhibition of human lung cancer cells under anchorage-independent conditions in soft agar, cells were seeded into 6-well plates (coated with a base layer made of 2 ml of 1% low-melting-point agarose) at 15,000 cells per well in 3 ml of 0.4% low-melting-point agarose containing various concentration of drug. Two to four weeks (depending on cell line) after incubation, cells were stained with 1 mg/ml MTT and colonies were counted under a microscope. The IC50 values were defined as the concentration of drug that resulted in 50% reduction in colony number compared to DMSO treated control.

For growth effects induced by siRNA treatment, cells were transfected with 50 nM siRNA against RalA, RalB or both (RalA/B) using methods and sequences described 10. After 72 hrs, cells were subjected to the soft agar colony formation assay.

For the chemo-genetic experiments, siRNA treated cells were seeded into soft agar in the presence of various concentrations of drug. For the overexpression experiments, H358 cells stably overexpressing FLAG, FLAG-RalAG23V or FLAG-RalBG23V were generated and cells were subjected to the soft agar colony formation assay in the presence of drug. Attempts to stably overexpress FLAG-RalAG23V or FLAG-RalBG23V in H2122 cells were unsuccessful and the rescue experiments with H2122 were carried out 72 hrs after the transient transfection with FLAG, FLAG-RalAG23V or FLAG-RalBG23V using the soft agar colony formation assay in the presence of drug.

To quantitate how well the test compounds get into cells, H2122 human lung cancer cells were seeded at $3\times10^5$ cells per well in 6-well plates and let sit for 16 h. Compounds (10 μM) were individually dosed in triplicate; cells were then collected into 500 μl ice-cold ACN:MeOH:$H_2$0 (1:1:1) at different time points (1, 5, 15, 30 and 60 min). Drug concentrations in cell lysates were then determined using LC/MS-MS methods as described with respect to the pharmacokinetic and pharmacodynamic studies in mice, described in detail in Example 5, below.

Testing cellular uptake of RBC8, BQU57, and BQU85 showed that all drugs readily get into cells (FIG. 6). To confirm that Ral activity is inhibited in H2122 and H358 cells by drug treatment, we performed the Ral activity pull-down assay. Cells were treated with drug for 3 hrs, collected and Ral activity measured using the RalBP1 pull-down assay kit (Millipore #14-415). RBC8 and BQU57 but not RBC5 inhibited both RalA and RalB activity in both cell lines (FIG. 6E).

Additionally, all lines were found to be sensitive to K-Ras siRNA depletion (FIG. 7A, 7B) but only H2122 and H358 were sensitive to Ral knockdown (FIG. 7C, 7D). Using this characteristic to determine the specificity of the compounds to Ral compared to Ras, a closely related GTPase, we evaluated inhibition of colony formation in soft agar and noted the Ral-dependent lines H2122 and H358 but not in H460 or Calu6 cells were sensitive (FIG. 4A, B, K). The IC50 for RBC8 is 3.5 μM in H2122 and 3.4 μM in H358; for BQU57 2.0 μM in H2122 and 1.3 μM in H358. Next a chemo-genomic experiment was performed to further determine drug specificity to Ral. Treatment of H2122 and H358 cells that had siRNA knockdown of RalA and RalB with RBC8 or BQU57 did not result in significant further inhibition (FIGS. 4C-4F, FIG. 7E). Together, this data suggest RBC8, BQU57, and BQU85 reduce anchorage independent growth via Ral inhibition.

To address the specificity of the compounds for the GDP compared to the GTP form of Ral, we overexpressed constitutively active forms of RalAG23V or RalBG23V in H2122 and H358 cells. The G23V mutation prevents RalGAP mediated activation of GTP hydrolysis and hence locks Ral in its active state 30. We found that both RalAG23V and RalBG23V could rescue the growth inhibition effect of the compounds (FIGS. 4G-4J, FIG. 7F).

Example 5—Pharmacokinetics, Pharmacodynamics and Tumor Growth In Vivo

Inhibition of Ral activity and tumor growth were evaluated in human lung cancer mouse models. Pharmacokinetics (PK) of RBC8 and BQU57 were first analyzed in nude mice to test bioavailability. Following a single intraperitoneal injection (50 mg/Kg), blood samples were collected at time intervals from 0 to 5 h post-dose (9 time points). Pharmacokinetic parameters including area under the curve (AUC), Cmax, and t½ were estimated using non-compartmental methods by LC-MS/MS and showed favorable properties that define good drug candidates (see Table 1, supra).

We next determined compound entry into tumor tissue. To do so, athymic nude mice (Ncr nu/nu; National Cancer Institute, Fredrick, Md.) were received at 5 to 6 weeks of age and were allowed to acclimate for 2 weeks in sterile micro isolator cages with constant temperature and humidity. Mice had free access to food and water. H2122 cells in log-phase growth were harvested on the day of use. Cells were suspended in un-supplemented RPMI 1640 medium and 0.1 mL ($2\times10^5$ cells) was injected s.c. four sites per mice. For H358 xenografts, cells ($5\times10^6$) were mixed with matrigel (20% final concentration) and 0.1 mL was inoculated s.c. per site. After cell inoculation, mice were monitored daily, weighed twice weekly and caliper measurements begun when tumors visible. Tumor volume was calculated by (L×W2)/2, where L is longer measurement of tumor and W is the smaller tumor measurement. Drug treatment started the day after inoculation. Compounds were dissolved in DMSO and injected i.p. daily except weekends at 10/20/50 mg/kg. No obvious toxicities were observed in the control (DMSO) or drug-treated animals as assessed by difference in body weight between control and drug-treated animals taking tumor size into account. As shown in FIG. 5A, B, G substantial amounts of compound were detected in tumor tissue 3 h post-dose. The effect of the Ral inhibitors on xenograft tumor growth was then tested in nude mice. Mice were inoculated subcutaneously with H2122 human lung cancer cells and treated intraperitoneally with 50 mg/kg/d (except weekends) of RBC8 24 h post inoculation. RBC8 inhibited tumor growth (FIG. 5C-D) by the same order of magnitude as dual knockdown of RalA and RalB (FIG. 5E), and a second lung cancer line, H358 yielded similar results. BQU57 and BQU85 were also tested in vivo at several different doses (5, 10, 20, and 50 mg/kg/d) and dose-dependent growth inhibition effects were observed (FIGS. 5F,5H).

Finally, we evaluated Ral GTPase activity in vivo in the H2122 xenografts. Nude mice were inoculated with $5\times10^6$ cells H2122 cells s.c. at four sites per mice. Tumor size reached an average of 250 $mm^3$ in ten days, at which time mice were given a signal i.p. dose of RBC8 or BQU57 at various concentrations. Tumors were then collected 3 h after injection of RBC8 or BQU57. RalA and RalB activity in tumor samples were then measured using the RalBP1 pull-down assay kit (Millipore #14-415). Ras and RhoA activity in tumor samples were measured using the respective pull-down assay kits. All the activity assays used western blotting as the final readout. For quantification of the immunoblots, the bands on each blot were first normalized to their respective internal control (10 ng of recombinant Ral, Ras, or Ral protein run in the last lane) the numbers were then compared across different blots, each of which represented one treatment condition. Mice bearing H2122 tumors (median size 250 $mm^3$) were given a single intraperitoneal dose of RBC8 (50 mg/kg) or BQU57 (10/20/50 mg/kg) and tumors collected 3 h post-dose. RalBP1 pull-down measurements of Ral activity showed significant inhibition of both RalA and RalB by RBC8 and BQU57. Importantly, BQU57-induced dose-dependent inhibition of Ral activity correlated with inhibition of tumor growth, and Ras and RhoA activity was also measured in BQU57 treated tumors and no significant inhibition was observed, further demonstrating the selectivity of these Ral inhibitors.

Example 6—Synthesis of Compounds of the Invention

Compounds of the invention were synthesized according to the following synthesis scheme and materials.

Compound Synthesis Scheme

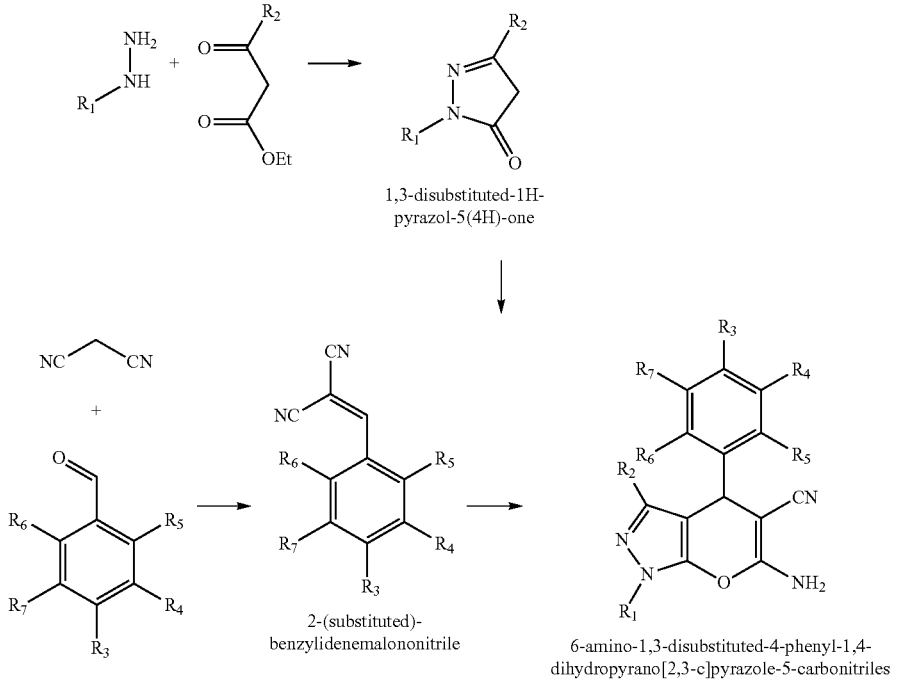

| Compound Number | R1 | R2 | R3 | R4 | R5 | R6 | R7 |
|---|---|---|---|---|---|---|---|
| 1 | Ph | Me | — | — | — | — | — |
| 2 | Ph | Me | — | — | — | — | — |
| 3 | Me | Ph | — | — | — | — | — |
| 4 | Ph | Ph | — | — | — | — | — |
| 5 | $CH_2$—Ph | Ph | — | — | — | — | — |
| 6 | Me | m,p-DiOMe-Ph | — | — | — | — | — |
| 7 | Ph | m,p-DiOMe-Ph | — | — | — | — | — |
| 8 | Ph | p-OMe-Ph | — | — | — | — | — |
| 9 | Me | p-OMe-Ph | — | — | — | — | — |
| 10 | Me | Me | H | H | H | H | H |

-continued

| | | | | | | | |
|---|---|---|---|---|---|---|---|
| 11 | Me | Ph | H | H | H | H | H |
| 12 | Ph | Me | H | H | H | H | H |
| 13 | Ph | Ph | H | H | H | H | H |
| 14 | Ph | p-OMe-Ph | H | H | H | H | H |
| 15 | Me | p-OMe-Ph | H | H | H | H | H |
| 16 | Me | m,p-diOMe-Ph | H | H | H | H | H |
| 17 | Me | Me | F | H | H | H | H |
| 18 | Ph | Me | F | H | H | H | H |
| 19 | Me | Ph | F | H | H | H | H |
| 20 | Ph | Ph | F | H | H | H | H |
| 21 | Me | m,p-diOMe-Ph | F | H | H | H | H |
| 22 | Ph | p-OMe-Ph | F | H | H | H | H |
| 23 | Ph | m,p-diOMe-Ph | F | H | H | H | H |
| 24 | Me | p-OMe-Ph | F | H | H | H | H |
| 25 | Me | Me | H | F | H | H | F |
| 26 | Me | Ph | H | F | H | H | F |
| 27 | Ph | Me | OMe | H | H | H | H |
| 28 | Me | Me | OMe | H | H | H | H |
| 29 | Me | Ph | OMe | H | H | H | H |
| 30 | Ph | Ph | OMe | H | H | H | H |
| 31 | Ph | p-OMe-Ph | OMe | H | H | H | H |
| 32 | Me | p-OMe-Ph | OMe | H | H | H | H |
| 33 | Me | Me | OMe | F | H | H | H |
| 34 | Me | Me | OMe | H | OMe | OMe | H |
| 35 | Me | Ph | OMe | F | H | H | H |
| 36 | Me | Me | CF3 | H | H | H | H |
| 37 | Me | Ph | CF3 | H | H | H | H |
| 38 | Me | Me | O—$CF_3$ | H | H | H | H |
| 39 | Me | Ph | O—$CF_3$ | H | H | H | H |
| 40 | Me | Me | CN | H | H | H | H |
| 41 | Me | Ph | CN | H | H | H | H |
| 42 | Me | Me | $CH(CH3)_2$ | H | H | H | H |
| 43 | Me | Ph | $CH(CH_3)_2$ | H | H | H | H |
| 44 | Me | Me | O—$CH_2$— | $CH_2$—O— | H | H | H |
| 45 | Me | Ph | O—$CH_2$— | $CH_2$—O— | H | H | H |
| 46 | Me | Me | N: | H | H | H | H |
| 47 | Me | Ph | N: | H | H | H | H |
| 48 | Me | Me | H | N: | H | H | H |
| 49 | Me | Ph | H | N: | H | H | H |
| 50 | Me | Me | H | Br | N: | H | H |
| 51 | Me | Ph | H | Br | N: | H | H |
| 52 | Me | Me | imidazole | H | H | H | H |
| 53 | Me | Ph | imidazole | H | H | H | H |

Materials and Methods

Anisaldehyde, benzaldehyde, 1,4-benzodioxan-6-carboxaldehyde, benzyl-hydrazine, 6-bromo-2-pyridincarboxaldehyde, deuterated chloroform ($CDCl_3$), deuterated dimethyl sulfoxide (DMSO-$d_6$), 3,5-difluorobenzaldehyde, ethyl acetoacetate, ethyl benzoylacetate, ethyl 3,4-dimethoxybenzoylacetate, ethyl-hydrocupreine hydrochloride, ethyl-4-methoxybenzoylacetate, 4-fluorobenzaldehyde, 3-fluoro-4-methoxybenzaldehyde, 4-formylbenzonitrile, 4-isopropylbenzaldehyde, 4-(1H-imidazol-1-yl)benzaldehyde, malononitrile, methyl-hydrazine, phenyl-hydrazine, 3-pyridincarboxaldehyde, sodium ethoxide, trimethylamine (TEA), 2,4,6-trimethoxybenzaldehyde, and 4-(trifluoromethoxy)benzaldehyde were purchased from Sigma-Aldrich Chemical Company (St. Louis, Mo.). Ethyl acetate (EtOAc), HPLC grade methanol (MeOH), HPLC grade acetonitrile (ACN), HPLC grade water ($H_2O$), formic acid, ammonium acetate, hexanes and methylene chloride (DCM) were obtained from Fisher Scientific (Pittsburgh, Pa.). Ethanol was purchased from Decon Laboratories, Inc. (King of Prussia, Pa.). Silica Gel 60 Å 40-63 μm was purchased from Sorbent Technologies (Norcross, Ga.).

The $^1H$ and $^{13}C$ NMR spectra were recorded using a 400 MHz Bruker NMR, Avance III 400. The chemical shifts are reported in ppm. An Applied Biosystems Sciex 4000 (Applied Biosystems; Foster City, Calif.) which was equipped with a Shimadzu HPLC (Shimadzu Scientific Instruments, Inc.; Columbia, Md.) and Leap auto-sampler (LEAP Technologies; Carrboro, N.C.) was used. Liquid chromatography employed an Agilent Technologies, Zorbax extended-C18 50×4.6 mm, 5 micron column at 40° C. with a flow-rate of 0.4 mL/min. The mobile phase consisted of A: 10 mM ($NH_4OAc$), 0.1% formic acid in $H_2O$, and B: 50:50 ACN:MeOH. The chromatography method used was 95% A for 1.0 min; ramped to 95% B at 3.0 min and held for 4.5 min, lastly, brought back to 95% A at 8.5 min and held for 1.0 min (9.5 min total run time). Synthesized compounds were monitored via electro-spray ionization positive ion mode (ESI+) using the following conditions: i) an ion-spray voltage of 5500 V; ii) temperature, 450° C.; iii) curtain gas (CUR; set at 10) and Collisionally Activated Dissociation (CAD; set at 5) gas were nitrogen; iv) Ion Source gas one (GS1) and two (GS2); v) entrance potential was set at 10 V; vi) quadruple one (Q1) and (Q3) were set on Unit resolution; vii) dwell time was set at 200 msec; and viii) declustering potential (DP), collision energy (CE), and collision cell exit potential (CXP) are voltages (V). Samples (10 μL) were analyzed by LC/MS-MS. As judged by NMR and LC/MS-MS analysis, all purified compounds were >97% pure.

Synthesis:

3-methyl-1-phenyl-1H-pyrazol-5(4H)-one (1)

A solution of ethyl acetoacetate (9.02 mL, 71.2 mmol) in EtOH (130 mL) was treated at 0° C. with phenyl-hydrazine (7.00 g, 64.7 mmol). The mixture was allowed to slowly warm to ambient temperature and then heated to 60° C. (3 h). The solvent was removed under vacuum and the residue purified by column chromatography on silica gel (EtOAc: hexanes; 1:1) to give 1 (7.60 g, 43.6 mmol, 67% yield) as a light yellow powder. $^1$H-NMR (400 MHz) $CDCl_3$: 7.87-7.85 (d, 2H), 7.41-7.37 (t, 2H), 7.19-7.16 (t, 1H), 3.42 (s, 2H), 2.19 (s, 3H), $^{13}$C-NMR (100 MHz) $CDCl_3$: 170.5, 156.2, 138.0, 128.8, 125.0, 118.8, 43.0, 17.0; LC/MS-MS: 175.0→77.1 m/z; GS1 and GS2 at 30, DP=56, CE=25, CXP=4, $t_R$=3.52 min.

1,3-dimethyl-1H-pyrazol-5(4H)-one (2)

Ethyl acetoacetate (15.1 mL, 119 mmol) in EtOH (200 mL) was treated at 0° C. with methyl-hydrazine (5.00 g, 109 mmol). The mixture was allowed to slowly warm to ambient temperature and then heated to 60° C. (3 h). The solvent was removed under vacuum and the residue purified by column chromatography on silica gel (EtOAc:hexanes; 1:1) to afford 2 (8.02 g, 71.5 mmol, 66% yield) after purification by crystallization (DCM and hexanes) as a white off solid. $^1$H-NMR (400 MHz) $CDCl_3$: 3.25 (s, 3H), 3.16 (s, 2H), 2.08 (s, 3H), $^{13}$C-NMR (100 MHz) $CDCl_3$: 172.2, 155.4, 138.0, 41.3, 31.0, 16.8. LC/MS-MS: 113.2→82.0 m/z; GS1 and GS2 at 30, DP=61, CE=25, CXP=4, $t_R$=2.9 min.

1-methyl-3-phenyl-1H-pyrazol-5(4H)-one (3)

Ethyl benzoylacetate (18.4 mL, 95.5 mmol) in EtOH (180 mL) was treated at 0° C. with methyl-hydrazine (4.57 mL, 86.8 mmol.). The mixture was allowed to slowly warm to ambient temperature and then heated to 60° C. (3 h). The solvent was removed under vacuum and the residue purified by column chromatography on silica gel (EtOAc:hexanes; 1:1) to give 3 (11.0 g 63.1 mmol, 73% yield) after purification by crystallization (ethanol) as a light yellow solid. $^1$H-NMR (400 MHz) $CDCl_3$: 7.67-7.65 (m, 2H), 7.42-7.41 (m, 3H), 3.60 (s, 2H), 3.41 (s, 3H), $^{13}$C-NMR (100 MHz) $CDCl_3$: 171.8, 154.2, 131.0, 130.3, 128.8, 125.6, 37.9, 31.4. LC/MS-MS: 175.0→77.2 m/z; GS1 and GS2 at 30, DP=66, CE=43, CXP=4, $t_R$=3.45 min.

1,3-diphenyl-1H-pyrazol-5(4H)-one (4)

Ethyl benzoylacetate (12.2 mL, 71.2 mmol) in EtOH (130 mL) was treated at 0° C. with phenyl-hydrazine (7.00 g, 71.2 mmol.). The mixture was allowed to slowly warm to ambient temperature and heated to 60° C. (3 h). The solvent was removed under vacuum and the residue purified by column chromatography on silica gel (EtOAc:hexanes; 1:4) and crystallization (EtOH) to give 4 as an off-white solid (6.75 g, 28.6 mmol, 44% yield). $^1$H-NMR (400 MHz) DMSO: 11.8 (s, 1H), 7.84-7.82 (d, 4H), 7.50-7.40 (m, 4H), 7.34-7.27 (m, 2H), 6.02 (s, 1H), $^{13}$C-NMR (100 MHz) DMSO: 154.2, 150.0, 139.3, 133.8, 129.3, 129.0, 128.2, 126.1, 125.5, 121.5, 85.5; LC/MS-MS: 237.0→77.1 m/z; GS1 and GS2 at 30, DP=81, CE=68, CXP=4, $t_R$=4.15 min.

1-benzyl-3-phenyl-1H-pyrazol-5(4H)-one (5)

A solution of ethyl benzoylacetate (4.80 mL, 28.2 mmol) in EtOH (60 mL) was treated at 0° C. with benzyl-hydrazine (5.00 g, 25.6 mmol). The mixture was slowly warmed to ambient temperature and heated to 60° C. (16 h). The reaction mixture was concentrated and diluted with EtOH (100 mL) and then 3.0 g of sodium ethoxide added and stirred (40 h). The solid was filtered off and the solvent removed in vacuo. The residue was purified by column chromatography on silica gel (4:1 hexanes:EtOAc to 100% EtOAc) to give 5 (25.5 mg, 1.02 mmol, 4% yield) as a light orange solid. $^1$H-NMR (400 MHz) DMSO: 11.2 (s, 1H), 7.71-7.70 (d, 2H), 7.37-7.31 (m, 4H), 7.27-7.20 (m, 4H), 5.85 (s, 1H), 5.13 (s, 2H), $^{13}$C-NMR (100 MHz) DMSO: 153.6, 148.6, 138.3, 134.4, 128.8, 128.7, 127.6, 127.5, 125.1, 83.7, 50.0; LC/MS-MS: 251.1→91.1 m/z; GS1 and GS2 at 30, DP=2, CE=33, CXP=14, $t_R$=4.01 min.

3-(3,4-dimethoxyphenyl)-1-methyl-1H-pyrazol-5 (4H)-one (6)

Ethyl 3,4-dimethoxybenzoylacetate (5.00 g, 19.8 mmol) in EtOH (60 mL) was treated at 0° C. with methyl-hydrazine (0.95 mL, 19.8 mmol, 1.0 equiv.). The mixture was allowed to slowly warm to ambient temperature and heated to 60° C. (3 h). The solvent was removed under vacuum and the residue purified by chromatography on silica gel (hexanes: EtOAc; 4:1 to 1:1) to 6 (1.86 g, 7.94 mmol, 44% yield) as a light yellow powder. $^1$H-NMR (400 MHz) $CDCl_3$: 7.35-7.35 (d, 1H), 7.06-7.04 (dd, 1H), 6.87-6.85 (d, 1H), 3.94 (s, 3H), 3.92 (s, 3H), 3.57 (s, 2H), 3.39 (s, 3H); $^{13}$C-NMR (100 MHz) $CDCl_3$: 171.6, 154.1, 151.1, 149.4, 124.1, 119.6, 110.7, 107.3, 55.9, 55.9, 38.0, 31.3; LC/MS-MS: 235.1→219.0 m/z; GS1 and GS2 at 30, DP=66, CE=33, CXP=14, $t_R$=3.26 min.

3-(3,4-dimethoxyphenyl)-1-phenyl-1H-pyrazol-5 (4H)-one: (7)

Ethyl 3,4-dimethoxybenzoylacetate (3.00 g, 11.9 mmol.) in EtOH (60 mL) was treated at 0° C. with phenyl-hydrazine (1.17 mL, 10.8 mmol.). The mixture was allowed to slowly warm to ambient temperature and heated to 60° C. (3 h). The solvent was removed under vacuum and the residue purified by chromatography on silica gel (hexanes:EtOAc; 4:1 to 1:1) to afford 7 (920 mg, 2.32 mmol, 22% yield) after purification by crystallization (EtOH) as a yellow powder. $^1$H-NMR (400 MHz) $CDCl_3$: 8.00-7.97 (d, 1H), 7.48-7.42 (m, 3H), 7.25-7.21 (t, 1H), 7.17-7.14 (dd, 1H), 6.91-6.89 (d, 1H), 3.98 (s, 3H), 3.95 (s, 3H), 3.83 (s, 2H); $^{13}$C-NMR (100 MHz) $CDCl_3$: 170.1, 154.4, 151.4, 149.4, 138.1, 128.8, 125.2, 123.8, 120.1, 119.1, 110.7, 107.6, 56.0, 56.0, 39.7; LC/MS-MS: 297.0→218.2 m/z; GS1 and GS2 at 30, DP=96, CE=37, CXP=18, $t_R$=3.98 min.

3-(4-methoxyphenyl)-1-phenyl-1H-pyrazol-5(4H)-one (8)

Ethyl-4-methoxybenzoylacetate (7.00 g, 27.8 mmol) in EtOH (100 mL) was treated at 0° C. with phenyl-hydrazine (2.50 mL, 25.3 mmol). The mixture was allowed to slowly warm to ambient temperature and heated to 60° C. (3 h). The solvent was removed under vacuum and the residue purified by chromatography on silica gel (hexanes:EtOAc; 4:1 to 1:1) to afford 3-(4-methoxyphenyl)-1-phenyl-1H-pyrazol-5 (411)-one (8; 5.21 g, 19.6 mmol, 78% yield) after crystallization (EtOH) as a light yellow solid. $^1$H-NMR (400 MHz) $CDCl_3$: 7.99-7.97 (d, 1H), 7.66-7.64 (d, 2H), 7.44-7.40 (t, 2H), 7.22-7.18 (t, 1H), 6.94-6.92 (d, 2H), 3.82 (s, 3H), 3.68 (s, 3H); $^{13}$C-NMR (100 MHz) $CDCl_3$: 170.1, 161.5, 154.4, 138.2, 128.8, 127.5, 125.0, 123.5, 118.8, 114.2, 55.3, 39.6; LC/MS-MS: 267.0→77.2 m/z; GS1 and GS2 at 30, DP=81, CE=65, CXP=4, $t_R$=4.15 min.

3-(4-methoxyphenyl)-1-methyl-1H-pyrazol-5(4H)-one (9)

Ethyl-4-methoxybenzoylacetate (7.00 g, 27.8 mmol) in EtOH (100 mL) was treated at 0° C. with methyl-hydrazine (1.30 mL, 25.2 mmol). The mixture was allowed to slowly warm to ambient temperature and heated to 60° C. (3 h). The solvent was removed under vacuum and the residue purified by chromatography on silica gel (hexanes:EtOAc; 4:1 to 1:1) to afford 9 (3.00 g, 14.7 mmol, 58% yield) after crystallization from EtOH as a light yellow solid. $^1$H-NMR (400 MHz) DMSO: 10.9 (s, 1H), 7.63-7.60 (d, 2H), 6.92-6.90 (d, 2H), 5.70 (s, 1H), 3.76 (s, 3H), 3.54 (s, 3H); $^{13}$C-NMR (100 MHz) $CDCl_3$: 161.1, 153.4, 147.9, 126.3, 114.6, 114.4, 83.1, 59.7, 31.3; LC/MS-MS: 205.0→190.1 m/z; GS1 and GS2 at 30, DP=51, CE=29, CXP=12, $t_R$=3.44 min.

6-amino-1,3-dimethyl-4-phenyl-1,4-dihydropyrano[2,3-c]pyrazole-5-carbonitrile (10)

A mixture of benzaldehyde (290 μL, 2.87 mmol), malononitrile (190 mg, 2.87 mmol) and TEA (400 μL, 2.87 mmol) in EtOH (10 mL) was stirred for 1.0 min, followed by the addition of 2 (322 mg, 2.87 mmol). The reaction mixture was concentrated after 19 h and washed with EtOH and hexanes. The crude material was purified by column chromatography on $SiO_2$ (25% EtOAc in hexanes ramped to 100% EtOAc) and then re-crystallized from EtOH to give 10 (263 mg, 0.988 mmol, 34% yield) as a yellow powder. $^1$H-NMR (400 MHz) DMSO: 7.34-7.32 (m, 2H), 7.25-7.23 (t, 1H), 7.19-7.17 (d, 2H), 7.05 (s, 2H), 4.57 (s, 1H), 3.60 (s, 3H), 1.66 (s, 3H); $^{13}$C-NMR (100 MHz) DMSO: 159.9, 144.6, 144.4, 142.9, 128.8, 128.0, 127.3, 120.6, 96.5, 58.7, 37.5, 33.8, 12.8; LC/MS-MS: 267.0→201.3 m/z; GS1 and GS2 at 30, DP=61, CE=29, CXP=12, $t_R$=3.74 min.

6-amino-1-methyl-3,4-diphenyl-1,4-dihydropyrano[2,3-c]pyrazole-5-carbonitrile (11)

A mixture consisting of benzaldehyde (290 μL, 2.87 mmol), malononitrile (190 mg, 2.87 mmol) and TEA (400 μL, 2.87 mmol) in EtOH (10 mL) was stirred for 1.0 min, followed by the addition of 3 (500 mg, 2.87 mmol). The reaction mixture was concentrated after 21 h and washed with EtOH and hexanes; re-crystallized from EtOH to give 11 (282 mg, 8.58 mmol, 30% yield) as a white solid. $^1$H-NMR (400 MHz) DMSO: 7.41-7.38 (m, 2H), 7.28-7.24 (m, 2H), 7.21-7.18 (m, 6H), 4.88 (s, 1H), 4.77 (s, 2H), 3.83 (s, 3H); $^{13}$C-NMR (100 MHz) DMSO: 158.1, 146.0, 144.8, 144.6, 133.2, 128.7, 128.5, 127.9, 127.8, 127.1, 126.4, 120.5, 95.7, 59.9, 38.2, 34.5; LC/MS-MS: 329.1→263.1 m/z; GS1 and GS2 at 30, DP=71, CE=31, CXP=18, $t_R$=4.00 min.

6-amino-3-methyl-1,4-diphenyl-1,4-dihydropyrano[2,3-c]pyrazole-5-carbonitrile (12)

To a stirred solution of benzaldehyde (290 μL, 2.87 mmol), malononitrile (190 mg, 2.87 mmol) and 1 (500 mg, 2.87 mmol) in anhydrous DCM (60 mL) was added anhydrous $Na_2SO_4$ (407 mg, 2.87 mmol) and ethyl-hydrocupreine hydrochloride (46 mg, 0.122 mmol). The reaction mixture was stirred at room temperature (25 h). After filtration and washing with DCM, the solvent was removed under reduced pressure. The crude mixture was subjected to flash column chromatography over silica gel (hexanes:EtOAc; 1:1) to give 12 (270 mg, 0.822 mmol, 29% yield) as a white solid. $^1$H-NMR (400 MHz) $CDCl_3$: 7.69-7.66 (d, 2H), 7.50-7.46 (t, 2H), 7.39-7.26 (m, 6H), 4.68 (s, 1H), 4.67 (s, 2H), 1.91 (s, 3H), $^{13}$C-NMR (100 MHz) $CDCl_3$: 158.1, 146.4, 143.8, 141.9, 137.5, 129.2, 128.8, 127.8, 127.5, 126.7, 121.2, 119.0, 98.3, 64.0, 37.4, 12.8; LC/MS-MS: 329.1→263.1 m/z; GS1 and GS2 at 30, DP=56, CE=31, CXP=18, $t_R$=4.18 min.

6-amino-1,3,4-triphenyl-1,4-dihydropyrano[2,3-c]pyrazole-5-carbonitrile (13)

A mixture of benzaldehyde (290 μL, 2.87 mmol), malononitrile (190 mg, 2.87 mmol) and TEA (400 μL, 2.87 mmol) in EtOH (10 mL) was stirred for 1.0 min, followed by the addition of 4 (678 mg, 2.87 mmol). The precipitate was filtered off and washed with EtOH and hexanes, and re-crystallized from EtOH to give 13 (330 mg, 0.845 mmol, 29% yield) as a white solid. $^1$H-NMR (400 MHz) $CDCl_3$: 7.82-7.80 (d, 2H), 7.55-7.50 (m, 4H), 7.41-7.37 (t, 1H), 7.32-7.22 (m, 8H), 4.96 (s, 1H), 4.68 (s, 2H); $^{13}$C-NMR (100 MHz) $CDCl_3$: 157.5, 147.7, 144.9, 142.6, 137.5, 132.2, 129.3, 128.8, 128.2, 128.1, 127.5, 127.4, 127.1, 126.9, 121.6, 118.9, 97.5, 64.8, 38.2; LC/MS-MS: 391.1→325.0 m/z; GS1 and GS2 at 30, DP=91, CE=33, CXP=22, $t_R$=4.33 min.

6-amino-3-(4-methoxyphenyl)-1,4-diphenyl-1,4-dihydropyrano[2,3-c]pyrazole-5-carbonitrile (14)

A mixture of benzaldehyde (290 μL, 2.87 mmol, 1.0 equ.), malononitrile (190 mg, 2.87 mmol, 1.0 equ.) and TEA (400 μL, 2.87 mmol, 1.0 equ.) in EtOH (10 mL) was stirred for 1.0 min, followed by the addition of 8 (764 mg, 2.87 mmol). The reaction mixture was concentrated after 19 h and washed with EtOH and hexanes, re-crystallized from EtOH to give 14 (695 mg, 1.65 mmol, 58% yield) as a white solid. $^1$H-NMR (400 MHz) DMSO: 7.94-7.92 (d, 2H), 7.58-7.53 (m, 4H), 7.41-7.37 (t, 1H), 7.27-7.16 (m, 7H), 6.83-6.81 (d, 2H), 5.04 (s, 1H), 3.71 (s, 3H); $^{13}$C-NMR (100 MHz) DMSO: 159.5, 159.0, 146.6, 145.6, 144.5, 137.9, 129.8, 128.9, 128.3, 128.0, 127.3, 127.1, 125.1, 121.1, 120.3, 114.1, 97.5, 59.8, 55.5, 37.9; LC/MS-MS: 421.2→355.0 m/z; GS1 and GS2 at 30, DP=71, CE=33, CXP=24, $t_R$=4.3 min.

6-amino-3-(4-methoxyphenyl)-1-methyl-4-phenyl-1,4-dihydropyrano[2,3-c]pyrazole-5-carbonitrile (15)

A mixture of benzaldehyde (290 μL, 2.87 mmol, 1.0 equ.), malononitrile (190 mg, 2.87 mmol, 1.0 equ.) and TEA (400 μL, 2.87 mmol, 1.0 equ.) in EtOH (10 mL) was stirred for 1.0 min, followed by the addition of 9 (583 mg, 2.87 mmol). The reaction mixture was concentrated after 24 h. The crude material was purified by column chromatography (25% EtOAc in hexanes and ramped to 100% EtOAc), then re-crystallized from EtOH to give 15 (80.9 mg, 8% yield, 0.226 mmol) as a yellow solid. $^1$H-NMR (400 MHz) DMSO: 7.42-7.40 (d, 2H), 7.23-7.21 (m, 2H), 7.15-7.13 (d, 3H), 7.06 (s, 2H), 6.77-6.75 (d, 2H), 4.93 (s, 1H), 3.76 (s, 3H), 3.69 (s, 3H); $^{13}$C-NMR (100 MHz) DMSO: 159.1, 159.0, 145.9, 144.8, 144.5, 128.8, 127.8, 127.7, 127.1, 125.8, 120.5, 113.9, 95.0, 59.9, 55.4, 38.2, 34.4; LC/MS-MS: 359.1→293.0 m/z; GS1 and GS2 at 30, DP=76, CE=31, CXP=20, $t_R$=4.0 min.

6-amino-3-(3,4-dimethoxyphenyl)-1-methyl-4-phenyl-1,4-dihydropyrano[2,3-c]pyrazole-5-carbonitrile (16)

A mixture of benzaldehyde (145 μL, 1.44 mmol), malononitrile (90.0 mg, 1.44 mmol) and TEA (200 μL, 1.44 mmol) in EtOH (5.0 mL) was stirred for 1.0 min, followed by the addition of 6 (336 mg, 1.44 mmol). The reaction mixture was concentrated after 24 h. The crude material was purified by column chromatography (25% EtOAc in hexanes ramped to 100% EtOAc), then re-crystallized from EtOH to give 16 (48.5 mg, 9% yield, 0.124 mmol) as a yellow solid. $^1$H-NMR (400 MHz) $CDCl_3$: 7.29-7.28 (d, 2H), 7.23-7.21 (d, 2H), 7.00-6.98 (d, 1H), 6.88 (s, 1H), 6.72-6.70 (d, 2H), 4.84 (s, 1H), 4.75 (s, 2H), 3.82 (s, 6H), 3.60 (s, 3H); $^{13}$C-NMR (100 MHz) $CDCl_3$: 157.6, 148.7, 148.6, 146.1, 145.7, 143.1, 128.9, 127.5, 127.4, 125.6, 119.3, 119.2, 110.9, 109.7, 94.7, 64.4, 55.7, 55.6, 38.3, 34.1; LC/MS-MS: 389.1→323.0 m/z; GS1 and GS2 at 30, DP=66, CE=31, CXP=22, $t_R$=3.82 min.

6-amino-4-(4-fluorophenyl)-1,3-dimethyl-1,4-dihydropyrano[2,3-c]pyrazole-5-carbonitrile (17)

A mixture of 4-fluorobenzaldehyde (300 μL, 2.87 mmol), malononitrile (190 mg, 2.87 mmol) and TEA (400 mL, 2.87 mmol) in EtOH (8.0 mL) was stirred for 1.0 min, followed by the addition of 2 (322 mg, 2.87 mmol). The reaction mixture was concentrated after 24 h and washed with EtOH and hexanes, and re-crystallized from EtOH to give 17 (335 mg, 41% yield, 1.17 mmol) as a white solid. $^1$H-NMR (400 MHz) DMSO: 7.23-7.20 (m, 2H), 7.16-7.12 (m, 2H), 7.07 (s, 2H), 4.61 (s, 1H), 3.60 (s, 3H), 1.67 (s, 3H); $^{13}$C-NMR (100 MHz) DMSO: 162.7, 159.9 (d), 144.6, 142.9, 140.7, 129.9, 120.6, 115.5 (d), 96.3, 56.4, 36.7, 33.8, 12.8; LC/MS-MS: 285.1→219.1 m/z; GS1 and GS2 at 30, DP=61, CE=27, CXP=14, $t_R$=3.8 min.

6-amino-4-(4-fluorophenyl)-3-methyl-1-phenyl-1,4-dihydropyrano[2,3-c]pyrazole-5-carbonitrile (18)

A mixture of the 4-fluourobenzaldehyde (356 mg, 2.87 mmol), malononitrile (190 mg, 2.87 mmol, 1.0 equ.) and TEA (400 μL, 2.87 mmol) in EtOH (10 mL) was stirred for 1.0 min, followed by the addition of the 1 (500 mg, 2.87 mmol). The reaction mixture was concentrated after 18 h and the precipitate filtered and re-crystallized from EtOH to give 18 (85.0 mg, 0.245 mmol, 9% yield) as a white solid. $^1$H-NMR (400 MHz) $CDCl_3$: 7.68-7.66 (d, 2H), 7.50-7.46 (t, 2H), 7.34-7.32 (t, 1H), 7.28-7.22 (m, 2H) 7.08-7.04 (t, 2H), 4.68 (s, 3H), 1.91 (s, 3H); $^{13}$C-NMR (100 MHz) $CDCl_3$: 158.0, 146.2, 143.7, 137.8, 137.5, 129.4, 129.2, 126.8, 121.2, 118.8, 115.8, 115.6, 98.1, 63.8, 36.7, 12.8; LC/MS-MS: 347.1→281.1 m/z; GS1 and GS2 at 30, DP=11, CE=31, CXP=18, $t_R$=4.16 min.

6-amino-4-(4-fluorophenyl)-1-methyl-3-phenyl-1,4-dihydropyrano[2,3-c]pyrazole-5-carbonitrile (19)

A mixture of the 4-fluorobenzaldehyde (300 μL, 2.87 mmol), malononitrile (190 mg, 2.87 mmol) and TEA (400 μL, 2.87 mmol) in EtOH (10 mL) was stirred for 1.0 min, followed by the addition of 3 (500 mg, 2.87 mmol). The reaction mixture was concentrated after 20 h in vacuo and washed with EtOH and hexanes, and re-crystallized from EtOH to give 19 (182 mg, 0.525 mmol, 18% yield) as a light yellow solid. $^1$H-NMR (400 MHz) DMSO: 7.50-7.48 (d, 2H), 7.22-7.18 (m, 5H), 7.11 (s, 2H), 7.05-6.98 (t, 2H) 5.04 (s, 1H), 3.78 (s, 3H); $^{13}$C-NMR (100 MHz) DMSO: 162.5, 159.1, 146.0, 144.6, 140.9, 133.1, 129.8 (d), 128.5, 127.9, 126.5, 120.4, 115.4 (d), 95.5, 59.7, 37.4, 34.5; LC/MS-MS: 347.1→281.0 m/z; GS1 and GS2 at 30, DP=66, CE=31, CXP=14, $t_R$=4.0 min.

6-amino-4-(4-fluorophenyl)-1,3-diphenyl-1,4-dihydropyrano[2,3-c]pyrazole-5-carbonitrile (20)

A mixture of 4-fluorobenzaldehyde (300 μL, 2.87 mmol), malononitrile (190 mg, 2.87 mmol) and TEA (400 μL, 2.87 mmol) in ethanol (10 mL) was stirred for 1.0 min, followed by the addition of 4 (678 mg, 2.87 mmol). After 18 h, the precipitate formed was filtered out and washed with EtOH and hexanes, and re-crystallized from EtOH to afford 20 (240 mg, 0.588 mmol, 20% yield) as a white powder. $^1$H-NMR (400 MHz) DMSO: 7.94-7.92 (d, 2H), 7.61-7.55 (m, 4H), 7.42-7.38 (t, 1H), 7.28-7.24 (m, 7H), 7.06-7.02 (t, 2H), 5.15 (s, 1H), $^{13}$C-NMR (100 MHz) DMSO: 162.6, 159.0, 146.8, 145.6, 140.6, 137.8, 132.5, 130.0, 129.9 (d), 128.6, 128.6, 127.3, 127.0, 121.3, 120.2, 115.5 (d), 97.9, 59.6, 37.0; LC/MS-MS: 410.4→242.2 m/z; GS1 and GS2 at 30, DP=21, CE=47, CXP=16, $t_R$=4.6 min.

6-amino-3-(3,4-dimethoxyphenyl)-4-(4-fluorophenyl)-1-methyl-1,4-dihydropyrano[2,3-c]pyrazole-5-carbonitrile (21)

A mixture of 4-fluorobenzaldehyde (300 μL, 2.87 mmol), malononitrile (190 mg, 2.87 mmol, 1.0 equ.) and TEA (400 μL, 2.87 mmol) in EtOH (10 mL) was stirred for 1.0 min, followed by the addition of 6 (672 mg, 2.87 mmol). After 17 h, the precipitate formed was filtered out and washed with EtOH and hexanes, and re-crystallized from EtOH to give 21 (782 mg, 1.93 mmol, 67% yield) as a white powder. $^1$H-NMR (400 MHz) DMSO: 7.20-7.18 (m, 2H), 7.09-7.03 (m, 5H), 6.96-6.95 (d, 1H), 6.80-6.78 (d, 1H), 5.02 (s, 1H), 3.77 (s, 3H), 3.69 (s, 3H), 3.62 (s, 3H); $^{13}$C-NMR (100 MHz) DMSO: 162.6, 159.0, 148.7, 146.0, 144.6, 141.0, 129.8, 129.7, 125.9, 120.4, 119.0, 115.7, 115.4, 111.8, 109.8, 94.7, 55.8, 55.7, 37.3, 34.4; LC/MS-MS: 407.1→341.1 m/z; GS1 and GS2 at 30, DP=71, CE=33, CXP=22, $t_R$=3.9 min.

6-amino-4-(4-fluorophenyl)-3-(4-methoxyphenyl)-1-phenyl-1,4-dihydropyrano[2,3-c]pyrazole-5-carbonitrile (22)

A mixture of 4-fluorobenzaldehyde (300 μL, 2.87 mmol), malononitrile (190 mg, 2.87 mmol) and TEA (400 μL, 2.87 mmol, 1.0 equ.) in EtOH (10 mL) was stirred for 1.0 min, followed by the addition of 8 (764 mg, 2.87 mmol). After 17 h, the precipitate formed was filtered off and washed with EtOH and hexanes, and re-crystallized from EtOH to afford 22 (800 mg, 1.83 mmol, 64% yield) as white solid. $^1$H-NMR (400 MHz) DMSO: 7.93-7.91 (d, 2H), 7.55-7.53 (m, 4H), 7.41-7.37 (t, 1H), 7.26-7.23 (m, 4H), 7.07-7.05 (t, 2H), 6.84-6.82 (d, 2H), 5.11 (s, 1H), 3.72 (s, 3H); $^{13}$C-NMR (100 MHz) DMSO: 162.6, 159.0, 146.6, 145.5, 140.7, 140.6, 137.9, 130.0, 129.9 (d), 128.3, 127.1, 125.0, 121.1, 120.2, 115.5 (d), 114.1, 97.3, 59.6, 55.5, 37.0; LC/MS-MS: 439.2→373.0 m/z; GS1 and GS2 at 30, DP=61, CE=35, CXP=24, $t_R$=4.3 min.

6-amino-3-(3,4-dimethoxyphenyl)-4-(4-fluorophenyl)-1-phenyl-1,4-dihydropyrano[2,3-c]pyrazole-5-carbonitrile (23)

A mixture of 4-fluorobenzaldehyde (70.0 μL, 0.675 mmol), malononitrile (45.0 mg, 0.675 mmol) and TEA (90.0 μL, 0.675 mmol) in EtOH (3.0 mL) was stirred for 1.0 min, followed by the addition of the 7 (200 mg, 0.675 mmol). The reaction mixture was concentrated after 19 h and the crude material was purified by column chromatography (25% EtOAc in hexanes ramped to 100% EtOAc). The yellow solid was further purified by re-crystallization from EtOH to give 23 (164 mg, 0.350 mmol, 12% yield) as a white solid. $^1$H-NMR (400 MHz) $CDCl_3$: 7.80-7.78 (d, 2H), 7.52-7.48 (t, 2H), 7.38-7.35 (t, 1H), 7.25-7.21 (m, 2H), 7.05-6.95 (m, 4H), 6.75-6.73 (d, 1H), 4.91 (s, 1H), 4.84 (s, 2H), 3.84 (s, 3H), 3.71 (s, 3H); $^{13}$C-NMR (100 MHz) $CDCl_3$: 163.2, 157.8, 149.2, 148.7, 147.5, 144.9, 138.6, 137.4, 129.3, 129.1 (d), 127.1, 125.0, 121.5, 119.8, 119.0, 115.8 (d), 110.8, 109.9, 96.6, 64.0, 55.8, 55.7, 37.5; LC/MS-MS: 469.3→403.1 m/z; GS1 and GS2 at 30, DP=6, CE=35, CXP=26, $t_R$=4.2 min.

6-amino-4-(4-fluorophenyl)-3-(4-methoxyphenyl)-1-methyl-1,4-dihydropyrano[2,3-c]pyrazole-5-carbonitrile (24)

A mixture of 4-fluorobenzaldehyde (300 μL, 2.87 mmol), malononitrile (190 mg, 2.87 mmol) and TEA (400 μL, 2.87 mmol) in EtOH (10 mL) was stirred for 1.0 min, followed by the addition of 9 (586 mg, 2.87 mmol). The reaction mixture was concentrated after 19 h and the precipitate formed was washed with EtOH and hexanes, re-crystallized from EtOH gave 24 (350 mg, 0.930 mmol, 32% yield) as a white solid. $^1$H-NMR (400 MHz) DMSO: 7.43-7.40 (d, 2H), 7.20-7.16 (m, 2H), 7.10 (s, 2H), 7.06-7.02 (t, 2H), 6.78-6.76 (d, 2H), 4.99 (s, 1H), 3.75 (s, 3H), 3.69 (s, 3H); $^{13}$C-NMR (100 MHz) DMSO: 162.5, 159.1, 145.8, 144.6, 141.0, 141.0, 129.8 (d), 127.8, 125.7, 120.5, 115.5 (d), 113.9, 94.9, 59.7, 55.4, 37.4, 34.4; LC/MS-MS: 377.1→311.1 m/z; GS1 and GS2 at 30, DP=66, CE=33, CXP=20, $t_R$=4.0 min.

6-amino-4-(3,5-difluorophenyl)-1,3-dimethyl-1,4-dihydropyrano[2,3-c]pyrazole-5-carbonitrile (25)

A mixture of the 3,5-difluorobenzaldehyde (0.408 g, 2.87 mmol), malononitrile (0.190 g, 2.87 mmol) and TEA (0.40 mL, 2.87 mmol) in EtOH (10 mL) was stirred for 5 min, followed by the addition of the 2 (0.321 g, 2.87 mmol). The reaction mixture was concentrated after 23 h and the crude material was recrystallized from EtOH and washed with EtOH and n-hexanes to give 25 (291 mg, 0.963 mmol, 34% yield) as a white solid. $^1$H-NMR (400 MHz) DMSO: 7.15 (br-s, 2H), 7.09-7.05 (t, 1H), 6.92-6.89 (m, 2H), 4.66 (s, 1H), 3.57 (s, 3H), 1.68 (s, 3H); $^{13}$C-NMR (100 MHz) DMSO: 163.9 (d, CF), 163.8 (d, CF), 160.2, 149.2 (t), 144.8, 142.9, 120.4, 111.2 (m), 102.9 (t), 95.4, 57.5, 37.1, 33.9, 12.8. LC/MS-MS: 303.9→236.9 m/z; GS1 and GS2 at 30, DP=11, CE=31, CXP=16, $t_R$=4.19 min.

6-amino-4-(3,5-difluorophenyl)-1-methyl-3-phenyl-1,4-dihydropyrano[2,3-c]pyrazole-5-carbonitrile (26)

A mixture of 3,5-difluorobenzaldehyde (0.408 g, 2.87 mmol), malononitrile (0.190 g, 2.87 mmol) and TEA (0.40 mL, 2.87 mmol) in EtOH (10 mL) was stirred for 10 min, followed by the addition of 3 (0.500 g, 2.87 mmol, 1 equ.). The reaction mixture was concentrated after 23 h and the crude material was recrystallized from EtOH and to give 26 (282 mg, 0.77 mmol, 27% yield) as a white solid. $^1$H-NMR (400 MHz) DMSO: 7.48-7.47 (d, 2H), 7.24-7.17 (m, 5H), 6.97-6.92 (m, 1H), 6.87-6.85 (d, 2H), 5.11 (s, 1H), 3.74 (s, 3H); $^{13}$C-NMR (100 MHz) DMSO: 163.5 (d, CF), 163.5 (d, CF), 159.5, 146.1, 144.7, 133.0, 128.6, 128.1, 126.6, 126.5, 120.2, 111.3 (d), 102.8, 95.5, 58.5, 37.6, 34.6. LC/MS-MS: 365.1→299.0 m/z; GS1 and GS2 at 30, DP=86, CE=27, CXP=20, $t_R$=4.38 min.

6-amino-4-(4-methoxyphenyl)-3-methyl-1-phenyl-1,4-dihydropyrano[2,3-c]pyrazole-5-carbonitrile (27)

A mixture of anisaldehyde (350 μL, 2.87 mmol), malononitrile (190 mg, 2.87 mmol) and TEA (400 μL, 2.87 mmol) in EtOH (10 mL) was stirred for 1.0 min, followed by the addition of 1 (500 mg, 2.87 mmol). The reaction mixture was concentrated after 24 h and the precipitate was washed with EtOH and hexanes, and re-crystallized from EtOH to give 27 (800 mg, 78% yield, 2.23 mmol) as a white solid. $^1$H-NMR (400 MHz) DMSO: 7.80-7.78 (d, 2H), 7.51-7.47 (t, 2H), 7.32-7.28 (t, 1H), 7.18-7.16 (m, 4H), 6.91-6.89 (d, 2H), 4.62 (s, 1H), 3.74 (s, 3H), 1.79 (s, 3H); $^{13}$C-NMR (100 MHz) DMSO: 159.7, 158.6, 145.7, 144.2, 138.0, 136.0, 129.7, 129.2, 126.5, 120.5, 120.3, 114.3, 99.3, 59.0, 55.4, 36.4, 13.0; LC/MS-MS: 359.2→293.0 m/z; GS1 and GS2 at 30, DP=71, CE=29, CXP=20, $t_R$=4.14 min.

6-amino-4-(4-methoxyphenyl)-1,3-dimethyl-1,4-dihydropyrano[2,3-c]pyrazole-5-carbonitrile (28)

A mixture of anisaldehyde (350 μL, 2.87 mmol), malononitrile (190 mg, 2.87 mmol) and TEA (400 μL, 2.87 mmol) in EtOH (10 mL) was stirred for 1.0 min, followed by the addition of 2 (321 mg, 2.87 mmol). The reaction mixture was concentrated after 24 h and the crude material was purified by column chromatography (25% EtOAc in hexanes ramped to 100% EtOAc). The yellow solid was washed with EtOH and hexanes, and re-crystallized from EtOH to give 28 (370 mg, 1.25 mmol, 44% yield) as a white solid. $^1$H-NMR (400 MHz) $CDCl_3$: 7.12-7.10 (d, 2H), 6.85-6.83 (d, 2H), 4.61 (s, 2H), 4.55 (s, 1H), 3.79 (s, 3H), 3.69 (s, 3H), 1.80 (s, 3H); $^{13}$C-NMR (100 MHz) $CDCl_3$: 158.8, 157.9, 144.5, 144.4, 134.5, 128.8, 119.3, 114.0, 96.4, 64.2, 55.2, 36.7, 33.7, 12.7; LC/MS-MS: 297.0→231.2 m/z; GS1 and GS2 at 30, DP=61, CE=27, CXP=16, $t_R$=3.71 min.

6-amino-4-(4-methoxyphenyl)-1-methyl-3-phenyl-1,4-dihydropyrano[2,3-c]pyrazole-5-carbonitrile (29)

A mixture of anisaldehyde (350 μL, 2.87 mmol), malononitrile (190 mg, 2.87 mmol) and TEA (400 μL, 2.87 mmol) in EtOH (10 mL) was stirred for 1.0 min, followed by the addition of 3 (500 mg, 2.87 mmol). The reaction mixture was concentrated after 24 h and the precipitate was washed with EtOH and hexanes, and the product re-crystallized from EtOH to give 29 (210 mg, 20% yield, 0.586 mmol) as a white solid. $^1$H-NMR (400 MHz) DMSO: 7.50-7.48 (d, 2H), 7.21-7.17 (m, 3H), 7.05-7.02 (m, 4H), 6.76-6.74 (d, 2H), 4.91 (s, 1H), 3.76 (s, 3H), 3.64 (s, 3H); $^{13}$C-NMR (100 MHz) DMSO: 158.9, 158.3, 146.0, 144.6, 136.9, 133.2, 128.9, 128.5, 127.8, 126.4, 120.6, 114.1, 95.9, 60.3, 55.3, 37.5, 34.5; LC/MS-MS: 359.2→293.0 m/z; GS1 and GS2 at 30, DP=66, CE=29, CXP=20, $t_R$=3.98 min.

6-amino-4-(4-methoxyphenyl)-1-methyl-3-phenyl-1,4-dihydropyrano[2,3-c]pyrazole-5-carbonitrile (30)

A mixture of anisaldehyde (350 μL, 2.87 mmol), malononitrile (190 mg, 2.87 mmol) and TEA (400 μL, 2.87 mmol) in EtOH (10 mL) is stirred for 1.0 min, followed by the addition of 4 (678 mg, 2.87 mmol). The reaction mixture was concentrated after 24 h and the precipitate was washed with EtOH and hexanes. The product was re-crystallized from EtOH to afford 30 (1.05 g, 87% yield, 2.50 mmol) as a white solid. $^{1}$H-NMR (400 MHz) DMSO: 7.94-7.92 (d, 2H), 7.63-7.61 (d, 2H), 7.57-7.53 (t, 2H), 7.40-7.36 (t, 1H), 7.29-7.23 (m, 3H) 7.15 (s, 2H), 7.13-7.11 (d, 2H), 6.78-6.76 (d, 2H), 5.02 (s, 1H), 3.65 (s, 3H); $^{13}$C-NMR (100 MHz) DMSO: 158.9, 158.4, 146.7, 145.6, 137.9, 136.5, 132.6, 129.8, 129.0, 128.7, 128.5, 127.2, 127.0, 121.2, 120.3, 114.2, 98.3, 60.2, 55.3, 37.1; LC/MS-MS: 421.2→355.0 m/z; GS1 and GS2 at 30, DP=81, CE=35, CXP=24, $t_R$=4.32 min.

6-amino-3,4-bis(4-methoxyphenyl)-1-phenyl-1,4-dihydropyrano[2,3-c]pyrazole-5-carbonitrile (31)

A mixture of anisaldehyde (350 μL, 2.87 mmol, 1.0 equ.), malononitrile (190 mg, 2.87 mmol, 1.0 equ.) and TEA (400 μL, 2.87 mmol, 1.0 equ.) in EtOH (10 mL) was stirred for 1.0 min, followed by the addition 8 (764 mg, 2.87 mmol). The reaction mixture was concentrated after 24 h and the precipitate was washed with EtOH and hexanes, and then re-crystallized from EtOH to give 31 (1.06 g, 2.35 mmol, 82% yield) as a white solid. $^{1}$H-NMR (400 MHz) DMSO: 7.93-7.91 (d, 2H), 7.56-7.52 (m, 4H), 7.38-7.35 (t, 1H), 7.15-7.11 (m, 4H), 6.83-6.78 (m, 4H), 4.98 (s, 1H), 3.70 (s, 3H), 3.66 (s, 3H); $^{13}$C-NMR (100 MHz) DMSO: 159.5, 158.9, 158.4, 146.6, 145.5, 137.9, 136.6, 129.8, 129.0, 128.3, 127.0, 125.2, 121.0, 120.4, 114.2, 114.1, 97.7, 60.3, 55.5, 55.3, 37.1; LC/MS-MS: 452.3→89.1 m/z; GS1 and GS2 at 30, DP=36, CE=39, CXP=4, $t_R$=3.47 min.

6-amino-3,4-bis(4-methoxyphenyl)-1-methyl-1,4-dihydropyrano[2,3-c]pyrazole-5-carbonitrile (32)

A mixture of anisaldehyde (350 μL, 2.87 mmol), malononitrile (190 mg, 2.87 mmol) and TEA (400 μL, 2.87 mmol) in ethanol (10 mL) was stirred for 1.0 min, followed by the addition of 9 (689 mg, 2.87 mmol). The reaction mixture was concentrated after 24 h and the precipitate was washed with EtOH and hexanes, and then re-crystallized from EtOH to give 32 (690 mg, 1.78 mmol, 62% yield) as a white solid. $^{1}$H-NMR (400 MHz) DMSO: 7.42-7.40 (d, 2H), 7.05-7.03 (d, 2H), 7.00 (s, 2H), 6.78-6.75 (dd, 4H), 4.86 (s, 1H), 3.73 (s, 3H), 3.68 (s, 3H), 3.66 (s, 3H); $^{13}$C-NMR (100 MHz) DMSO: 159.0, 158.9, 158.3, 145.9, 144.5, 136.9, 128.9, 127.7, 125.9, 120.6, 114.1, 113.9, 95.3, 60.3, 55.4, 55.3, 37.5, 34.3; LC/MS-MS: 389.2→323.0 m/z; GS1 and GS2 at 30, DP=66, CE=29, CXP=22, $t_R$=3.94 min.

6-amino-4-(3-fluoro-4-methoxyphenyl)-1,3-dimethyl-1,4-dihydropyrano[2,3-c]pyrazole-5-carbonitrile (33)

A mixture of the 3-fluoro-4-methoxybenzaldehyde (0.442 g, 2.87 mmol), malononitrile (0.190 g, 2.87 mmol) and TEA (0.40 mL, 2.87 mmol) in EtOH (10 mL) was stirred for 5 min, followed by the addition of 2 (0.321 g, 2.87 mmol). The reaction mixture was concentrated after 18 h and the crude material was recrystallized from EtOH and the solid was washed with EtOH and n-hexanes to give 31 (475 mg, 1.51 mmol, 53% yield) as a light orange solid. $^{1}$H-NMR (400 MHz) DMSO: 7.10-7.04 (m, 3H), 6.95-6.93 (m, 2H), 4.53 (s, 1H), 3.79 (s, 3H), 3.56 (s, 3H), 1.65 (s, 3H); $^{13}$C-NMR (100 MHz) DMSO: 159.9, 153.0 (d, CF), 146.4 (d), 144.6, 142.9, 137.6 (d), 124.1, 120.6, 115.4 (d), 114.0, 96.2, 58.5, 56.4, 36.6, 33.9, 12.8. LC/MS-MS: 315.0→248.9 m/z; GS1 and GS2 at 30, DP=66, CE=27, CXP=16, $t_R$=4.05 min.

6-amino-1,3-dimethyl-4-(2,4,6-trimethoxyphenyl)-1,4-dihydropyrano[2,3-c]pyrazole-5-carbonitrile (34)

A mixture of the 2,4,6-trimethoxybenzaldehyde (0.563 g, 2.87 mmol), malononitrile (0.190 g, 2.87 mmol) and TEA (0.40 mL, 2.87 mmol) in EtOH (10 mL) was stirred for 10 min, followed by the addition of 2 (0.321 g, 2.87 mmol). The reaction mixture was concentrated after 26 h. The crude material was purified by column chromatography on $SiO_2$ (2% MeOH in DCM). The yellow solid was recrystallized from EtOH and washed with EtOH and n-hexanes to give 34 (60 mg, 0.168 mmol, 6% yield) as a yellow solid. $^{1}$H-NMR (400 MHz) DMSO: 6.72 (s, 2H), 6.20 (brs, 2H), 4.97 (s, 1H), 3.72 (s, 6H), 3.53 (s, 6H), 1.65 (s, 3H); $^{13}$C-NMR (100 MHz) DMSO: 161.3, 160.1, 145.4, 142.1, 121.3, 111.7, 96.5, 93.1, 91.2, 57.0, 56.6, 55.5, 33.7, 26.1, 12.2. LC/MS-MS: 357.1→189.0 m/z; GS1 and GS2 at 30, DP=56, CE=29, CXP=12, $t_R$=4.07 min.

6-amino-4-(3-fluoro-4-methoxyphenyl)-1-methyl-3-phenyl-1,4-dihydropyrano[2,3-c]pyrazole-5-carbonitrile (35)

A mixture of 3-fluoro-4-methoxybenz-aldehyde (0.442 g, 2.87 mmol), malononitrile (0.190 g, 2.87 mmol) and TEA (0.40 mL, 2.87 mmol) in EtOH (10 mL) was stirred for 10 min, followed by the addition of 3 (0.500 g, 2.87 mmol). The reaction mixture was concentrated after 18 h and the crude material was recrystallized from EtOH to give 35 (348 mg, 0.927 mmol, 33% yield) as a light white solid. $^{1}$H-NMR (400 MHz) DMSO: 7.50-48 (d, 2H), 7.22-7.15 (m, 3H), 7.07 (brs, 2H), 6.97-6.89 (m, 3H), 4.96 (s, 1H), 3.74 (s, 3H), 3.71 (s, 3H); $^{13}$C-NMR (100 MHz) DMSO: 159.1, 152.8 (d, CF), 146.1 (d), 146.0, 144.6, 137.9 (d), 133.2, 128.6, 127.9, 126.5, 124.0, 120.5, 115.2 (d), 113.9, 95.4, 59.7, 56.3, 37.2, 34.5. LC/MS-MS: 377.1→311.1 m/z; GS1 and GS2 at 30, DP=66, CE=31, CXP=20, $t_R$=4.27 min.

6-amino-1,3-dimethyl-4-(4-(trifluoromethyl)phenyl)-1,4-dihydropyrano[2,3-c]pyrazole-5-carbonitrile (36)

A mixture of the 4-(trifluoromethyl)benzaldehyde (0.500 g, 2.87 mmol), malononitrile (0.190 g, 2.87 mmol) and TEA (0.40 mL, 2.87 mmol) in EtOH (10 mL) was stirred for 10 min, followed by the addition of 2 (0.321 g, 2.87 mmol). The reaction mixture was concentrated after 22 h and purified by column chromatography on $SiO_2$ (2% MeOH in DCM) to give 36 (445 mg, 1.33 mmol, 46% yield) as a yellow solid. $^{1}$H-NMR (400 MHz) DMSO: 7.28 (s, 4H), 7.10 (brs, 2H), 4.64 (s, 1H), 3.57 (s, 3H), 1.64 (s, 3H); $^{13}$C-NMR (100 MHz) DMSO: 160.1, 147.6, 144.7, 143.9, 142.9, 129.9, 122.3, 121.4, 120.6, 96.2, 58.2, 36.8, 33.9, 12.8. LC/MS-MS: 337.2→59.1 m/z; GS1 and GS2 at 30, DP=26, CE=31, CXP=10, $t_R$=5.10 min.

6-amino-1-methyl-3-phenyl-4-(4-(trifluoromethyl)phenyl)-1,4-dihydropyrano[2,3-c]pyrazole-5-carbonitrile (37)

A mixture of 4-(trifluoromethyl)benzaldehyde (0.300 g, 1.72 mmol), malononitrile (0.114 g, 1.72 mmol) and TEA (0.240 mL, 1.72 mmol) in EtOH (6 mL) was stirred for 1.0 min, followed by the addition of 3 (300 mg, 1.72 mmol). The reaction mixture was concentrated after 22 h and purified by twice column chromatography on $SiO_2$ (2% MeOH in DCM) and then EtOAc:hexanes (1:1) to give 37 (120 mg, 0.301 mmol, 18% yield) as a light yellow solid. $^1$H-NMR (400 MHz) DMSO: 7.58-7.56 (d, 2H), 7.49-7.47 (d, 2H), 7.37-7.35 (d, 2H), 7.20-7.17 (m, 5H), 5.17 (s, 1H), 3.77 (s, 3H); $^{13}$C-NMR (100 MHz) DMSO: 159.4, 149.3, 146.1, 144.7, 133.0, 128.8, 128.6, 128.0, 126.4, 126.0, 125.7 (d), 123.3, 120.3, 94.9, 59.0, 37.9, 34.6. LC/MS-MS: 397.1→331.0 m/z; GS1 and GS2 at 30, DP=96, CE=33, CXP=22, $t_R$=4.44 min.

6-amino-1,3-dimethyl-4-(4-(trifluoromethoxy)phenyl)-1,4-dihydropyrano[2,3-c]pyrazole-5-carbonitrile (38)

A mixture of 4-(trifluoromethoxy)benzaldehyde (0.546 g, 2.87 mmol), malononitrile (0.190 g, 2.87 mmol) and TEA (0.40 mL, 2.87 mmol) in EtOH (10 mL) was stirred for 10 min, followed by the addition of 2 (0.321 g, 2.87 mmol). The reaction mixture was concentrated after 22 h and purified by column chromatography on $SiO_2$ (2% MeOH in DCM) to give 38 (359 mg, 1.03 mmol, 36% yield) as an orange solid. $^1$H-NMR (400 MHz) DMSO: 7.68-7.66 (d, 2H), 7.40-7.38 (d, 2H), 7.14 (brs, 2H), 4.71 (s, 1H), 3.58 (s, 3H), 1.64 (s, 3H); $^{13}$C-NMR (100 MHz) DMSO: 160.2, 149.2, 144.7, 142.9, 129.0, 127.2, 125.9, 124.1, 120.5, 95.8, 57.8, 37.2, 33.9, 12.8. LC/MS-MS: 352.0→335.1 m/z; GS1 and GS2 at 30, DP=26, CE=9, CXP=24, $t_R$=4.31 min.

6-amino-1-methyl-3-phenyl-4-(4-(trifluoromethoxy)phenyl)-1,4-dihydropyrano[2,3-c]pyrazole-5-carbonitrile (39)

A mixture of 4-(trifluoromethoxy)benzaldehyde (0.327 g, 1.72 mmol), malononitrile (0.114 g, 1.72 mmol) and TEA (0.240 mL, 1.72 mmol) in EtOH (6 mL) was stirred for 10 min, followed by the addition of 3 (300 mg, 1.72 mmol). The reaction mixture was concentrated after 22 h and purified by column chromatography on $SiO_2$ (2% MeOH in DCM) to give 39 (174 mg, 0.421 mmol, 25% yield) as yellow solid. $^1$H-NMR (400 MHz) DMSO: 7.47-7.45 (d, 2H), 7.26-7.24 (d, 2H), 7.20-7.14 (m, 7H), 5.08 (s, 1H), 3.76 (s, 3H); $^{13}$C-NMR (100 MHz) DMSO: 159.3, 147.4, 146.0, 144.7, 144.1, 133.1, 129.8, 128.6, 128.0, 126.5, 121.7, 121.2, 120.4, 95.3, 59.3, 37.4, 34.5. LC/MS-MS: 413.1→346.9 m/z; GS1 and GS2 at 30, DP=86, CE=33, CXP=24, $t_R$=4.49 min.

6-amino-4-(4-cyanophenyl)-1,3-dimethyl-1,4-dihydropyrano[2,3-c]pyrazole-5-carbonitrile (40)

A mixture of 4-formylbenzonitrile (0.376 g, 2.87 mmol), malononitrile (0.190 g, 2.87 mmol) and TEA (0.40 mL, 2.87 mmol) in EtOH (10 mL) was stirred for 10 min, followed by the addition of 2 (0.321 g, 2.87 mmol). The reaction mixture was concentrated after 18 h and the crude material was purified by column chromatography on $SiO_2$ (2% MeOH in DCM). The yellow solid was washed with EtOH and n-hexanes, and recrystallized from EtOH to give 40 (484 mg, 1.66 mmol, 58% yield) as a white off solid. $^1$H-NMR (400 MHz) DMSO: 7.78-7.76 (d, 2H), 7.38-7.36 (d, 2H), 7.17 (brs, 2H), 4.70 (s, 1H), 3.57 (s, 3H), 1.63 (s, 3H); $^{13}$C-NMR (100 MHz) DMSO: 160.2, 150.1, 144.7, 142.9, 133.0, 129.2, 120.4, 119.2, 110.2, 95.6, 57.5, 37.4, 33.9, 12.8. LC/MS-MS: 292.0→226.2 m/z; GS1 and GS2 at 30, DP=51, CE=31, CXP=14, $t_R$=3.90 min.

6-amino-4-(4-cyanophenyl)-1-methyl-3-phenyl-1,4-dihydropyrano[2,3-c]pyrazole-5-carbonitrile (41)

A mixture of 4-formylbenzonitrile (0.376 g, 2.87 mmol), malononitrile (0.190 g, 2.87 mmol) and TEA (0.40 mL, 2.87 mmol) in EtOH (10 mL) was stirred for 10 min, followed by the addition of 3 (500 mg, 2.87 mmol). The reaction mixture was concentrated after 18 h and the crude material was purified by recrystallization from EtOH and n-hexanes to give 41 (160 mg, 0.453 mmol, 16% yield) as a white off solid. $^1$H-NMR (400 MHz) DMSO: 7.68-7.66 (d, 2H), 7.48-7.46 (d, 2H), 7.35-7.33 (d, 2H), 7.22-7.19 (m, 5H), 5.17 (s, 1H), 3.77 (s, 3H); $^{13}$C-NMR (100 MHz) DMSO: 159.4, 150.2, 146.1, 144.7, 133.0, 132.8, 129.1, 128.7, 128.1, 126.5, 120.2, 119.1, 110.0, 94.7, 58.6, 38.0, 34.6. LC/MS-MS: 354.2→288.1 m/z; GS1 and GS2 at 30, DP=66, CE=33, CXP=20, $t_R$=4.21 min.

6-amino-4-(4-isopropylphenyl)-1,3-dimethyl-1,4-dihydropyrano[2,3-c]pyrazole-5-carbonitrile (42)

A mixture of 4-isopropylbenzaldehyde (0.425 g, 2.87 mmol), malononitrile (0.190 g, 2.87 mmol) and TEA (0.40 mL, 2.87 mmol) in EtOH (10 mL) was stirred for 10 min, followed by the addition of 2 (0.321 g, 2.87 mmol). The reaction mixture was concentrated after 22 h and precipitate was filtered off and washed with EtOH to give 42 (163 mg, 0.528 mmol, 18% yield) as a light yellow solid. $^1$H-NMR (400 MHz) DMSO: 7.16-7.14 (d, 2H), 7.05-7.03 (d, 2H), 6.99 (s, 2H), 4.50 (s, 1H), 3.56 (s, 3H), 2.85-2.79 (m, 1H), 1.64 (s, 3H), 1.17-1.15 (d, 6H); $^{13}$C-NMR (100 MHz) DMSO: 160.0, 147.2, 144.6, 142.9, 141.9, 127.9, 126.7, 120.8, 96.7, 58.8, 37.1, 33.9, 33.4, 24.3, 12.9. LC/MS-MS: 309.1→243.0 m/z; GS1 and GS2 at 30, DP=71, CE=31, CXP=16, $t_R$=4.44 min.

6-amino-4-(4-isopropylphenyl)-1-methyl-3-phenyl-1,4-dihydropyrano[2,3-c]pyrazole-5-carbonitrile (43)

A mixture of 4-isopropylbenzaldehyde (0.254 g, 1.72 mmol), malononitrile (0.114 g, 1.72 mmol) and TEA (0.240 mL, 1.72 mmol) in ethanol (6 mL) was stirred for 10 min, followed by the addition of 3 (0.300 g, 1.72 mmol). The reaction mixture was concentrated after 22 h and purified by column chromatography on $SiO_2$ twice (2% MeOH in DCM) and then EtOAc:Hexanes; 1:1) to give 43 (207 mg, 0.559 mmol, 33% yield) as a yellow solid. $^1$H-NMR (400 MHz) DMSO: 7.50-7.48 (d, 2H), 7.22-7.16 (m, 3H), 7.09-7.02 (m, 6H), 4.92 (s, 1H), 3.76 (s, 3H), 2.80-2.73 (m, 1H), 1.12-1.10 (d, 6H); $^{13}$C-NMR (100 MHz) DMSO: 159.2, 147.1, 146.1, 144.5, 142.3, 133.3, 128.6, 127.9, 127.7, 126.7, 126.4, 120.7, 95.9, 60.1, 37.9, 34.5, 33.3, 24.2. LC/MS-MS: 371.1→305.0 m/z; GS1 and GS2 at 30, DP=106, CE=29, CXP=20, $t_R$=4.60 min.

6-amino-4-(2,3-dihydrobenzo[b][1,4]dioxin-6-yl)-1,3-dimethyl-1,4-dihydropyrano[2,3-c]pyrazole-5-carbonitrile (44)

A mixture of the 1,4-benzodioxan-6-carboxaldehyde (0.471 g, 2.87 mmol), malononitrile (0.190 g, 2.87 mmol) and TEA (0.40 mL, 2.87 mmol) in EtOH (10 mL) was stirred for 5 min, followed by the addition of 2 (0.321 g, 2.87 mmol). The reaction mixture was concentrated after 23 h and the crude material was recrystallized from EtOH and washed with EtOH and n-hexanes to give 44 (131 mg, 0.404 mmol, 14% yield) as a yellow solid. $^1$H-NMR (400 MHz) DMSO: 6.98 (brs, 2H), 6.76-6.74 (d, 1H), 6.59-6.57 (m, 2H), 4.43 (s, 1H), 4.18 (s, 4H), 3.56 (s, 3H), 1.67 (s, 3H); $^{13}$C-NMR (100 MHz) DMSO: 159.9, 144.6, 143.5, 143.0, 142.6, 137.7, 120.7, 120.7, 117.3, 116.5, 96.6, 64.5, 64.4, 58.9, 36.8, 33.9, 12.9. LC/MS-MS: 325.0→259.1 m/z; GS1 and GS2 at 30, DP=51, CE=29, CXP=18, $t_R$=3.98 min.

6-amino-4-(2,3-dihydrobenzo[b][1,4]dioxin-6-yl)-1-methyl-3-phenyl-1,4-dihydropyrano[2,3-c]pyrazole-5-carbonitrile (45)

A mixture of 1,4-benzodioxan-6-carboxaldehyde (0.471 g, 2.87 mmol), malononitrile (0.190 g, 2.87 mmol) and TEA (0.40 mL, 2.87 mmol) in EtOH (10 mL) was stirred for 10 min, followed by the addition of 3 (0.500 g, 2.87 mmol). The reaction mixture was concentrated after 23 h and the crude material was purified by column chromatography on $SiO_2$ (2% MeOH in DCM) and then recrystallized from EtOH to give 45 (93 mg, 0.240 mmol, 8% yield) as a yellow solid. $^1$H-NMR (400 MHz) DMSO: 7.53-7.51 (d, 2H), 7.25-7.18 (m, 3H), 7.03 (brs, 2H), 6.98-6.66 (d, 1H), 6.60-6.57 (m, 2H), 4.86 (s, 1H), 4.13 (s, 4H), 3.75 (s, 3H); $^{13}$C-NMR (100 MHz) DMSO: 159.1, 146.0, 144.5, 143.5, 142.5, 138.1, 133.3, 128.7, 127.9, 126.5, 120.6, 120.5, 117.2, 116.3, 95.8, 64.4, 64.3, 60.2, 37.5, 34.5. LC/MS-MS: 387.1→321.0 m/z; GS1 and GS2 at 30, DP=66, CE=31, CXP=22, $t_R$=4.25 min.

6-amino-1,3-dimethyl-4-(pyridin-4-yl)-1,4-dihydropyrano[2,3-c]pyrazole-5-carbonitrile (46)

A mixture of 3-pyridincarboxaldehyde (0.307 g, 2.87 mmol), malononitrile (0.190 g, 2.87 mmol) and TEA (0.40 mL, 2.87 mmol) in ethanol (10 mL) was stirred for 10 min, followed by the addition of 2 (0.321 g, 2.87 mmol). The reaction mixture was concentrated after 22 h and purified by column chromatography on $SiO_2$ (2% MeOH in DCM) and washed with EtOH to give 46 (132 mg, 0.493 mmol, 17% yield) as a light orange solid. $^1$H-NMR (400 MHz) DMSO: 8.49-8.48 (d, 2H), 7.18-7.18 (m, 4H), 4.61 (s, 1H), 3.58 (s, 3H), 1.66 (s, 3H); $^{13}$C-NMR (100 MHz) DMSO: 160.4, 152.9, 150.3, 144.8, 142.9, 123.4, 120.4, 95.2, 57.1, 36.8, 33.9, 12.8. LC/MS-MS: 268.0→189.1 m/z; GS1 and GS2 at 30, DP=56, CE=25, CXP=12, $t_R$=3.38 min.

6-amino-1-methyl-3-phenyl-4-(pyridin-4-yl)-1,4-dihydropyrano[2,3-c]pyrazole-5-carbonitrile (47)

A mixture of 3-pyridincarboxaldehyde (0.307 g, 2.87 mmol), malononitrile (0.190 g, 2.87 mmol) and TEA (0.40 mL, 2.87 mmol) in EtOH (10 mL) was stirred for 10 min, followed by the addition of 3 (500 mg, 2.87 mmol). After 22 h the precipitate was filtered off and washed with EtOH and hexanes to give 47 (340 mg, 1.03 mmol, 36% yield) as a white solid. $^1$H-NMR (400 MHz) DMSO: 8.38-8.36 (dd, 2H), 7.48-7.46 (d, 2H), 7.22-7.13 (m, 7H), 5.08 (s, 1H), 3.77 (s, 3H); $^{13}$C-NMR (100 MHz) DMSO: 159.6, 153.0, 150.1, 146.1, 144.7, 133.0, 128.7, 128.1, 126.5, 123.2, 120.2, 94.3, 58.2, 37.4, 34.6. LC/MS-MS: 330.1→80.1 m/z; GS1 and GS2 at 30, DP=76, CE=63, CXP=4, $t_R$=3.94 min.

6-amino-1,3-dimethyl-4-(pyridin-3-yl)-1,4-dihydropyrano[2,3-c]pyrazole-5-carbonitrile (48)

A mixture of 3-pyridincarboxaldehyde (0.307 g, 2.87 mmol), malononitrile (0.190 g, 2.87 mmol) and TEA (0.40 mL, 2.87 mmol) in ethanol (10 mL) was stirred for 5 min, followed by the addition of 2 (0.321 g, 2.87 mmol). The reaction mixture was concentrated after 22 h and the precipitate was filtered off and washed with EtOH to give 48 (463 mg, 1.73 mmol, 60% yield) as a white solid. $^1$H-NMR (400 MHz) DMSO: 8.43-8.43 (d, 2H), 7.53-7.51 (d, 1H), 7.34-7.31 (m, 1H), 7.14 (brs, 2H), 4.63 (s, 1H), 3.57 (s, 3H), 1.64 (s, 3H); $^{13}$C-NMR (100 MHz) DMSO: 160.2, 149.4, 148.8, 144.8, 142.8, 139.7, 135.8, 124.2, 120.5, 95.7, 57.8, 35.0, 33.9, 12.8. LC/MS-MS: 268.0→189.2 m/z; GS1 and GS2 at 30, DP=71, CE=34, CXP=12, $t_R$=3.5 min.

6-amino-1-methyl-3-phenyl-4-(pyridin-3-yl)-1,4-dihydropyrano[2,3-c]pyrazole-5-carbonitrile (49)

A mixture of 3-pyridincarboxaldehyde (0.307 g, 2.87 mmol), malononitrile (0.190 g, 2.87 mmol) and TEA (0.40 mL, 2.87 mmol) in EtOH (10 mL) was stirred for 10 min, followed by the addition of 3 (500 mg g, 2.87 mmol). A white precipitate was formed and filtered off after 22 h. The formed precipitate was recrystallized with EtOH to give 49 (389 mg, 1.19 mmol, 41% yield) as a white solid. $^1$H-NMR (400 MHz) DMSO: 8.41-8.40 (d, 1H), 8.30-8.29 (dd, 1H), 7.49-7.47 (d, 3H), 7.23-7.16 (m, 6H), 5.12 (s, 1H), 3.77 (s, 3H); $^{13}$C-NMR (100 MHz) DMSO: 159.4, 149.3, 148.5, 146.1, 144.7, 139.9, 135.6, 133.0, 128.6, 128.0, 126.5, 124.0, 120.4, 94.8, 58.9, 35.6, 34.6. LC/MS-MS: 330.1→80.1 m/z; GS1 and GS2 at 30, DP=56, CE=57, CXP=14, $t_R$=3.96 min.

6-amino-4-(6-bromopyridin-2-yl)-1,3-dimethyl-1,4-dihydropyrano[2,3-c]pyrazole-5-carbonitrile (50)

A mixture of 6-bromo-2-pyridincarboxaldehyde (0.307 g, 2.87 mmol), malononitrile (0.190 g, 2.87 mmol) and TEA (0.40 mL, 2.87 mmol) in EtOH (10 mL) was stirred for 10 min, followed by the addition of 2 (0.321 g, 2.87 mmol). The reaction mixture was filtered after 22 h and the precipitate was filtered off and washed with EtOH to give 50 (427 mg, 1.23 mmol, 43% yield) as a white solid. $^1$H-NMR (400 MHz) DMSO: 7.73-7.69 (t, 1H), 7.50-7.48 (d, 1H), 7.32-7.30 (d, 1H), 7.19 (brs, 2H), 4.69 (s, 1H), 3.56 (s, 3H), 1.71 (s, 3H); $^{13}$C-NMR (100 MHz) DMSO: 164.4, 160.7, 144.7, 142.9, 141.4, 140.8, 127.0, 122.0, 120.5, 95.3, 56.3, 39.3, 33.9, 12.8. LC/MS-MS: 348.0→283.0 m/z; GS1 and GS2 at 30, DP=66, CE=25, CXP=18, $t_R$=4.00 min.

6-amino-4-(6-bromopyridin-2-yl)-1-methyl-3-phenyl-1,4-dihydropyrano[2,3-c]pyrazole-5-carbonitrile (51)

A mixture of 6-bromo-2-pyridincarboxaldehyde (0.307 g, 2.87 mmol), malononitrile (0.190 g, 2.87 mmol) and TEA (0.40 mL, 2.87 mmol) in EtOH (10 mL) was stirred for 10 min, followed by the addition of 3 (500 g, 2.87 mmol). The reaction mixture was filtered after 22 h and the precipitate was filtered off and washed with EtOH to give 51 (971 mg, 2.38 mmol, 83% yield) as a white solid. $^1$H-NMR (400 MHz) DMSO: 7.59-7.53 (t, 1H), 7.52-7.50 (d, 2H), 7.38-7.35 (d, 1H), 7.30-7.26 (d, 1H), 7.24-7.21 (m, 5H), 5.12 (s, 1H), 3.76 (s, 3H); $^{13}$C-NMR (100 MHz) DMSO: 164.4, 160.0, 146.0, 144.7, 141.2, 140.5, 133.0, 128.6, 128.1, 126.9, 126.4, 122.2, 120.2, 94.6, 57.5, 39.3, 34.5. LC/MS-MS: 408.0→175.1 m/z; GS1 and GS2 at 30, DP=86, CE=31, CXP=10, $t_R$=4.28 min.

4-(4-(1H-imidazol-1-yl)phenyl)-6-amino-1,3-dimethyl-1,4-dihydropyrano[2,3-c]pyrazole-5-carbonitrile (52)

A mixture of the 4-(1H-imidazol-1-yl)benzaldehyde (0.494 g, 2.87 mmol), malononitrile (0.190 g, 2.87 mmol) and TEA (0.40 mL, 2.87 mmol) in EtOH (10 mL) was stirred for 1.0 min, followed by the addition of the 2 (0.321 g, 2.87 mmol). The reaction mixture was concentrated after 22 h and purified by column chromatography on $SiO_2$ (2% MeOH in DCM) to give 52 (322 mg, 0.967 mmol, 34% yield) as a light brown solid. $^1$H-NMR (400 MHz) DMSO: 8.20 (s, 1H), 7.69 (s, 1H), 7.58-7.56 (d, 2H), 7.29-7.27 (d, 2H), 7.09-7.07 (d, 3H), 4.64 (s, 1H), 3.58 (s, 3H), 1.68 (s, 3H); $^{13}$C-NMR (100 MHz) DMSO: 160.1, 144.7, 143.2, 143.0, 136.1, 136.0, 130.3, 129.5, 121.0, 120.7, 118.5, 95.3, 58.4, 36.9, 33.9, 12.9. LC/MS-MS: 333.3→266.9 m/z; GS1 and GS2 at 30, DP=61, CE=41, CXP=18, $t_R$=3.4 min.

4-(4-(1H-imidazol-1-yl)phenyl)-6-amino-1-methyl-3-phenyl-1,4-dihydropyrano[2,3-c]pyrazole-5-carbonitrile (53)

A mixture 4-(1H-imidazol-1-yl)benzaldehyde (0.296 g, 1.72 mmol), malononitrile (0.114 g, 1.72 mmol) and TEA (0.240 mL, 1.72 mmol) in EtOH (6 mL) was stirred for 10 min, followed by the addition of 3 (0.300 g, 1.72 mmol). The reaction mixture was concentrated after 22 h and purified by column chromatography on $SiO_2$ (2% MeOH in DCM) to give 53 (308 mg, 0.780 mmol, 45% yield) as a white off solid. $^1$H-NMR (400 MHz) DMSO: 8.15 (s, 1H), 7.64 (s, 1H), 7.54-7.52 (d, 2H), 7.49-7.47 (d, 2H), 7.28-7.13 (m, 7H), 7.04 (s, 1H), 5.09 (s, 1H), 3.78 (s, 3H); $^{13}$C-NMR (100 MHz) DMSO: 159.2 145.1, 144.6, 143.5, 135.9, 135.9, 133.2, 130.2, 129.3, 128.7, 128.0, 126.5, 120.7, 120.5, 118.4, 95.4, 59.6, 37.6, 34.6. LC/MS-MS: 395.2→144.0 m/z; GS1 and GS2 at 30, DP=101, CE=59, CXP=8, $t_R$=3.89 min.

COMPOUND 54

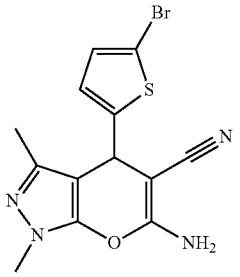

Chemcial Formula: $C_{13}H_{11}BrN_4OS$
Molecular Weight: 351.22

6-amino-4-(5-bromothiophen-2-yl)-1,3-dimethyl-1,4-dihydropyrano[2,3-c]pyrazole-5-carbonitrile (54)

A mixture of the 5-bromothiophene-2-carbaldehyde (0.548 g, 2.87 mmol), malononitrile (0.190 g, 2.87 mmol) and triethylamine (0.40 mL, 2.87 mmol) in ethanol (10 mL) was stirred for 10 min, followed by the addition of 2 (0.321 g, 2.87 mmol). The reaction mixture was filtered after 22 h and precipitate was recrystallized with ethanol to give 54 (221 mg, 0.628 mmol, 22% yield) as a light orange solid. $^1$H-NMR (400 MHz) DMSO: 7.18 (s, 2H), 7.02-7.02 (d, 1H), 6.86-6.85 (d, 1H), 4.93 (s, 1H), 3.56 (s, 3H), 1.81 (s, 3H); $^{13}$C-NMR (100 MHz) DMSO: 159.9, 151.9, 144.2, 143.1, 130.3, 126.0, 120.3, 110.8, 95.8, 58.3, 33.9, 33.2, 12.8. LC/MS-MS: 352.9→287.0 m/z; GS1 and GS2 at 30, DP=66, CE=29, CXP=18, $t_R$=4.3 min.

COMPOUND 55

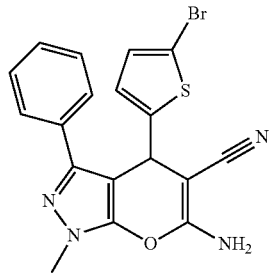

Chemcial Formula: $C_{18}H_{13}BrN_4OS$
Molecular Weight: 413.29

6-amino-4-(5-bromothiophen-2-yl)-1-methyl-3-phenyl-1,4-dihydropyrano[2,3-c]pyrazole-5-carbonitrile (55)

A mixture of 5-bromothiophene-2-carbaldehyde (0.328 g, 1.72 mmol), malononitrile (0.114 g, 1.72 mmol) and triethylamine (0.240 mL, 1.72 mmol) in ethanol (6 mL) was stirred for 10 min, followed by the addition of 3 (0.300 g, 1.72 mmol). The reaction mixture was concentrated after 22 h and purified by column chromatography on $SiO_2$ (2% MeOH in DCM) to give 55 (80 mg, 0.194 mmol, 11% yield) as orange solid. $^1$H-NMR (400 MHz) DMSO: 7.61-7.59 (d, 2H), 7.30-7.23 (m, 5H), 6.92-6.91 (d, 1H), 6.78-6.77 (d, 1H), 5.41 (s, 1H), 3.74 (s, 3H); $^{13}$C-NMR (100 MHz) DMSO: 159.3, 151.9, 145.4, 144.8, 133.0, 130.3, 128.8, 128.2, 126.6, 125.8, 120.2, 110.4, 95.2, 59.1, 34.5, 33.9. LC/MS-MS: 415.1→348.0 m/z; GS1 and GS2 at 30, DP=81, CE=31, CXP=22, $t_R$=4.5 min.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A compound having a chemical structure selected from the group consisting of:

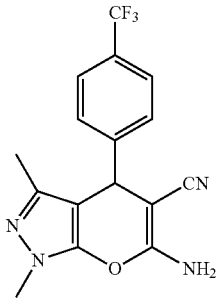

6-amino-1,3-dimethyl-4-(4-(trifluoromethyl)phenyl)-1,4-dihydropyrano[2,3-c]pyrazole-5-carbonitrile,

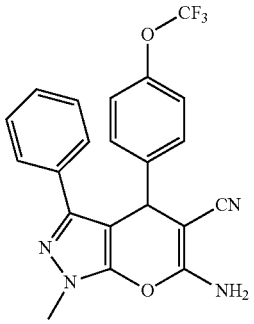

6-amino-1-methyl-3-phenyl-4-(4-(trifluoromethoxy)phenyl)-1,4-dihydropyrano[2,3-c]pyrazole-5-carbonitrile,

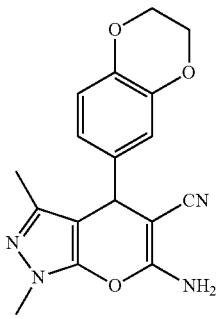

6-amino-4-(2,3-dihydrobenzo[b][1,4]dioxin-6-yl)-1,3-dimethyl-1,4-dihydropyrano[2,3-c]pyrazole-5-carbonitrile, [and,

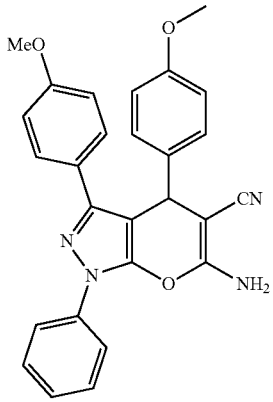

6-amino-3,4-bis(4-methoxyphenyl)-1-phenyl-1,4-dihydropyrano[2,3-c]pyrazole-5-carbonitrile] and pharmaceutically acceptable enantiomers, diastereomers, racemates, or salts thereof.

2. A pharmaceutical composition comprising at least one compound of claim 1 and at least one pharmaceutical excipient.

3. A method of treating, ameliorating cancer or preventing metastasis of a cancer in a subject comprising administering a therapeutically-effective amount of a compound of claim 1 that inhibits a Ral GTPase to a subject in need thereof.

4. The method of claim 3, wherein the compound is administered to the subject within a pharmaceutical composition.

5. The method of claim 4, wherein the pharmaceutical composition is a mono-phasic pharmaceutical composition suitable for parenteral or oral administration consisting essentially of a therapeutically-effective amount of the compound, and a pharmaceutically acceptable carrier.

6. The method of claim 4, wherein the pharmaceutical composition is administered in conjunction with one or more geranylgeranyltransferase type I (GGTase-I) inhibitors, surgery, chemotherapy, radiation, immunotherapy, or combinations thereof.

7. A compound having a chemical structure selected from the group consisting of:

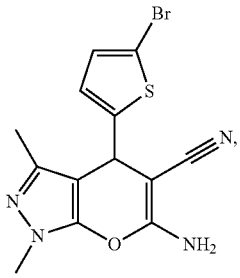

N, [and]

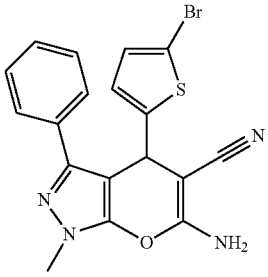

and pharmaceutically acceptable enantiomers, diastereomers, racemates, or salts thereof.

8. A method of treating, ameliorating cancer or preventing metastasis of a cancer in a subject comprising administering a therapeutically-effective amount of a compound that inhibits a Ral GTPase to a subject in need thereof, wherein the compound has a chemical structure selected from *the group consisting of*:

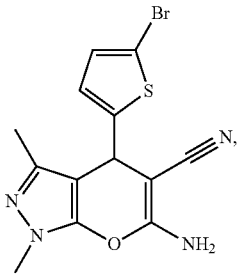

[and]

-continued

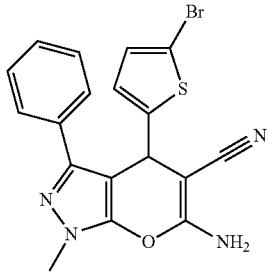

and pharmaceutically acceptable enantiomers, diastereomers, racemates, or salts thereof.

* * * * *